(12) United States Patent
Pacione et al.

(10) Patent No.: US 8,398,546 B2
(45) Date of Patent: Mar. 19, 2013

(54) SYSTEM FOR MONITORING AND MANAGING BODY WEIGHT AND OTHER PHYSIOLOGICAL CONDITIONS INCLUDING ITERATIVE AND PERSONALIZED PLANNING, INTERVENTION AND REPORTING CAPABILITY

(75) Inventors: Christopher Pacione, Pittsburgh, PA (US); Steve Menke, Mars, PA (US); David Andre, Pittsburgh, PA (US); Eric Teller, Pittsburgh, PA (US); Scott Safier, Pittsburgh, PA (US); Raymond Pelletier, Pittsburgh, PA (US); Mark Handel, Pittsburgh, PA (US); Jonathan Farringdon, Pittsburgh, PA (US); Eric Hsiung, Pittsburgh, PA (US); Suresh Vishnubhatla, Wexford, PA (US); James Hanlon, Library, PA (US); John M. Stivoric, Pittsburgh, PA (US); Neal Spruce, Westlake Village, CA (US); Steve Shassberger, Lansing, MI (US)

(73) Assignee: BodyMedia, Inc., Pittsburgh, PA (US)

( * ) Notice: Subject to any disclaimer, the term of this patent is extended or adjusted under 35 U.S.C. 154(b) by 32 days.

(21) Appl. No.: 10/940,214

(22) Filed: Sep. 13, 2004

(65) Prior Publication Data
US 2005/0113650 A1 May 26, 2005

Related U.S. Application Data

(63) Continuation-in-part of application No. 10/638,588, filed on Aug. 11, 2003, now Pat. No. 6,605,038, which is a continuation of application No. 09/602,537, filed on Jun. 23, 2000, now Pat. No. 7,689,437, which is a continuation-in-part of application No. 09/595,660, filed on Jun. 16, 2000.

(60) Provisional application No. 60/502,764, filed on Sep. 13, 2003, provisional application No. 60/555,280, filed on Mar. 22, 2004.

(51) Int. Cl.
*A61B 5/00* (2006.01)
(52) U.S. Cl. ........ 600/300; 600/301; 128/920; 128/921; 705/2; 705/3; 706/45
(58) Field of Classification Search .......... 600/300–301, 600/509, 500, 529, 356, 485, 549; 128/920–925; 434/262, 127, 326, 107, 219, 238, 247; 705/2–3
See application file for complete search history.

(56) References Cited

U.S. PATENT DOCUMENTS

| 3,870,034 A | 3/1975 | James et al. |
| 4,031,365 A | 6/1977 | Raggiotti et al. |

(Continued)

FOREIGN PATENT DOCUMENTS
BR P0001075-8 11/2001
(Continued)

OTHER PUBLICATIONS
Thermal Gap Fillers, Kent Young, Feb. 6, 2001 (article downloaded from www.chomerics.com).
(Continued)

*Primary Examiner* — Sam Yao
*Assistant Examiner* — Marie Archer
(74) *Attorney, Agent, or Firm* — GTC Law Group LLP & Affiliates; John A. Monocello, III

(57) ABSTRACT

A nutrition and activity management system is disclosed that monitors energy expenditure of an individual through the use of a body-mounted sensing apparatus. The apparatus is particularly adapted for continuous wear. The system is also adaptable or applicable to measuring a number of other physiological parameters and reporting the same and derivations of such parameters. A weight management embodiment is directed to achieving an optimum or preselected energy balance between calories consumed and energy expended by the user. An adaptable computerized nutritional tracking system is utilized to obtain data regarding food consumed, Relevant and predictive feedback is provided to the user regarding the mutual effect of the user's energy expenditure, food consumption and other measured or derived or manually input physiological contextual parameters upon progress toward said goal.

29 Claims, 27 Drawing Sheets

U.S. PATENT DOCUMENTS

| | | | |
|---|---|---|---|
| 4,052,979 A | 10/1977 | Scherr et al. | |
| 4,129,125 A | 12/1978 | Lester et al. | |
| 4,148,304 A | 4/1979 | Mull | |
| 4,151,831 A | 5/1979 | Lester | |
| 4,192,000 A | 3/1980 | Lipsey | |
| 4,312,358 A | 1/1982 | Barney et al. | |
| 4,364,398 A | 12/1982 | Sassi et al. | |
| 4,377,171 A | 3/1983 | Wada | |
| 4,407,295 A | 10/1983 | Steuer et al. | |
| 4,488,558 A | 12/1984 | Simbruner et al. | |
| 4,509,531 A | 4/1985 | Ward | |
| 4,531,527 A | 7/1985 | Reinhold, Jr. et al. | |
| 4,539,994 A | 9/1985 | Baumbach et al. | |
| 4,557,273 A | 12/1985 | Stoller et al. | |
| 4,608,987 A | 9/1986 | Mills | |
| 4,622,979 A | 11/1986 | Katchis et al. | |
| 4,627,738 A | 12/1986 | Kao | |
| 4,672,977 A | 6/1987 | Kroll | |
| 4,676,254 A | 6/1987 | Frohn | |
| 4,757,453 A | 7/1988 | Nasiff | |
| RE32,758 E | 10/1988 | Zartman | |
| 4,784,162 A | 11/1988 | Ricks et al. | |
| 4,803,625 A | 2/1989 | Fu et al. | |
| 4,819,860 A | 4/1989 | Hargrove et al. | |
| 4,827,943 A | 5/1989 | Bornn et al. | |
| 4,828,257 A | 5/1989 | Dyer et al. | |
| 4,883,063 A | 11/1989 | Bernard et al. | |
| 4,891,756 A | 1/1990 | Williams, III | |
| 4,917,108 A | 4/1990 | Mault | |
| 4,951,197 A * | 8/1990 | Mellinger | 600/300 |
| 4,958,645 A | 9/1990 | Cadell et al. | |
| 4,966,154 A | 10/1990 | Cooper et al. | |
| 4,981,139 A | 1/1991 | Pfohl | |
| 5,007,427 A | 4/1991 | Suzuki et al. | |
| 5,012,411 A | 4/1991 | Policastro | |
| 5,027,824 A | 7/1991 | Dougherty et al. | |
| 5,038,792 A | 8/1991 | Mault | |
| 5,040,541 A | 8/1991 | Poppendiek | |
| 5,050,612 A | 9/1991 | Matsumura | |
| 5,072,458 A | 12/1991 | Suzuki | |
| 5,111,818 A | 5/1992 | Suzuki et al. | |
| 5,135,311 A | 8/1992 | Alpert | |
| 5,148,002 A | 9/1992 | Kuo et al. | |
| 5,178,155 A | 1/1993 | Mault | |
| 5,179,958 A | 1/1993 | Mault | |
| 5,216,599 A | 6/1993 | Uebe et al. | |
| 5,224,479 A | 7/1993 | Sekine | |
| 5,263,491 A | 11/1993 | Thornton | |
| 5,285,398 A | 2/1994 | Janik | |
| 5,305,244 A | 4/1994 | Newman et al. | |
| 5,335,664 A | 8/1994 | Nagashima | |
| 5,353,793 A | 10/1994 | Bornn | |
| 5,410,471 A | 4/1995 | Alyfuku et al. | |
| 5,435,315 A | 7/1995 | McPhee et al. | |
| 5,445,149 A | 8/1995 | Rotolo et al. | |
| 5,458,123 A | 10/1995 | Unger | |
| 5,469,861 A | 11/1995 | Piscopo et al. | |
| 5,474,090 A | 12/1995 | Begun et al. | |
| 5,476,103 A | 12/1995 | Nashner | |
| 5,484,389 A | 1/1996 | Stark et al. | |
| 5,491,651 A | 2/1996 | Janik | |
| 5,511,553 A | 4/1996 | Segalowitz | |
| 5,515,858 A | 5/1996 | Myllymaki | |
| 5,515,865 A | 5/1996 | Scanlon | |
| 5,523,730 A | 6/1996 | Van Zeeland | |
| 5,524,618 A | 6/1996 | Pottgen et al. | |
| 5,555,490 A | 9/1996 | Carroll | |
| 5,559,497 A | 9/1996 | Hong | |
| 5,564,429 A | 10/1996 | Bornn et al. | |
| 5,566,679 A | 10/1996 | Herriott | |
| 5,581,238 A | 12/1996 | Chang et al. | |
| 5,581,492 A | 12/1996 | Janik | |
| 5,583,758 A | 12/1996 | McIlroy et al. | |
| 5,611,085 A | 3/1997 | Rasmussen | |
| 5,617,477 A | 4/1997 | Boyden | |
| 5,622,180 A | 4/1997 | Tammi et al. | |
| 5,645,068 A | 7/1997 | Mezack et al. | |
| 5,652,570 A | 7/1997 | Lepkofker | |
| 5,663,703 A | 9/1997 | Pearlman et al. | |
| 5,666,096 A | 9/1997 | Van Zeeland | |
| 5,670,944 A | 9/1997 | Myllymaki | |
| 5,673,691 A * | 10/1997 | Abrams et al. | 600/300 |
| 5,673,692 A | 10/1997 | Schulze et al. | |
| 5,686,516 A | 11/1997 | Tzur | |
| 5,687,734 A | 11/1997 | Dempsey et al. | |
| 5,697,791 A | 12/1997 | Nashner et al. | |
| 5,704,350 A | 1/1998 | Williams, III | |
| 5,719,743 A | 2/1998 | Jenkins et al. | |
| 5,724,025 A | 3/1998 | Tavori | |
| 5,726,631 A | 3/1998 | Lin | |
| 5,729,203 A | 3/1998 | Oka et al. | |
| 5,729,479 A * | 3/1998 | Golan | 708/132 |
| 5,730,140 A | 3/1998 | Fitch | |
| 5,738,104 A | 4/1998 | Lo et al. | |
| 5,741,217 A | 4/1998 | Gero | |
| 5,752,976 A | 5/1998 | Duffin et al. | |
| 5,771,001 A | 6/1998 | Cobb | |
| 5,778,882 A | 7/1998 | Raymond et al. | |
| 5,798,907 A | 8/1998 | Janik | |
| 5,803,915 A | 9/1998 | Kremenchugsky et al. | |
| 5,813,766 A | 9/1998 | Chen | |
| 5,813,994 A | 9/1998 | Pottgen et al. | |
| 5,823,975 A | 10/1998 | Stark et al. | |
| 5,827,180 A | 10/1998 | Goodman | |
| 5,828,943 A | 10/1998 | Brown | |
| 5,832,296 A | 11/1998 | Wang et al. | |
| 5,832,448 A | 11/1998 | Brown | |
| 5,836,300 A | 11/1998 | Mault | |
| 5,839,901 A * | 11/1998 | Karkanen | 434/127 |
| 5,853,005 A | 12/1998 | Scanlon | |
| 5,855,550 A | 1/1999 | Lai et al. | |
| 5,857,939 A | 1/1999 | Kaufman | |
| 5,857,967 A | 1/1999 | Frid et al. | |
| 5,862,803 A | 1/1999 | Besson et al. | |
| 5,865,733 A | 2/1999 | Malinouskas et al. | |
| 5,868,669 A | 2/1999 | Iliff | |
| 5,868,671 A | 2/1999 | Mahoney | |
| 5,871,451 A | 2/1999 | Unger et al. | |
| 5,876,350 A | 3/1999 | Lo et al. | |
| 5,879,163 A | 3/1999 | Brown et al. | |
| 5,879,309 A | 3/1999 | Johnson et al. | |
| 5,884,198 A | 3/1999 | Kese et al. | |
| 5,888,172 A | 3/1999 | Andrus et al. | |
| 5,897,493 A | 4/1999 | Brown | |
| 5,899,855 A | 5/1999 | Brown | |
| 5,902,250 A | 5/1999 | Verrier et al. | |
| 5,908,396 A | 6/1999 | Hayakawa et al. | |
| 5,912,865 A | 6/1999 | Ortega | |
| 5,913,310 A | 6/1999 | Brown | |
| 5,919,141 A | 7/1999 | Money et al. | |
| 5,929,782 A | 7/1999 | Stark et al. | |
| 5,931,791 A | 8/1999 | Saltzstein et al. | |
| 5,933,136 A | 8/1999 | Brown | |
| 5,941,837 A | 8/1999 | Amano et al. | |
| 5,951,300 A | 9/1999 | Brown | |
| 5,954,510 A * | 9/1999 | Merrill et al. | 434/236 |
| 5,956,501 A | 9/1999 | Brown | |
| 5,957,854 A | 9/1999 | Besson et al. | |
| 5,959,611 A | 9/1999 | Smailagic et al. | |
| 5,960,380 A | 9/1999 | Flentov et al. | |
| 5,960,403 A | 9/1999 | Brown | |
| 5,976,083 A | 11/1999 | Richardson et al. | |
| 5,989,157 A | 11/1999 | Walton et al. | |
| 5,990,772 A | 11/1999 | Van Zeeland | |
| 6,013,007 A | 1/2000 | Root et al. | |
| 6,030,342 A | 2/2000 | Amano et al. | |
| 6,032,119 A | 2/2000 | Brown et al. | |
| 6,047,203 A | 4/2000 | Sackner et al. | |
| 6,050,940 A * | 4/2000 | Braun et al. | 600/300 |
| 6,053,872 A | 4/2000 | Mohler | |
| 6,059,692 A | 5/2000 | Hickman | |
| 6,067,468 A | 5/2000 | Korenman et al. | |
| 6,069,552 A | 5/2000 | Van Zeeland | |
| 6,091,973 A | 7/2000 | Colla et al. | |
| 6,095,949 A | 8/2000 | Arai et al. | |
| 6,101,407 A | 8/2000 | Groezinger | |
| 6,101,478 A | 8/2000 | Brown | |

| Patent No. | Date | Inventor |
|---|---|---|
| 6,135,107 A | 10/2000 | Mault |
| 6,138,079 A | 10/2000 | Putman |
| 6,154,668 A | 11/2000 | Pedersen et al. |
| 6,168,563 B1 | 1/2001 | Brown |
| 6,184,797 B1 | 2/2001 | Stark et al. |
| 6,190,314 B1 | 2/2001 | Ark et al. |
| 6,198,394 B1 | 3/2001 | Jacobsen et al. |
| 6,208,900 B1 | 3/2001 | Ecker et al. |
| 6,221,011 B1 | 4/2001 | Bardy |
| 6,225,901 B1 | 5/2001 | Kail, IV |
| 6,225,980 B1 | 5/2001 | Weiss et al. |
| 6,240,323 B1 | 5/2001 | Calenzo et al. |
| 6,247,647 B1 | 6/2001 | Courtney et al. |
| 6,248,065 B1 | 6/2001 | Brown |
| 6,251,048 B1 | 6/2001 | Kaufman |
| 6,254,536 B1 | 7/2001 | DeVito |
| 6,265,978 B1 | 7/2001 | Atlas |
| 6,266,623 B1 | 7/2001 | Vock et al. |
| 6,285,897 B1 | 9/2001 | Kilcoyne et al. |
| 6,287,252 B1 | 9/2001 | Lugo |
| 6,290,646 B1 | 9/2001 | Cosentino et al. |
| 6,290,650 B1 | 9/2001 | Butterfield et al. |
| 6,292,698 B1 | 9/2001 | Duffin et al. |
| 6,298,218 B1 | 10/2001 | Lowe et al. |
| 6,302,844 B1 | 10/2001 | Walker et al. |
| 6,305,071 B1 | 10/2001 | Van Zeeland |
| 6,306,088 B1 | 10/2001 | Krausman et al. |
| 6,312,363 B1 | 11/2001 | Watterson et al. |
| 6,315,719 B1 | 11/2001 | Rode et al. |
| 6,327,495 B1 | 12/2001 | Iwabuchi |
| 6,336,900 B1 | 1/2002 | Alleckson et al. |
| 6,339,720 B1 | 1/2002 | Anzellini et al. |
| 6,341,229 B1 | 1/2002 | Akiva |
| 6,341,295 B1 * | 1/2002 | Stotler ................... 708/131 |
| 6,364,834 B1 | 4/2002 | Reuss et al. |
| 6,366,871 B1 | 4/2002 | Geva |
| 6,368,287 B1 | 4/2002 | Hadas |
| 6,371,123 B1 | 4/2002 | Stark et al. |
| 6,377,162 B1 | 4/2002 | Delestienne et al. |
| 6,385,473 B1 | 5/2002 | Haines et al. |
| 6,392,515 B1 | 5/2002 | Van Zeeland et al. |
| 6,416,471 B1 | 7/2002 | Kumar et al. |
| 6,420,959 B1 | 7/2002 | Lizzi |
| 6,450,922 B1 | 9/2002 | Henderson et al. |
| 6,450,953 B1 | 9/2002 | Place et al. |
| 6,454,708 B1 | 9/2002 | Ferguson et al. |
| 6,466,232 B1 | 10/2002 | Newell et al. |
| 6,468,222 B1 | 10/2002 | Mault et al. |
| 6,478,736 B1 * | 11/2002 | Mault ................... 600/300 |
| 6,494,829 B1 | 12/2002 | New, Jr. et al. |
| 6,513,532 B2 | 2/2003 | Mault et al. |
| 6,516,289 B2 | 2/2003 | David |
| 6,527,711 B1 | 3/2003 | Stivoric et al. |
| 6,532,381 B2 | 3/2003 | Bayer et al. |
| 6,533,731 B2 | 3/2003 | Pottgen et al. |
| 6,539,336 B1 | 3/2003 | Vock et al. |
| 6,547,745 B1 | 4/2003 | Rubinstein et al. |
| 6,551,251 B2 | 4/2003 | Zuckerwar et al. |
| 6,551,252 B2 | 4/2003 | Sackner et al. |
| 6,553,251 B1 | 4/2003 | Lahdesmaki |
| 6,558,320 B1 | 5/2003 | Causey et al. |
| 6,569,094 B2 | 5/2003 | Suzuki |
| 6,571,200 B1 | 5/2003 | Mault |
| 6,579,231 B1 | 6/2003 | Phipps |
| 6,584,344 B2 | 6/2003 | Hannula |
| 6,595,929 B2 | 7/2003 | Stivoric et al. |
| 6,597,944 B1 | 7/2003 | Hadas |
| 6,602,191 B2 | 8/2003 | Quy |
| 6,605,038 B1 | 8/2003 | Teller et al. |
| 6,607,484 B2 | 8/2003 | Suzuki |
| 6,610,012 B2 | 8/2003 | Mault |
| 6,611,206 B2 | 8/2003 | Eshelman et al. |
| 6,611,783 B2 | 8/2003 | Kelly, Jr. et al. |
| 6,616,613 B1 | 9/2003 | Goodman |
| 6,635,015 B2 | 10/2003 | Sagel |
| 6,656,125 B2 | 12/2003 | Misczynski et al. |
| 6,665,559 B2 | 12/2003 | Rowlandson |
| 6,690,959 B2 | 2/2004 | Thompson |
| 6,694,182 B1 | 2/2004 | Yamazaki et al. |
| 6,712,615 B2 | 3/2004 | Martin |
| 6,734,802 B2 | 5/2004 | Halleck et al. |
| 6,755,795 B2 | 6/2004 | Mammarapoulos et al. |
| 6,773,344 B1 | 8/2004 | Gabai et al. |
| 6,790,178 B1 | 9/2004 | Mault et al. |
| 6,808,473 B2 | 10/2004 | Hisano et al. |
| 6,834,436 B2 | 12/2004 | Townsend et al. |
| 6,842,877 B2 | 1/2005 | Robarts et al. |
| 6,852,085 B2 | 2/2005 | Rubinstein |
| 6,874,127 B2 | 3/2005 | Newell et al. |
| 6,920,348 B2 | 7/2005 | Vasin et al. |
| 6,923,324 B2 | 8/2005 | Kanai et al. |
| 6,942,615 B2 | 9/2005 | Suzuki |
| 6,959,259 B2 | 10/2005 | Vock et al. |
| 6,968,375 B1 | 11/2005 | Brown |
| 7,020,508 B2 | 3/2006 | Stivoric et al. |
| 7,073,129 B1 | 7/2006 | Robarts et al. |
| 7,092,846 B2 | 8/2006 | Vock |
| 7,144,151 B2 | 12/2006 | Saaski et al. |
| 7,171,331 B2 | 1/2007 | Vock et al. |
| 7,222,054 B2 | 5/2007 | Geva |
| 7,261,690 B2 | 8/2007 | Teller et al. |
| 7,285,090 B2 | 10/2007 | Stivoric |
| 7,454,002 B1 | 11/2008 | Gardner et al. |
| 7,485,095 B2 | 2/2009 | Shusterman |
| 7,502,643 B2 | 3/2009 | Farringdon |
| 7,689,437 B1 | 3/2010 | Teller et al. |
| 2001/0029340 A1 | 10/2001 | Mault et al. |
| 2001/0032059 A1 | 10/2001 | Kelly, Jr. et al. |
| 2001/0044581 A1 | 11/2001 | Mault |
| 2001/0044588 A1 | 11/2001 | Mault et al. |
| 2001/0049470 A1 | 12/2001 | Mault et al. |
| 2001/0056229 A1 | 12/2001 | Cosentino et al. |
| 2002/0019296 A1 | 2/2002 | Freeman et al. |
| 2002/0019585 A1 | 2/2002 | Dickinson et al. |
| 2002/0019586 A1 | 2/2002 | Teller et al. |
| 2002/0027164 A1 | 3/2002 | Mault |
| 2002/0028995 A1 | 3/2002 | Mault |
| 2002/0032386 A1 | 3/2002 | Sackner et al. |
| 2002/0035340 A1 | 3/2002 | Fraden et al. |
| 2002/0055857 A1 | 5/2002 | Mault et al. |
| 2002/0062069 A1 | 5/2002 | Mault et al. |
| 2002/0107450 A1 | 8/2002 | Ogura |
| 2002/0109600 A1 | 8/2002 | Mault et al. |
| 2002/0111539 A1 | 8/2002 | Cosentino et al. |
| 2002/0128804 A1 | 9/2002 | Geva |
| 2002/0133378 A1 | 9/2002 | Mault et al. |
| 2002/0169634 A1 | 11/2002 | Nishi et al. |
| 2003/0013072 A1 | 1/2003 | Thomas et al. |
| 2003/0055460 A1 | 3/2003 | Owen et al. |
| 2003/0069510 A1 | 4/2003 | Semler |
| 2003/0083559 A1 | 5/2003 | Thompson |
| 2003/0152607 B1 | 8/2003 | Mault |
| 2003/0176797 A1 | 9/2003 | Anzellini |
| 2003/0208113 A1 | 11/2003 | Mault et al. |
| 2004/0039605 A1 | 2/2004 | Bardy et al. |
| 2004/0102931 A1 | 5/2004 | Ellis et al. |
| 2004/0122702 A1 | 6/2004 | Sabol et al. |
| 2004/0133081 A1 | 7/2004 | Teller |
| 2004/0172290 A1 | 9/2004 | Leven et al. |
| 2004/0229685 A1 | 11/2004 | Smith et al. |
| 2004/0230549 A1 | 11/2004 | Freer et al. |
| 2005/0049022 A1 | 3/2005 | Mullen et al. |
| 2005/0070778 A1 | 3/2005 | Lackey et al. |
| 2005/0226310 A1 | 10/2005 | Nakazawa et al. |
| 2005/0245839 A1 | 11/2005 | Stivoric |
| 2006/0031102 A1 | 2/2006 | Teller et al. |
| 2006/0122474 A1 | 6/2006 | Teller et al. |
| 2006/0264730 A1 | 11/2006 | Stivoric et al. |
| 2007/0173705 A1 | 7/2007 | Teller et al. |

FOREIGN PATENT DOCUMENTS

| | | |
|---|---|---|
| CH | 00579798 | 9/1976 |
| DE | 19832361 A1 | 2/2000 |
| DE | 19911766 A1 | 9/2000 |
| EP | 0670064 B1 | 11/1993 |
| EP | 0707825 A2 | 4/1996 |
| EP | 0880936 A3 | 3/1999 |
| GB | 2203250 | 10/1988 |

| | | | |
|---|---|---|---|
| GB | 2322952 A | 5/1997 | |
| JP | 4341243 | 11/1972 | |
| JP | 09056705 | 3/1997 | |
| JP | 10118052 | 5/1998 | |
| JP | 10295651 | 11/1998 | |
| JP | 10305016 | 11/1998 | |
| JP | 10305072 | 11/1998 | |
| JP | 2000-083935 | 3/2000 | |
| JP | 2002095637 | 4/2002 | |
| KR | 200244874 | 11/2001 | |
| WO | 93/01574 | 1/1993 | |
| WO | 94/25841 | 11/1994 | |
| WO | 9525946 | 9/1995 | |
| WO | 97/06499 | 2/1997 | |
| WO | 97/47239 | 12/1997 | |
| WO | 98/50873 | 11/1998 | |
| WO | 99/27483 | 11/1998 | |
| WO | 9859227 | 12/1998 | |
| WO | 99/44494 | 9/1999 | |
| WO | 00/11578 | 3/2000 | |
| WO | 00/52604 | 3/2000 | |
| WO | 00/26882 | 5/2000 | |
| WO | 00/32098 | 6/2000 | |
| WO | 00/47108 | 8/2000 | |
| WO | 00/51543 | 9/2000 | |
| WO | WO 00/52604 | * | 9/2000 |
| WO | 01/52718 | 1/2001 | |
| WO | 0101093 | 1/2001 | |
| WO | 01/08554 | 2/2001 | |
| WO | 01/56454 | 2/2001 | |
| WO | 01/26535 | 4/2001 | |
| WO | 01/26547 | 4/2001 | |
| WO | 01/28416 | 4/2001 | |
| WO | 01/28495 | 4/2001 | |
| WO | 01/82783 | 4/2001 | |
| WO | 01/39089 | 5/2001 | |
| WO | 01/82789 | 5/2001 | |
| WO | 01/89365 A2 | 5/2001 | |
| WO | 01/89365 A3 | 5/2001 | |
| WO | 01/89368 A2 | 5/2001 | |
| WO | 01/89368 A3 | 5/2001 | |
| WO | 01/41645 | 6/2001 | |
| WO | 0196986 | 12/2001 | |
| WO | 02/051308 | 7/2002 | |
| WO | 02/069798 A1 | 9/2002 | |
| WO | 02093272 | 11/2002 | |
| WO | 03/015005 | 2/2003 | |
| WO | 2005/046433 | 5/2005 | |

OTHER PUBLICATIONS

Therm-A-Gap, Chomerics Technical Bulletin 70, Feb. 6, 2001.
CoolPoly, the Original Thermally Conductive Polymer, Feb. 7, 2001 (article downloaded from www.coolpolymers.com).
Micro-Foil Heat Flux Sensors, RdF Corporation Catalog No. HFS-A, Mar. 1998.
Industrial Micro-Foil Heat Flux Sensor, RdF Corporation Datasheet No. HFS-B, Oct. 1995.
Industrial/Commercial Micro-Foil Heat Flux Sensor, RdF Corporation Catalong No. HFS-C, Dec. 1999.
"A combined heart rate and movement sensor: proof of concept and preliminary testing study," K. Rennie, T. Rowsell, S.A. Jebb, D. Holburn & N. J. Wareham, 2000.
"Ironman Speed and Distance System" (downloaded from www.timex.com), Timex, Oct. 4, 2002.
"Ironman Speed Distance System—Once Again Timex Revolutionizes the Sportwatch" (downloaded from www.timex.com), Timex, Jan. 8, 2002.
Polar M91ti Heart Rate Monitor Users Manual—Quick Guide, Polar Electro Inc., Nov. 2000.
Polar USA—Product Detail—M91ti (downloaded from www.polarusa.com), Polar USA, Oct. 4, 2002.
Polar USA—Product Detail—S-610 (downloaded from www.polarusa.com), Polar USA, Oct. 4, 2002.
Georgia Tech "Smart T-Shirt", Georgia Institute of Technology Press Release, Nov. 14, 1997.
"Personal Health Monitor for Homes," Timo Tuomisto & Vesa Pentikainen, ERCIM News, No. 29, Apr. 1997.
CYBeR-Care Internet Healthcare Technologies, BW Health Wire, Oct. 7, 1999.
"Nearer to the Heart," Brianna Krebs, Washington Post, Jan. 17, 1999.
"Portable Sensor Provides Remote Monitoring of Heart," Nikkei Weekly, Oct. 27, 1998.
"FDA Clears Datex-Ohmeda Pulse Oximeter," BW Health Wire, Dec. 3, 1998.
Estee Soft New Version of Life Connect, Business Wire, Jan. 20, 1999.
Matsushita Home Health Check System, The Nihon Keizai Shimbun, Dec. 17, 1998.
Lightweight Ambulatory Physiological Monitoring System, Ames Research Center, Moffett Field, CA, May 22, 2002.
Warfighter Physiological Status Monitoring, MOMRP Fact Sheet No. 6, USAMRMC, 1999 (downloaded from www.momrp.org).
The H.J. Andrews Climatological Field Measurement Program, D. Henshaw, Aug. 8, 1997 (downloaded from www.fsl.orst.edu).
Weight Watchers TurnAround, Weight Watchers, 2004, (downloaded from www.weightwatchers.com).
Weight Loss Programs, Jenny Craig, 2004 (downloaded from www.jennycraig.com).
The Complete Nutrition & Weight Management Solution Based on Your Unique Metabolic Fingerprint & Goals, BalanceLog, 2004 (downloaded from www.healthetech.com).
What is FitDay?, FitDay, 2004 (downloaded from www.fitday.com).
European Search Report, EP11159897, search mailed Aug. 2, 2011, 4 pages.

* cited by examiner

SYSTEM FOR MONITORING AND MANAGING BODY WEIGHT AND OTHER PHYSIOLOGICAL CONDITIONS INCLUDING ITERATIVE AND PERSONALIZED PLANNING, INTERVENTION AND REPORTING CAPABILITY

CROSS REFERENCE TO RELATED APPLICATIONS

This application is a continuation in part of U.S. application Ser. No. 10/638,588, filed Aug. 11, 2003, now U.S. Pat. No. 6,605,038 which is a continuation of U.S. application Ser. No. 09/602,537, filed Jun. 23, 2000, now U.S. Pat. No. 7,689, 437 which is a continuation-in-part of U.S. application Ser. No. 09/595,660, filed Jun. 16, 2000. This application also claims the benefit of U.S. Provisional Application No. 60/502,764 filed on Sep. 13, 2003 and U.S. Provisional Application No. 50/555,280 filed on Mar. 22, 2004.

FIELD OF THE INVENTION

The present invention relates to a weight control system. More specifically, the system may be used as part of a behavioral modification program for calorie control, weight control or general fitness. In particular, the invention, according to one aspect, relates to an apparatus used in conjunction with a software platform for monitoring caloric consumption and/or caloric expenditure of an individual. Additionally, the invention relates to a method of tracking progress toward weight goals.

BACKGROUND OF THE INVENTION

Research has shown that a large number of the top health problems in society are either caused in whole or in part by an unhealthy lifestyle. More and more, our society requires people to lead fast-paced, achievement-oriented lifestyles that often result in poor eating habits, high stress levels, lack of exercise, poor sleep habits and the inability to find the time to center the mind and relax. Additionally, obesity and body weight have become epidemic problems facing a large segment of the population, notably including children and adolescents. Recognizing this fact, people are becoming increasingly interested in establishing a healthier lifestyle.

Traditional medicine, embodied in the form of an HMO or similar organization, does not have the time, the training, or the reimbursement mechanism to address the needs of those individuals interested in a healthier lifestyle. There have been several attempts to meet the needs of these individuals, including a perfusion of fitness programs and exercise equipment, dietary plans, self-help books, alternative therapies, and most recently, a plethora of health information web sites on the Internet. Each of these attempts is targeted to empower the individual to take charge and get healthy. Each of these attempts, however, addresses only part of the needs of individuals seeking a healthier lifestyle and ignores many of the real barriers that most individuals face when trying to adopt a healthier lifestyle. These barriers include the fact that the individual is often left to himself or herself to find motivation, to implement a plan for achieving a healthier lifestyle, to monitor progress, and to brainstorm solutions when problems arise; the fact that existing programs are directed to only certain aspects of a healthier lifestyle, and rarely come as a complete package; and the fact that recommendations are often not targeted to the unique characteristics of the individual or his life circumstances.

With respect to weight loss, specifically, many medical and other commercial methodologies have been developed to assist individuals in losing excess body weight and maintaining an appropriate weight level through various diet, exercise and behavioral modification techniques. Weight Watchers is an example of a weight loss behavior modification system in which an individual manages weight loss with a points system utilizing commercially available foods. All food items are assigned a certain number of points based on serving size and content of fat, fiber and calories. Foods that are high in fat are assigned a higher number of points. Foods that are high in fiber receive a lower number of points. Healthier foods are typically assigned a lower number of points, so the user is encouraged to eat these food items.

A user is assigned a daily points range which represents the total amount of food the user should consume within each day. Instead of directing the user away from a list of forbidden foods, a user is encouraged to enjoy all foods in moderation, as long as they fit within a user's points budget. The program is based on calorie reduction, portion control and modification of current eating habits. Exercise activities are also assigned points which are subtracted from the points accumulated by a user's daily caloric intake.

Weight Watchers attempts to make a user create a balance of exercise and healthy eating in their life. However, because only caloric value of food is specifically tracked, the program tends to fail in teaching the user about the nutritional changes they need to make to maintain weight loss. Calorie content is not the only measurement that a user should take into control when determining what food items to consume. Items that contain the same caloric content may not be nutritiously similar. So, instead of developing healthy eating habits, a user might become dependent on counting points. It is important to note that the Weight Watchers program deals essentially with caloric intake only and not caloric expenditure.

Similarly, Jenny Craig is also a weight loss program. Typically, an individual is assigned a personal consultant who monitors weight loss progress. In addition, the individual will receive pre-selected menus which are based on the Food Guide Pyramid for balanced nutrition. The menus contain Jenny Craig branded food items which are shipped to the individual's home or any other location chosen by the individual. The Jenny Craig program teaches portion control because the food items to be consumed are pre-portioned and supplied by Jenny Craig. However, such a close dietary supervision can be a problem once the diet ends because the diet plan does not teach new eating habits or the value of exercise. Instead it focuses mainly on short term weight loss goals.

The integration of computer and diet tracking systems has created several new and more automated approaches to weight loss. Available methodologies can be tailored to meet the individual's specific physiological characteristics and weight loss goals.

BalanceLog, developed by HealtheTech, Inc. and the subject of U.S. Published Application No. 20020133378 is a software program that provides a system for daily tracking and monitoring of caloric intake and expenditure. The user customizes the program based on metabolism in addition to weight and nutrition goals. The user is able to create both exercise and nutrition plans in addition to tracking progress. However, the BalanceLog system has several limitations.

First, a user must know their resting metabolic rate, which is the number of calories burned at rest. The user can measure their resting metabolic rate. However, a more accurate rate can be measured by appointment at a metabolism measurement location. A typical individual, especially an individual who is beginning a weight and nutrition management plan may view this requirement as an inconvenience. The system can provide an estimated resting metabolic rate based on a broad population average if a more accurate measurement cannot be made. However, the resting metabolic rate can vary widely between individuals having similar physiological characteristics. Thus, an estimation may not be accurate and would affect future projections of an individual's progress.

Second, the system is limited by the interactivity and compliance of the user. Every aspect of the BalanceLog system is manual. Every item a user eats and every exercise a user does must be logged in the system. If a user fails to do this, the reported progress will not be accurate. This manual data entry required by BalanceLog assumes that the user will be in close proximity to a data entry device, such as a personal digital assistant or a personal computer, to enter daily activities and consumed meals. However, a user may not consistently or reliably be near their data entry device shortly thereafter engaging in an exercise or eating activity. They may be performing the exercise activity at a fitness center or otherwise away from such a device. Similarly, a user may not be eating a certain meal at home, so they may not be able to log the information immediately after consuming the meal. Therefore, a user must maintain a record of all food consumed and activities performed so that these items can be entered into the BalanceLog system at a later time.

Also, the BalanceLog system does not provide for the possibility of estimation. A user must select the food consumed and the corresponding portion size of the food item. If a time lapse has occurred between the meal and the time of entry and the user does not remember the meal, the data may not be entered accurately and the system would suffer from a lack of accuracy. Similarly, if a user does not remember the details of an exercise activity, the data may not be correct.

Finally, the BalanceLog system calculates energy expenditure based only upon the information entered by the user. A user may only log an exercise activity such as running on a treadmill for thirty minutes for a particular day. This logging process does not take into account the actual energy expenditure of the individual, but instead relies on averages or look-up tables based upon general population data, which may not be particularly accurate for any specific individual.

The program also ignores the daily activities of the user such as walking up stairs or running to catch the bus. These daily activities need to be taken into account for a user to accurately determine their total amount of energy expenditure.

Similarly FitDay, a software product developed by Cyser Software, is another system that allows a user to track both nutrition and exercise activity to plan weight loss and monitor progress.

The FitDay software aids a user in controlling diet through the input of food items consumed. This software also tracks the exercise activity and caloric expenditure through the manual data entry by the user. The FitDay software also enables the user to track and graph body measurements for additional motivation to engage in exercise activity. Also, FitDay also focuses on another aspect of weight loss. The system prompts a user for information regarding daily emotions for analysis of the triggers that may affect a user's weight loss progress.

FitDay suffers from the same limitations of Balance Log. FitDay is dependent upon user input for its calculations and weight loss progress analysis. As a result, the information may suffer from a lack of accuracy or compliance because the user might not enter a meal or an activity. Also, the analysis of energy expenditure is dependent on the input of the user and does not take the daily activities of the user into consideration.

Overall, if an individual consumes fewer calories than the number of calories burned, they user should experience a net weight loss. While the methods described above offer a plurality of ways to count consumed calories, they do not offer an efficient way to determine the caloric expenditure. Additionally, they are highly dependent upon compliance with rigorous data entry requirements. Therefore, what is lacking in the art is a management system that can accurately and automatically monitor daily activity and energy expenditure of the user to reduce the need for strict compliance with and the repetitive nature of manual data entry of information.

SUMMARY OF THE INVENTION

A nutrition and activity management system is disclosed that can help an individual meet weight loss goals and achieve an optimum energy balance of calories burned versus calories consumed. The system may be automated and is also adaptable or applicable to measuring a number of other physiological parameters and reporting the same and derivations of such parameters. The preferred embodiment, a weight management system, is directed to achieving an optimum energy balance, which is essential to progressing toward weight loss-specific goals. Most programs, such as the programs discussed above, offer methods of calorie and food consumption tracking, but that is only half of the equation. Without an accurate estimation of energy expenditure, the optimum energy balance cannot be reached. In other embodiments, the system may provide additional or substitute information regarding limits on physical activity, such as for a pregnant or rehabilitating user, or physiological data, such as blood sugar level, for a diabetic.

The management system that is disclosed provides a more accurate estimation of the total energy expenditure of the user. The other programs discussed above can only track energy expenditure through manual input of the user regarding specific physical activity of a certain duration. The management system utilizes an apparatus on the body that continuously monitors the heat given off by a user's body in addition to motion, skin temperature and conductivity. Because the apparatus is continuously worn, data is collected during any physical activity performed by the user, including exercise activity and daily life activity. The apparatus is further designed for comfort and convenience so that long term wear is not unreasonable within a wearer's lifestyle activities. It is to be specifically noted that the apparatus is designed for both continuous and long term wear. Continuous is intended to mean, however, nearly continuous, as the device may be removed for brief periods for hygienic purposes or other de minimus non-use. Long term wear is considered to be for a substantial portion of each day of wear, typically extending beyond a single day. The data collected by the apparatus is uploaded to the software platform for determining the number of calories burned, the number of steps taken and the duration of physical activity.

The management system that is disclosed also provides an easier process for the entry and tracking of caloric consumption. The tracking of caloric consumption provided by the management system is based on the recognition that current manual nutrition tracking methods are too time consuming and difficult to use, which ultimately leads to a low level of compliance, inaccuracy in data collection and a higher percentage of false caloric intake estimates. Most users are too busy to log everything they eat for each meal and tend to forget how much they ate. Therefore, in addition to manual input of consumed food items, the user may select one of several other methods of caloric input which may include an estimation for a certain meal based upon an average for that meal, duplication of a previous meal and a quick caloric estimate tool. A user is guided through the complex task of recalling what they ate in order to increase compliance and reduce the discrepancy between self-reported and actual caloric intake.

The combination of the information collected from the apparatus and the information entered by the user is used to provide feedback information regarding the user's progress and recommendations for reaching dietary goals. Because of the accuracy of the information, the user can proactively make lifestyle changes to meet weight loss goals, such as adjusting diet or exercising to burn more calories. The system can also predict data indicative of human physiological parameters including energy expenditure and caloric intake for any given relevant time period as well as other detected and derived physiological or contextual information. The user may then be notified as to their actual or predicted progress with respect to the optimum energy balance or other goals for the day.

An apparatus is disclosed for monitoring certain identified human status parameters which includes at least one sensor adapted to be worn on an individual's body. A preferred embodiment utilizes a combination of sensors to provide more accurately sensed data, with the output of the multiple sensors being utilized in the derivation of additional data. The sensor or sensors utilized by the apparatus may include a physiological sensor selected from the group consisting of respiration sensors, temperature sensors, heat flux sensors, body conductance sensors, body resistance sensors, body potential sensors, brain activity sensors, blood pressure sensors, body impedance sensors, body motion sensors, oxygen consumption sensors, body chemistry sensors, body position sensors, body pressure sensors, light absorption sensors, body sound sensors, piezoelectric sensors, electrochemical sensors, strain gauges, and optical sensors. The sensor or sensors are adapted to generate data indicative of at least a first parameter of the individual and a second parameter of the individual, wherein the first parameter is a physiological parameter. The apparatus also includes a processor that receives at least a portion of the data indicative of the first parameter and the second parameter. The processor is adapted to generate derived data from at least a portion of the data indicative of a first parameter and a second parameter, wherein the derived data comprises a third parameter of the individual. The third parameter is an individual status parameter that cannot be directly detected by the at least one sensor.

In an alternate embodiment, the apparatus for monitoring human status parameters is disclosed that includes at least two sensors adapted to be worn on an individual's body selected from the group consisting of physiological sensors and contextual sensors, wherein at least one of the sensors is a physiological sensor. The sensors are adapted to generate data indicative of at least a first parameter of the individual and a second parameter of the individual, wherein the first parameter is physiological. The apparatus also includes a processor for receiving at least a portion of the data indicative of at least a first parameter and a second parameter, the processor being adapted to generate derived data from the data indicative of at least a first parameter and a second parameter. The derived data comprises a third parameter of the individual, for example one selected from the group consisting of ovulation state, sleep state, calories burned, basal metabolic rate, basal temperature, physical activity level, stress level, relaxation level, oxygen consumption rate, rise time, time in zone, recovery time, and nutrition activity. The third parameter is an individual status parameter that cannot be directly detected by any of the at least two sensors.

In either embodiment of the apparatus, the at least two sensors may be both physiological sensors, or may be one physiological sensor and one contextual sensor. The apparatus may further include a housing adapted to be worn on the individual's body, wherein the housing supports the sensors or wherein at least one of the sensors is separately located from the housing. The apparatus may further include a flexible body supporting the housing having first and second members that are adapted to wrap around a portion of the individual's body. The flexible body may support one or more of the sensors. The apparatus may further include wrapping means coupled to the housing for maintaining contact between the housing and the individual's body, and the wrapping means may support one or more of the sensors.

Either embodiment of the apparatus may further include a central monitoring unit remote from the at least two sensors that includes a data storage device. The data storage device receives the derived data from the processor and retrievably stores the derived data therein. The apparatus also includes means for transmitting information based on the derived data from the central monitoring unit to a recipient, which recipient may include the individual or a third party authorized by the individual. The processor may be supported by a housing adapted to be worn on the individual's body, or alternatively may be part of the central monitoring unit.

A weight-loss directed software program is disclosed that automates the tracking of the energy expenditure of the individual through the use of the apparatus and reduces the repetitive nature of data entry in the determination of caloric consumption in addition to providing relevant feedback regarding the user's weight loss goals. The software program is based on the energy balance equation which has two components: energy intake and energy expenditure. The difference between these two values is the energy balance. When this value is negative, a weight loss should be achieved because fewer calories were consumed than expended. A positive energy balance will most likely result in no loss of weight or a weight gain.

The weight-loss directed software program may include an energy intake tracking subsystem, an energy expenditure tracking subsystem, a weight tracking subsystem and an energy balance and feedback subsystem.

The energy intake tracking subsystem preferably incorporates a food database which includes an extensive list of commonly consumed foods, common branded foods available at regional and national food chains, and branded off the shelf entrees and the nutrient information for each item. The user also has the capability to enter custom preparations or recipes which then become a part of the food in the database.

The energy expenditure subsystem includes a data retrieval process to retrieve the data from the apparatus. The system uses the data collected by the apparatus to determine total energy expenditure. The user has the option of manually entering data for an activity engaged in during a time when the apparatus was not available. The system is further provided with the ability to track and recognize certain activity or nutritional intake parameters or patterns and automatically provide such identification to the user on a menu for selection, as disclosed in copending U.S. patent application Ser. No. 10/682,293, the disclosure of which is incorporated by reference. Additionally, the system may directly adopt such identified activities or nutritional information without input from the user, as appropriate.

The energy balance and feedback subsystem provides feedback on behavioral strategies to achieve energy balance proactively. A feedback and coaching engine analyzes the data generated by the system to provide the user with a variety of choices depending on the progress of the user.

A management system is disclosed which includes an apparatus that continuously monitors a user's energy expenditure and a software platform for the manual input of information by the user regarding physical activity and calories consumed. This manual input may be achieved by the user entering their own food, by a second party entering the food for them such as an assistant in a assisted living situation, or through a second party receiving the information from the user via voice, phone, or other transmission mechanism. Alternatively, the food intake can be automatically gathered through either a monitoring system that captures what food is removed from an storage appliance such as a refrigerator or inserted into a food preparation appliance such as an oven or through a derived measure from one or more physiological parameters.

The system may be further adapted to obtain life activities data of the individual, wherein the information transmitted from the central monitoring unit is also based on the life activities data. The central monitoring unit may also be adapted to generate and provide feedback relating to the degree to which the individual has followed a suggested routine. The feedback may be generated from at least a portion of at least one of the data indicative of at least a first parameter and a second parameter, the derived data and the life activities data. The central monitoring unit may also be adapted to generate and provide feedback to a recipient relating to management of an aspect of at least one of the individual's health and lifestyle. This feedback may be generated from at least one of the data indicative of a first parameter, the data indicative of a second parameter and the derived data. The feedback may include suggestions for modifying the individual's behavior.

The system may be further adapted to include a weight and body fat composition tracking subsystem to interpret data received from: manual input, a second device such as a transceiver enabled weight measuring device, or data collected by the apparatus.

The system may also be further adapted to include a meal planning subsystem that allows a user to customize a meal plan based on individual fitness and weight loss goals. Appropriate foods are recommended to the user based on answers provided to general and medical questionnaires. These questionnaires are used as inputs to the meal plan generation system to ensure that foods are selected that take into consideration specific health conditions or preferences of the user. The system may be provided with functionality to recommend substitution choices based on the food category and exchange values of the food and will match the caloric content between substitutions. The system may be further adapted to generate a list of food or diet supplement intake recommendations based on answers provided by the user to a questionnaire.

The system may also provide the option for the user to save or print a report of summary data. The summary data could provide detailed information about the daily energy intake, daily energy expenditure, weight changes, body fat composition changes and nutrient information if the user has been consistently logging the foods consumed. Reports containing information for a certain time period, such as 7 days, 30 days, 90 days and from the beginning of the system usage may also be provided.

The system may also include an exercise planning subsystem that provides recommendations to the user for cardiovascular and resistance training. The recommendations could be based on the fitness goals submitted by the questionnaire to the system.

The system may also provide feedback to the user in the form of a periodic or intermittent status report. The status report may be an alert located in a box on a location of the screen and is typically set off to attract the user's attention. Status reports and images are generated by creating a key string based on the user's current view and state and may provide information to the user about their weight loss goal progress. This information may include suggestions to meet the user's calorie balance goal for the day.

Although this description addresses weight loss with specificity, it should be understood that this system may also be equally applicable to weight maintenance or weight gain.

BRIEF DESCRIPTION OF THE DRAWINGS

Further features and advantages of the present invention will be apparent upon consideration of the following detailed description of the present invention, taken in conjunction with the following drawings, in which like reference characters refer to like parts, and in which.

DESCRIPTION OF THE PREFERRED EMBODIMENTS

Figure 1:
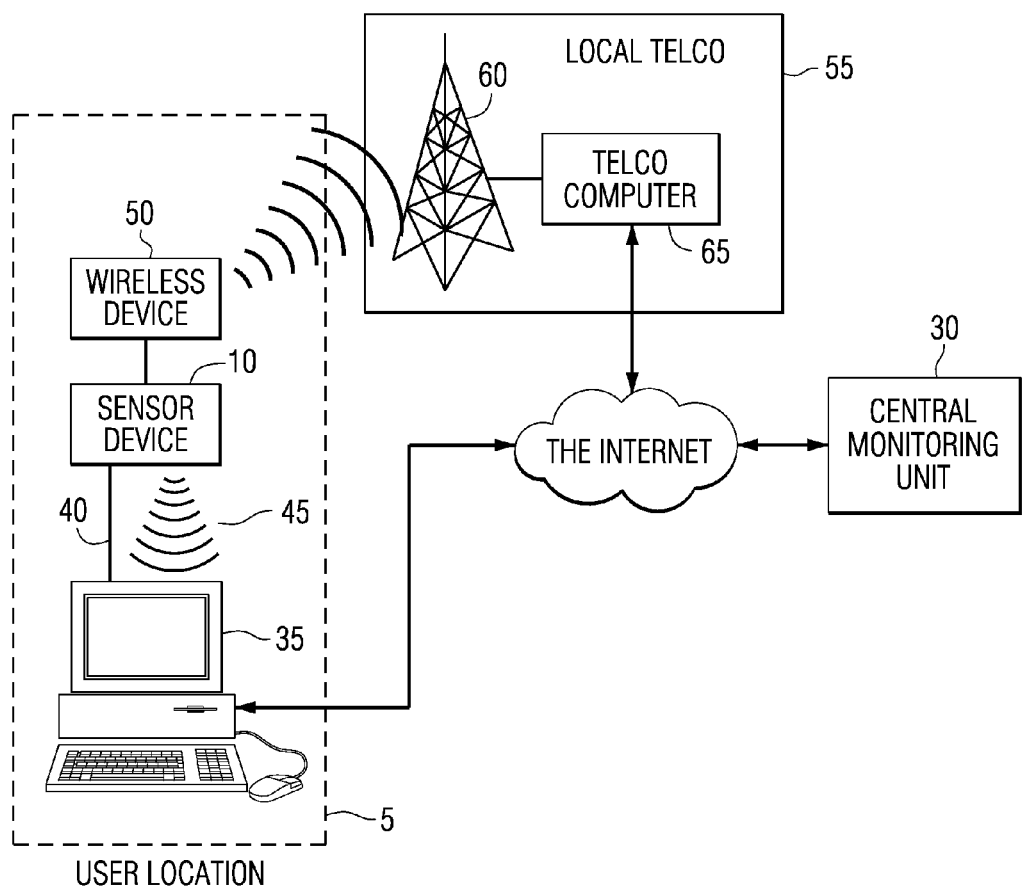
FIG. 1 is a diagram of an embodiment of a system for monitoring physiological data and lifestyle over an electronic network according to the present invention.

In general, according to the present invention, data relating to the physiological state, the lifestyle and certain contextual parameters of an individual is collected and transmitted, either subsequently or in real-time, to a site, preferably remote from the individual, where it is stored for later manipulation and presentation to a recipient, preferably over an electronic network such as the Internet. Contextual parameters as used herein means parameters relating to activity state or to the environment, surroundings and location of the individual, including, but not limited to, air quality, sound quality, ambient temperature, global positioning and the like. Referring to FIG.1, located at user location 5 is sensor device 10 adapted to be placed in proximity with at least a portion of the human body. Sensor device 10 is preferably worn by an individual user on his or her body, for example as part of a garment such as a form fitting shirt, or as part of an arm band or the like. Sensor device 10, includes one or more sensors, which are adapted to generate signals in response to physiological characteristics of an individual, and a microprocessor. Proximity as used herein means that the sensors of sensor device 10 are separated from the individual's body by a material or the like, or a distance such that the capabilities of the sensors are not impeded.

Sensor device 10 generates data indicative of various physiological parameters of an individual, such as the individual's heart rate, pulse rate, beat-to-beat heart variability, EKG or ECG, respiration rate, skin temperature, core body temperature, heat flow off the body, galvanic skin response or GSR, EMG, EEG, EOG, blood pressure, body fat, hydration level, activity level, oxygen consumption, glucose or blood sugar level, body position, pressure on muscles or bones, and UV radiation exposure and absorption. In certain cases, the data indicative of the various physiological parameters is the signal or signals themselves generated by the one or more sensors and in certain other cases the data is calculated by the microprocessor based on the signal or signals generated by the one or more sensors. Methods for generating data indicative of various physiological parameters and sensors to be used therefor are well known. Table 1 provides several examples of such well known methods and shows the parameter in question, an example method used, an example sensor device used, and the signal that is generated. Table 1 also provides an indication as to whether further processing based on the generated signal is required to generate the data.

TABLE 1

| Parameter | Example Method | Example Sensor | Signal | Further Processing |
|---|---|---|---|---|
| Heart Rate | EKG | 2 Electrodes | DC Voltage | Yes |
| Pulse Rate | BVP | LED Emitter and Optical Sensor | Change in Resistance | Yes |
| Beat-to-Beat Variability | Heart Beats | 2 Electrodes | DC Voltage | Yes |
| EKG | Skin Surface Potentials | 3–10 Electrodes | DC Voltage | No* (depending on location) |
| Respiration Rate | Chest Volume Change | Strain Gauge | Change in Resistance | Yes |
| Skin Temperature | Surface Temperature Probe | Thermistors | Change in Resistance | Yes |
| Core Temperature | Esophageal or Rectal Probe | Thermistors | Change in Resistance | Yes |
| Heat Flow | Heat Flux | Thermopile | DC Voltage | Yes |
| Galvanic Skin Response | Skin Conductance | 2 Electrodes | Conductance | No |
| EMG | Skin Surface Potentials | 3 Electrodes | DC Voltage | No |
| EEG | Skin Surface Potentials | Multiple Electrodes | DC Voltage | Yes |

TABLE 1-continued

| Parameter | Example Method | Example Sensor | Signal | Further Processing |
|---|---|---|---|---|
| EOG | Eye Movement | Thin Film Piezoelectric Sensors | DC Voltage | Yes |
| Blood Pressure | Non-Invasive Korotkuff Sounds | Electronic Sphygromarometer | Change in Resistance | Yes |
| Body Fat | Body Impedance | 2 Active Electrodes | Change in Impedance | Yes |
| Activity | Body Movement | Accelerometer | DC Voltage, Capacitance Changes | Yes |
| Oxygen Consumption | Oxygen Uptake | Electro-chemical | DC Voltage Change | Yes |
| Glucose Level | Non-Invasive | Electro-chemical | DC Voltage Change | Yes |
| Body Position (e.g. supine, erect, sitting) | N/A | Mercury Switch Array | DC Voltage Change | Yes |
| Muscle Pressure | N/A | Thin Film Piezoelectric Sensors | DC Voltage Change | Yes |
| UV Radiation Absorption | N/A | UV Sensitive Photo Cells | DC Voltage Change | Yes |

It is to be specifically noted that a number of other types and categories of sensors may be utilized alone or in conjunction with those given above, including but not limited to relative and global positioning sensors for determination of location of the user; torque & rotational acceleration for determination of orientation in space; blood chemistry sensors; interstitial fluid chemistry sensors; bio-impedance sensors; and several contextual sensors, such as: pollen, humidity, ozone, acoustic, body and ambient noise and sensors adapted to utilize the device in a biofingerprinting scheme.

The types of data listed in Table 1 are intended to be examples of the types of data that can be generated by sensor device 10. It is to be understood that other types of data relating to other parameters can be generated by sensor device 10 without departing from the scope of the present invention.

The microprocessor of sensor device 10 may be programmed to summarize and analyze the data. For example, the microprocessor can be programmed to calculate an average, minimum or maximum heart rate or respiration rate over a defined period of time, such as ten minutes. Sensor device 10 may be able to derive information relating to an individual's physiological state based on the data indicative of one or more physiological parameters. The microprocessor of sensor device 10 is programmed to derive such information using known methods based on the data indicative of one or more physiological parameters. Table 2 provides examples of the type of information that can be derived, and indicates some of the types of data that can be used therefor.

TABLE 2

| Derived Information | Example Input Data Signals |
|---|---|
| Ovulation | Skin temperature, core temperature, oxygen consumption |
| Sleep onset/wake | Beat-to-beat variability, heart rate, pulse rate, respiration rate, skin temperature, core temperature, heat flow, galvanic skin response, EMG, EEG, EOG, blood pressure, oxygen consumption |
| Calories burned | Heart rate, pulse rate, respiration rate, heat flow, activity, oxygen consumption |
| Basal metabolic rate | Heart rate, pulse rate, respiration rate, heat flow, activity, oxygen consumption |
| Basal temperature | Skin temperature, core temperature |
| Activity level | Heart rate, pulse rate, respiration rate, heat flow, activity, oxygen consumption |
| Stress level | EKG, beat-to-beat variability, heart rate, pulse rate, respiration rate, skin temperature, heat flow, galvanic skin response, EMG, EEG, blood pressure, activity, oxygen consumption |
| Relaxation level | EKG, beat-to-beat variability, heart rate, pulse rate, respiration rate, skin temperature, heat flow, galvanic skin response, EMG, EEG, blood pressure, activity, oxygen consumption |
| Maximum oxygen consumption rate | EKG, heart rate, pulse rate, respiration rate, heat flow, blood pressure, activity, oxygen consumption |
| Rise time or the time it takes to rise from a resting rate to 85% of a target maximum | Heart rate, pulse rate, heat flow, oxygen consumption |
| Time in zone or the time heart rate was above 85% of a target maximum | Heart rate, pulse rate, heat flow, oxygen consumption |
| Recovery time or the time it takes heart rate to return to a resting rate after heart rate was above 85% of a target maximum | Heart rate, pulse rate, heat flow, oxygen consumption |

Additionally, sensor device 10 may also generate data indicative of various contextual parameters relating to activity state or the environment surrounding the individual. For example, sensor device 10 can generate data indicative of the air quality, sound level/quality, light quality or ambient temperature near the individual, or even the motion or global positioning of the individual. Sensor device 10 may include one or more sensors for generating signals in response to contextual characteristics relating to the environment surrounding the individual, the signals ultimately being used to generate the type of data described above. Such sensors are well known, as are methods for generating contextual parametric data such as air quality, sound level/quality, ambient temperature and global positioning.

Figure 2:
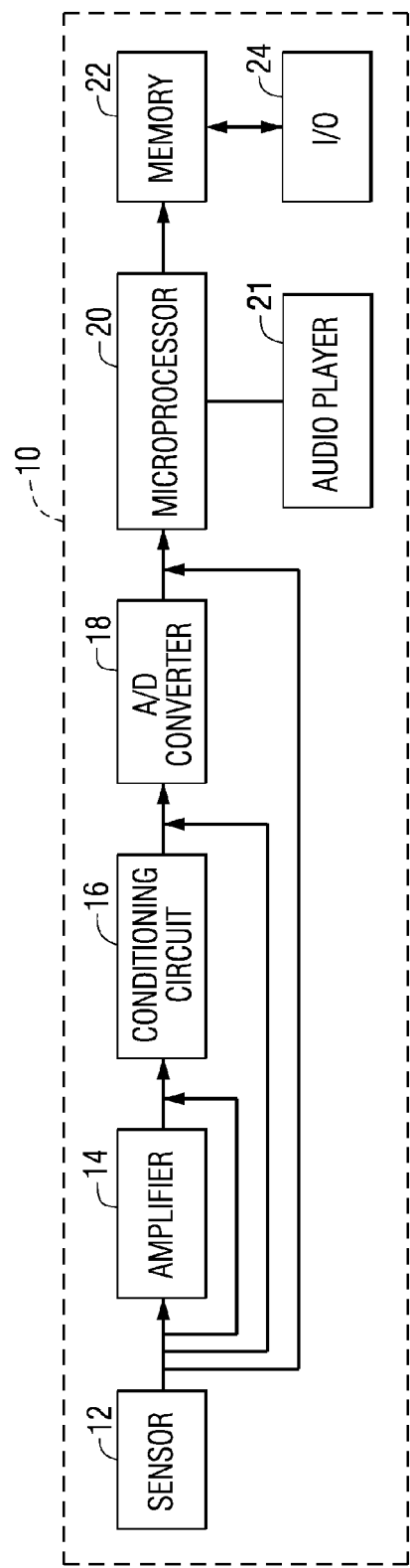
FIG. 2 is a block diagram of an embodiment of the sensor device shown in FIG. 1.

FIG. 2 is a block diagram of an embodiment of sensor device 10. Sensor device 10 includes at least one sensor 12 and microprocessor 20. Depending upon the nature of the signal generated by sensor 12, the signal can be sent through one or more of amplifier 14, conditioning circuit 16, and analog-to-digital converter 18, before being sent to microprocessor 20. For example, where sensor 12 generates an analog signal in need of amplification and filtering, that signal can be sent to amplifier 14, and then on to conditioning circuit 16, which may, for example, be a band pass filter. The amplified and conditioned analog signal can then be transferred to analog-to-digital converter 18, where it is converted to a digital signal. The digital signal is then sent to microprocessor 20. Alternatively, if sensor 12 generates a digital signal, that signal can be sent directly to microprocessor 20.

A digital signal or signals representing certain physiological and/or contextual characteristics of the individual user may be used by microprocessor 20 to calculate or generate data indicative of physiological and/or contextual parameters of the individual user. Microprocessor 20 is programmed to derive information relating to at least one aspect of the individual's physiological state. It should be understood that microprocessor 20 may also comprise other forms of processors or processing devices, such as a microcontroller, or any other device that can be programmed to perform the functionality described herein.

Optionally, central processing unit may provide operational control or, at a minimum, selection of an audio player device 21. As will be apparent to those skilled in the art, audio player 21 is of the type which either stores and plays or plays separately stored audio media. The device may control the output of audio player 21, as described in more detail below, or may merely furnish a user interface to permit control of audio player 21 by the wearer.

The data indicative of physiological and/or contextual parameters can, according to one embodiment of the present invention, be sent to memory 22, such as flash memory, where it is stored until uploaded in the manner to be described below. Although memory 22 is shown in FIG. 2 as a discrete element, it will be appreciated that it may also be part of microprocessor 20. Sensor device 10 also includes input/output circuitry 24, which is adapted to output and receive as input certain data signals in the manners to be described herein. Thus, memory 22 of the sensor device 10 will build up, over time, a store of data relating to the individual user's body and/or environment. That data is periodically uploaded from sensor device 10 and sent to remote central monitoring unit 30, as shown in FIG. 1, where it is stored in a database for subsequent processing and presentation to the user, preferably through a local or global electronic network such as the Internet. This uploading of data can be an automatic process that is initiated by sensor device 10 periodically or upon the happening of an event such as the detection by sensor device 10 of a heart rate below a certain level, or can be initiated by the individual user or some third party authorized by the user, preferably according to some periodic schedule, such as every day at 10:00 p.m. Alternatively, rather than storing data in memory 22, sensor device 10 may continuously upload data in real time.

The uploading of data from sensor device 10 to central monitoring unit 30 for storage can be accomplished in various ways. In one embodiment, the data collected by sensor device 10 is uploaded by first transferring the data to personal computer 35 shown in FIG. 1 by means of physical connection 40, which, for example, may be a serial connection such as an RS232 or USB port. This physical connection may also be accomplished by using a cradle, not shown, that is electronically coupled to personal computer 35 into which sensor device 10 can be inserted, as is common with many commercially available personal digital assistants. The uploading of data could be initiated by then pressing a button on the cradle or could be initiated automatically upon insertion of sensor device 10 or upon proximity to a wireless receiver. The data collected by sensor device 10 may be uploaded by first transferring the data to personal computer 35 by means of short-range wireless transmission, such as infrared or RF transmission, as indicated at 45.

Once the data is received by personal computer 35, it is optionally compressed and encrypted by any one of a variety of well known methods and then sent out over a local or global electronic network, preferably the Internet, to central monitoring unit 30. It should be noted that personal computer 35 can be replaced by any computing device that has access to and that can transmit and receive data through the electronic network, such as, for example, a personal digital assistant such as the Palm VII sold by Palm, Inc., or the Blackberry 2-way pager sold by Research in Motion, Inc.

Alternatively, the data collected by sensor device 10, after being encrypted and, optionally, compressed by microprocessor 20, may be transferred to wireless device 50, such as a 2-way pager or cellular phone, for subsequent long distance wireless transmission to local telco site 55 using a wireless protocol such as e-mail or as ASCII or binary data. Local telco site 55 includes tower 60 that receives the wireless transmission from wireless device 50 and computer 65 connected to tower 60. According to the preferred embodiment, computer 65 has access to the relevant electronic network, such as the Internet, and is used to transmit the data received in the form of the wireless transmission to the central monitoring unit 30 over the Internet. Although wireless device 50 is shown in FIG. 1 as a discrete device coupled to sensor device 10, it or a device having the same or similar functionality may be embedded as part of sensor device 10.

Sensor device 10 may be provided with a button to be used to time stamp events such as time to bed, wake time, and time of meals. These time stamps are stored in sensor device 10 and are uploaded to central monitoring unit 30 with the rest of the data as described above. The time stamps may include a digitally recorded voice message that, after being uploaded to central monitoring unit 30, are translated using voice recognition technology into text or some other information format that can be used by central monitoring unit 30. Note that in an alternate embodiment, these time-stamped events can be automatically detected.

In addition to using sensor device 10 to automatically collect physiological data relating to an individual user, a kiosk could be adapted to collect such data by, for example, weighing the individual, providing a sensing device similar to sensor device 10 on which an individual places his or her hand or another part of his or her body, or by scanning the individual's body using, for example, laser technology or an iStat blood analyzer. The kiosk would be provided with processing capability as described herein and access to the relevant electronic network, and would thus be adapted to send the collected data to the central monitoring unit 30 through the electronic network. A desktop sensing device, again similar to sensor device 10, on which an individual places his or her hand or another part of his or her body may also be provided. For example, such a desktop sensing device could be a blood pressure monitor in which an individual places his or her arm. An individual might also wear a ring having a sensor device 10 incorporated therein. A base, not shown, could then be provided which is adapted to be coupled to the ring. The desktop sensing device or the base just described may then be coupled to a computer such as personal computer 35 by means of a physical or short range wireless connection so that the collected data could be uploaded to central monitoring unit 30 over the relative electronic network in the manner described above. A mobile device such as, for example, a personal digital assistant, might also be provided with a sensor device 10 incorporated therein. Such a sensor device 10 would be adapted to collect data when mobile device is placed in proximity with the individual's body, such as by holding the device in the palm of one's hand, and upload the collected data to central monitoring unit 30 in any of the ways described herein.

An alternative embodiment includes the incorporation of third party devices, not necessary worn on the body, collect additional data pertaining to physiological conditions. Examples include portable blood analyzers, glucose monitors, weight scales, blood pressure cuffs, pulse oximeters, CPAP machines, portable oxygen machines, home thermostats, treadmills, cell phones and GPS locators. The system could collect from, or in the case of a treadmill or CPAP, control these devices, and collect data to be integrated into the streams for real time or future derivations of new parameters. An example of this is a pulse oximeter on the user's finger could help measure pulse and therefore serve a surrogate reading for blood pressure. Additionally, a user could utilize one of these other devices to establish baseline readings in order to calibrate the device.

Furthermore, in addition to collecting data by automatically sensing such data in the manners described above, individuals can also manually provide data relating to various life activities that is ultimately transferred to and stored at central monitoring unit 30. An individual user can access a web site maintained by central monitoring unit 30 and can directly input information relating to life activities by entering text freely, by responding to questions posed by the web site, or by clicking through dialog boxes provided by the web site. Central monitoring unit 30 can also be adapted to periodically send electronic mail messages containing questions designed to elicit information relating to life activities to personal computer 35 or to some other device that can receive electronic mail, such as a personal digital assistant, a pager, or a cellular phone. The individual would then provide data relating to life activities to central monitoring unit 30 by responding to the appropriate electronic mail message with the relevant data. Central monitoring unit 30 may also be adapted to place a telephone call to an individual user in which certain questions would be posed to the individual user. The user could respond to the questions by entering information using a telephone keypad, or by voice, in which case conventional voice recognition technology would be used by central monitoring unit 30 to receive and process the response. The telephone call may also be initiated by the user, in which case the user could speak to a person directly or enter information using the keypad or by voice/voice recognition technology. Central monitoring unit 30 may also be given access to a source of information controlled by the user, for example the user's electronic calendar such as that provided with the Outlook product sold by Microsoft Corporation of Redmond, Wash., from which it could automatically collect information. The data relating to life activities may relate to the eating, sleep, exercise, mind centering or relaxation, and/or daily living habits, patterns and/or activities of the individual. Thus, sample questions may include: What did you have for lunch today? What time did you go to sleep last night? What time did you wake up this morning? How long did you run on the treadmill today?

Feedback may also be provided to a user directly through sensor device 10 in a visual form, for example through an LED or LCD or by constructing sensor device 10, at least in part, of a thermochromatic plastic, in the form of an acoustic signal or in the form of tactile feedback such as vibration. Such feedback may be a reminder or an alert to eat a meal or take medication or a supplement such as a vitamin, to engage in an activity such as exercise or meditation, or to drink water when a state of dehydration is detected. Additionally, a reminder or alert can be issued in the event that a particular physiological parameter such as ovulation has been detected, a level of calories burned during a workout has been achieved or a high heart rate or respiration rate has been encountered.

As will be apparent to those of skill in the art, it may be possible to download data from central monitoring unit 30 to sensor device 10. The flow of data in such a download process would be substantially the reverse of that described above with respect to the upload of data from sensor device 10. Thus, it is possible that the firmware of microprocessor 20 of sensor device 10 can be updated or altered remotely, i.e., the microprocessor can be reprogrammed, by downloading new firmware to sensor device 10 from central monitoring unit 30 for such parameters as timing and sample rates of sensor device 10. Also, the reminders/alerts provided by sensor device 10 may be set by the user using the web site maintained by central monitoring unit 30 and subsequently downloaded to the sensor device 10.

Figure 3:
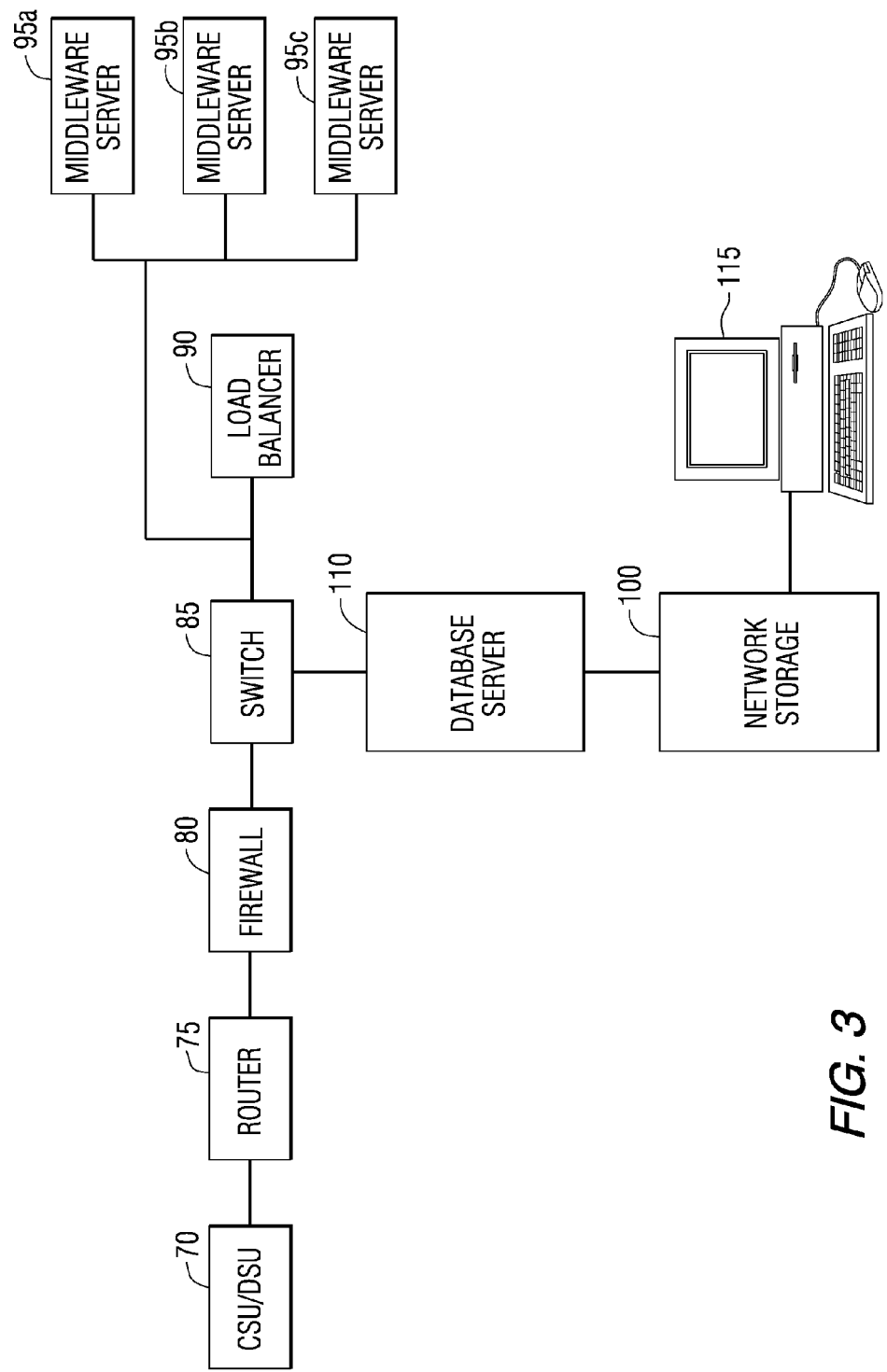
FIG. 3 is a block diagram of an embodiment of the central monitoring unit shown in FIG. 1.

Referring to FIG. 3, a block diagram of an embodiment of central monitoring unit 30 is shown. Central monitoring unit 30 includes CSU/DSU 70 which is connected to router 75, the main function of which is to take data requests or traffic, both incoming and outgoing, and direct such requests and traffic for processing or viewing on the web site maintained by central monitoring unit 30. Connected to router 75 is firewall 80. The main purpose of firewall 80 is to protect the remainder of central monitoring unit 30 from unauthorized or malicious intrusions. Switch 85, connected to firewall 80, is used to direct data flow between middleware servers 95_a_ through 95_c_ and database server 110. Load balancer 90 is provided to spread the workload of incoming requests among the identically configured middleware servers 95_a_ through 95_c_. Load balancer 90, a suitable example of which is the F5 ServerIron product sold by Foundry Networks, Inc. of San Jose, Calif., analyzes the availability of each middleware server 95_a_ through 95_c_, and the amount of system resources being used in each middleware server 95_a_ through 95_c_, in order to spread tasks among them appropriately.

Central monitoring unit 30 includes network storage device 100, such as a storage area network or SAN, which acts as the central repository for data. In particular, network storage device 100 comprises a database that stores all data gathered for each individual user in the manners described above. An example of a suitable network storage device 100 is the Symmetrix product sold by EMC Corporation of Hopkinton, Mass. Although only one network storage device 100 is shown in FIG. 3, it will be understood that multiple network storage devices of various capacities could be used depending on the data storage needs of central monitoring unit 30. Central monitoring unit 30 also includes database server 110 which is coupled to network storage device 100. Database server 110 is made up of two main components: a large scale multiprocessor server and an enterprise type software server component such as the 8/8i component sold by Oracle Corporation of Redwood City, Calif., or the 506 7 component sold by Microsoft Corporation of Redmond, Wash. The primary functions of database server 110 are that of providing access upon request to the data stored in network storage device 100, and populating network storage device 100 with new data. Coupled to network storage device 100 is controller 115, which typically comprises a desktop personal computer, for managing the data stored in network storage device 100.

Middleware servers 95a through 95c, a suitable example of which is the 22OR Dual Processor sold by Sun Microsystems, Inc. of Palo Alto, Calif., each contain software for generating and maintaining the corporate or home web page or pages of the web site maintained by central monitoring unit 30. As is known in the art, a web page refers to a block or blocks of data available on the World-Wide Web comprising a file or files written in Hypertext Markup Language or HTML, and a web site commonly refers to any computer on the Internet running a World-Wide Web server process. The corporate or home web page or pages are the opening or landing web page or pages that are accessible by all members of the general public that visit the site by using the appropriate uniform resource locator or URL. As is known in the art, URLs are the form of address used on the World-Wide Web and provide a standard way of specifying the location of an object, typically a web page, on the Internet. Middleware servers 95a through 95c also each contain software for generating and maintaining the web pages of the web site of central monitoring unit 30 that can only be accessed by individuals that register and become members of central monitoring unit 30. The member users will be those individuals who wish to have their data stored at central monitoring unit 30. Access by such member users is controlled using passwords for security purposes. Preferred embodiments of those web pages are described in detail below and are generated using collected data that is stored in the database of network storage device 100.

Middleware servers 95a through 95c also contain software for requesting data from and writing data to network storage device 100 through database server 110. When an individual user desires to initiate a session with the central monitoring unit 30 for the purpose of entering data into the database of network storage device 100, viewing his or her data stored in the database of network storage device 100, or both, the user visits the home web page of central monitoring unit 30 using a browser program such as Internet Explorer distributed by Microsoft Corporation of Redmond, Wash., and logs in as a registered user. Load balancer 90 assigns the user to one of the middleware servers 95a through 95c, identified as the chosen middleware server. A user will preferably be assigned to a chosen middleware server for each entire session. The chosen middleware server authenticates the user using any one of many well known methods, to ensure that only the true user is permitted to access the information in the database. A member user may also grant access to his or her data to a third party such as a health care provider or a personal trainer. Each authorized third party may be given a separate password and may view the member user's data using a conventional browser. It is therefore possible for both the user and the third party to be the recipient of the data.

When the user is authenticated, the chosen middleware server requests, through database server 110, the individual user's data from network storage device 100 for a predetermined time period. The predetermined time period is preferably thirty days. The requested data, once received from network storage device 100, is temporarily stored by the chosen middleware server in cache memory. The cached data is used by the chosen middleware server as the basis for presenting information, in the form of web pages, to the user again through the user's browser. Each middleware server 95a through 95c is provided with appropriate software for generating such web pages, including software for manipulating and performing calculations utilizing the data to put the data in appropriate format for presentation to the user. Once the user ends his or her session, the data is discarded from cache. When the user initiates a new session, the process for obtaining and caching data for that user as described above is repeated. This caching system thus ideally requires that only one call to the network storage device 100 be made per session, thereby reducing the traffic that database server 110 must handle. Should a request from a user during a particular session require data that is outside of a predetermined time period of cached data already retrieved, a separate call to network storage device 100 may be performed by the chosen middleware server. The predetermined time period should be chosen, however, such that such additional calls are minimized. Cached data may also be saved in cache memory so that it can be reused when a user starts a new session, thus eliminating the need to initiate a new call to network storage device 100.

As described in connection with Table 2, the microprocessor of sensor device 10 may be programmed to derive information relating to an individual's physiological state based on the data indicative of one or more physiological parameters. Central monitoring unit 30, and preferably middleware servers 95a through 95c, may also be similarly programmed to derive such information based on the data indicative of one or more physiological parameters.

It is also contemplated that a user will input additional data during a session, for example, information relating to the user's eating or sleeping habits. This additional data is preferably stored by the chosen middleware server in a cache during the duration of the user's session. When the user ends the session, this additional new data stored in a cache is transferred by the chosen middleware server to database server 110 for population in network storage device 100. Alternatively, in addition to being stored in a cache for potential use during a session, the input data may also be immediately transferred to database server 110 for population in network storage device 100, as part of a write-through cache system which is well known in the art.

Data collected by sensor device 10 shown in FIG. 1 is periodically uploaded to central monitoring unit 30. Either by long distance wireless transmission or through personal computer 35, a connection to central monitoring unit 30 is made through an electronic network, preferably the Internet. In particular, connection is made to load balancer 90 through CSU/DSU 70, router 75, firewall 80 and switch 85. Load balancer 90 then chooses one of the middleware servers 95a through 95c to handle the upload of data, hereafter called the chosen middleware server. The chosen middleware server authenticates the user using any one of many well known methods. If authentication is successful, the data is uploaded to the chosen middleware server as described above, and is ultimately transferred to database server 110 for population in the network storage device 100.

Figure 4:
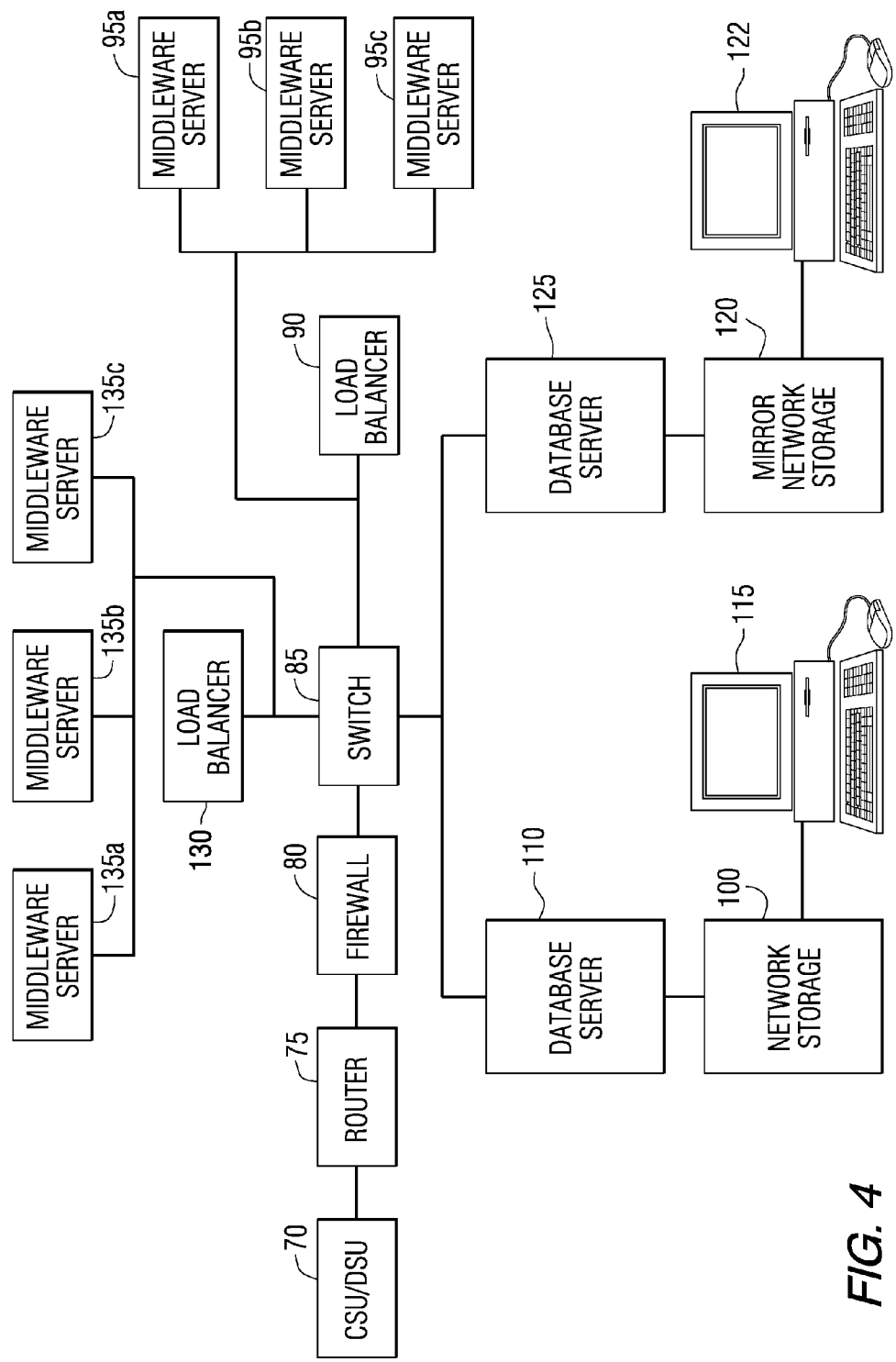
FIG. 4 is a block diagram of an alternate embodiment of the central monitoring unit shown in FIG. 1.

Referring to FIG. 4, an alternate embodiment of central monitoring unit 30 is shown. In addition to the elements shown and described with respect to FIG. 3, the embodiment of the central monitoring unit 30 shown in FIG. 4 includes a mirror network storage device 120 which is a redundant backup of network storage device 100. Coupled to mirror network storage device 120 is controller 122. Data from network storage device 100 is periodically copied to mirror network storage device 120 for data redundancy purposes.

Third parties such as insurance companies or research institutions may be given access, possibly for a fee, to certain of the information stored in mirror network storage device 120. Preferably, in order to maintain the confidentiality of the individual users who supply data to central monitoring unit 30, these third parties are not given access to such user's individual database records, but rather are only given access to the data stored in mirror network storage device 120 in aggregate form. Such third parties may be able to access the information stored in mirror network storage device 120 through the Internet using a conventional browser program. Requests from third parties may come in through CSU/DSU 70, router 75, firewall 80 and switch 85. In the embodiment shown in FIG. 4, a separate load balancer 130 is provided for spreading tasks relating to the accessing and presentation of data from mirror drive array 120 among identically configured middleware servers 135a through 135c. Middleware servers 135a through 135c each contain software for enabling the third parties to, using a browser, formulate queries for information from mirror network storage device 120 through separate database server 125. Middleware servers 135a through 135c also contain software for presenting the information obtained from mirror network storage device 120 to the third parties over the Internet in the form of web pages. In addition, the third parties can choose from a series of prepared reports that have information packaged along subject matter lines, such as various demographic categories.

As will be apparent to one of skill in the art, instead of giving these third parties access to the backup data stored in mirror network storage device 120, the third parties may be given access to the data stored in network storage device 100. Also, instead of providing load balancer 130 and middleware servers 135a through 135c, the same functionality, although at a sacrificed level of performance, could be provided by load balancer 90 and middleware servers 95a through 95c.

When an individual user first becomes a registered user or member, that user completes a detailed survey. The purposes of the survey are to: identify unique characteristics/circumstances for each user that they might need to address in order to maximize the likelihood that they will implement and maintain a healthy lifestyle as suggested by central monitoring unit 30; gather baseline data which will be used to set initial goals for the individual user and facilitate the calculation and display of certain graphical data output such as the Health Index pistons; identify unique user characteristics and circumstances that will help central monitoring unit 30 customize the type of content provided to the user in the Health Manager's Daily Dose; and identify unique user characteristics and circumstances that the Health Manager can guide the user to address as possible barriers to a healthy lifestyle through the problem-solving function of the Health Manager.

In an alternative embodiment specifically directed to a weight loss or management application, as more fully described herein, a user may elect to wear the sensor device 10 long term or continuously in order to observe changes in certain health or weight related parameters. Alternatively, the user may elect to only wear the sensor device 10 for a brief, initial period of time in order to establish a baseline or initial evaluation of their typical daily caloric intake and energy expenditure. This information may form the basis for diet and/or exercise plans, menu selections, meal plans and the like, and progress may be checked periodically by returning to use of the sensor device 10 for brief periods within the time frame established for the completion of any relevant weight loss or change goal.

The specific information to be surveyed may include: key individual temperamental characteristics, including activity level, regularity of eating, sleeping, and bowel habits, initial response to situations, adaptability, persistence, threshold of responsiveness, intensity of reaction, and quality of mood; the user's level of independent functioning, i.e., self-organization and management, socialization, memory, and academic achievement skills; the user's ability to focus and sustain attention, including the user's level of arousal, cognitive tempo, ability to filter distractions, vigilance, and self-monitoring; the user's current health status including current weight, height, and blood pressure, most recent general physician visit, gynecological exam, and other applicable physician/healthcare contacts, current medications and supplements, allergies, and a review of current symptoms and/or health-related behaviors; the user's past health history, i.e., illnesses/surgeries, family history, and social stress events, such as divorce or loss of a job, that have required adjustment by the individual; the user's beliefs, values and opinions about health priorities, their ability to alter their behavior and, what might contribute to stress in their life, and how they manage it; the user's degree of self-awareness, empathy, empowerment, and self-esteem, and the user's current daily routines for eating, sleeping, exercise, relaxation and completing activities of daily living; and the user's perception of the temperamental characteristics of two key persons in their life, for example, their spouse, a friend, a co-worker, or their boss, and whether there are clashes present in their relationships that might interfere with a healthy lifestyle or contribute to stress.

In the weight loss or management application, an individual user first becomes a registered user or member of a software platform and is issued a body monitoring apparatus that collects data from the user. The user may further personalize the apparatus by input of specific information into the software platform. This information may include: name, birth date, height, weight, gender, waistline measurements, body type, smoker/nonsmoker, lifestyle, typical activities, usual bed time and usual wake time. After the user connects the apparatus to a personal computer or other similar device by any of the means of the connectivity described above, the apparatus configuration is updated with this information. The user may also have the option to set a reminder which may be a reminder to take a vitamin at a certain time, to engage in physical activity, or to upload data. After the configuration process is complete, the program displays how the device should be worn on the body, and the user removes the apparatus from the personal computer for placement of the apparatus in the appropriate location on the body for the collection of data. Alternatively, some of this personalization can happen through an initial trial wearing period.

Figure 5:
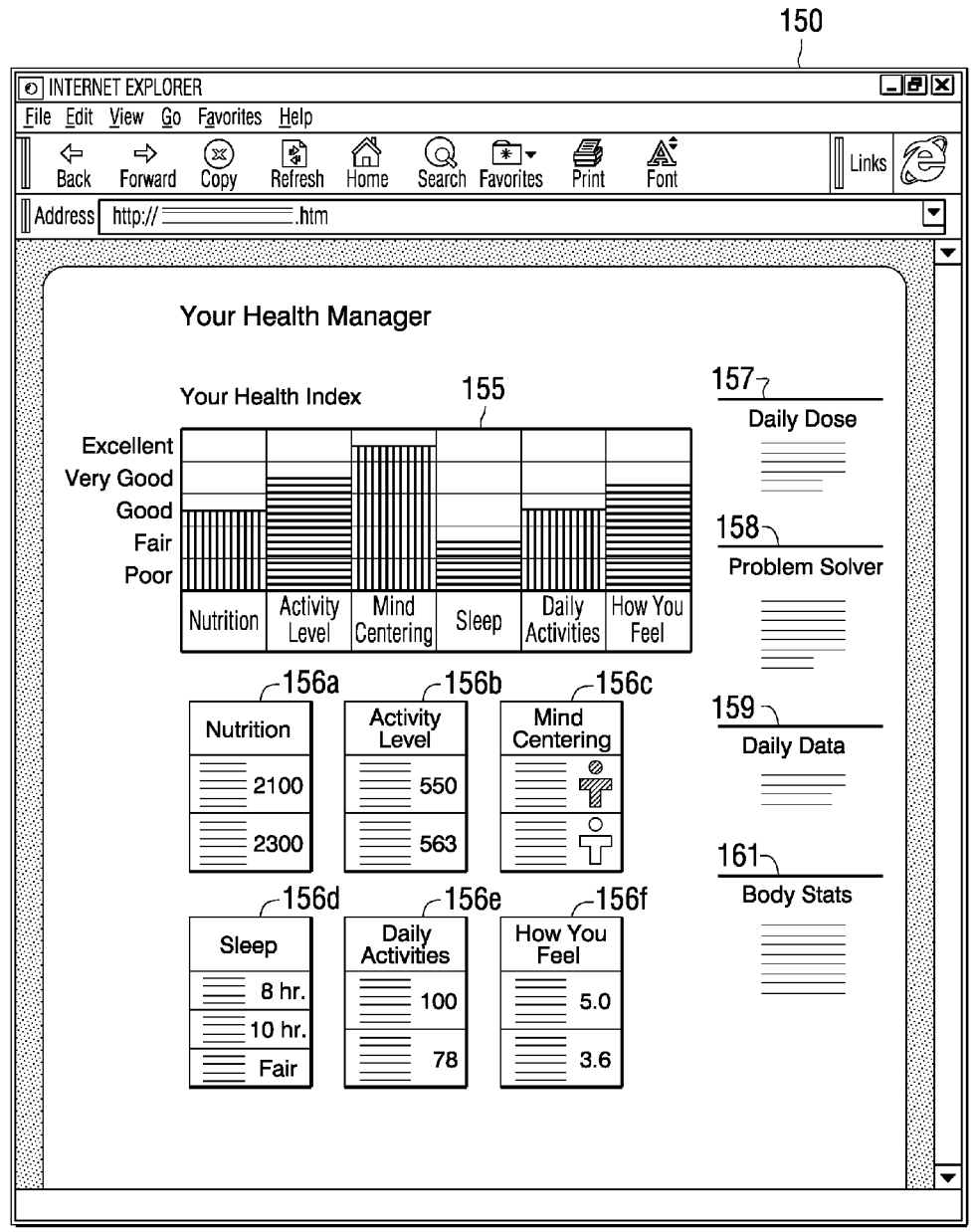
FIG. 5 is a representation of a preferred embodiment of the Health Manager web page according to an aspect of the present invention.

In the more generally directed embodiments, each member user will have access, through the home web page of central monitoring unit 30, to a series of web pages customized for that user, referred to as the Health Manager. The opening Health Manager web page 150 is shown in FIG. 5. The Health Manager web pages are the main workspace area for the member user. The Health Manager web pages comprise a utility through which central monitoring unit 30 provides various types and forms of data, commonly referred to as analytical status data, to the user that is generated from the data it collects or generates, namely one or more of: the data indicative of various physiological parameters generated by sensor device 10; the data derived from the data indicative of various physiological parameters; the data indicative of various contextual parameters generated by sensor device 10; and the data input by the user. Analytical status data is characterized by the application of certain utilities or algorithms to convert one or more of the data indicative of various physiological parameters generated by sensor device 10, the data derived from the data indicative of various physiological parameters, the data indicative of various contextual parameters generated by sensor device 10, and the data input by the user into calculated health, wellness and lifestyle indicators. For example, based on data input by the user relating to the foods he or she has eaten, things such as calories and amounts of proteins, fats, carbohydrates, and certain vitamins can be calculated. As another example, skin temperature, heart rate, respiration rate, heat flow and/or GSR can be used to provide an indicator to the user of his or her stress level over a desired time period. As still another example, skin temperature, heat flow, beat-to-beat heart variability, heart rate, pulse rate, respiration rate, core temperature, galvanic skin response, EMG, EEG, EOG, blood pressure, oxygen consumption, ambient sound and body movement or motion as detected by a device such as an accelerometer can be used to provide indicators to the user of his or her sleep patterns over a desired time period.

Located on the opening Health Manager web page 150 is Health Index 155. Health Index 155 is a graphical utility used to measure and provide feedback to member users regarding their performance and the degree to which they have succeeded in reaching a healthy daily routine suggested by central monitoring unit 30. Health Index 155 thus provides an indication for the member user to track his or her progress. Health Index 155 includes six categories relating to the user's health and lifestyle: Nutrition, Activity Level, Mind Centering, Sleep, Daily Activities and How You Feel. The Nutrition category relates to what, when and how much a person eats and drinks. The Activity Level category relates to how much a person moves around. The Mind Centering category relates to the quality and quantity of time a person spends engaging in some activity that allows the body to achieve a state of profound relaxation while the mind becomes highly alert and focused. The Sleep category relates to the quality and quantity of a person's sleep. The Daily Activities category relates to the daily responsibilities and health risks people encounter. Finally, the How You Feel category relates to the general perception that a person has about how they feel on a particular day. Each category has an associated level indicator or piston that indicates, preferably on a scale ranging from poor to excellent, how the user is performing with respect to that category.

When each member user completes the initial survey described above, a profile is generated that provides the user with a summary of his or her relevant characteristics and life circumstances. A plan and/or set of goals is provided in the form of a suggested healthy daily routine. The suggested healthy daily routine may include any combination of specific suggestions for incorporating proper nutrition, exercise, mind centering, sleep, and selected activities of daily living in the user's life. Prototype schedules may be offered as guides for how these suggested activities can be incorporated into the user's life. The user may periodically retake the survey, and based on the results, the items discussed above will be adjusted accordingly.

The Nutrition category is calculated from both data input by the user and sensed by sensor device 10. The data input by the user comprises the time and duration of breakfast, lunch, dinner and any snacks, and the foods eaten, the supplements such as vitamins that are taken, and the water and other liquids consumed during a relevant, pre-selected time period. Based upon this data and on stored data relating to known properties of various foods, central monitoring unit 30 calculates well known nutritional food values such as calories and amounts of proteins, fats, carbohydrates, vitamins, etc., consumed.

The Nutrition Health Index piston level is preferably determined with respect to the following suggested healthy daily routine: eat at least three meals; eat a varied diet consisting of 6-11 servings of bread, pasta, cereal, and rice, 2-4 servings fruit, 3-5 servings of vegetables, 2-3 servings of fish, meat, poultry, dry beans, eggs, and nuts, and 2-3 servings of milk, yogurt and cheese; and drink 8 or more 8 ounce glasses of water. This routine may be adjusted based on information about the user, such as sex, age, height and/or weight. Certain nutritional targets may also be set by the user or for the user, relating to daily calories, protein, fiber, fat, carbohydrates, and/or water consumption and percentages of total consumption. Parameters utilized in the calculation of the relevant piston level include the number of meals per day, the number of glasses of water, and the types and amounts of food eaten each day as input by the user.

Figure 6:
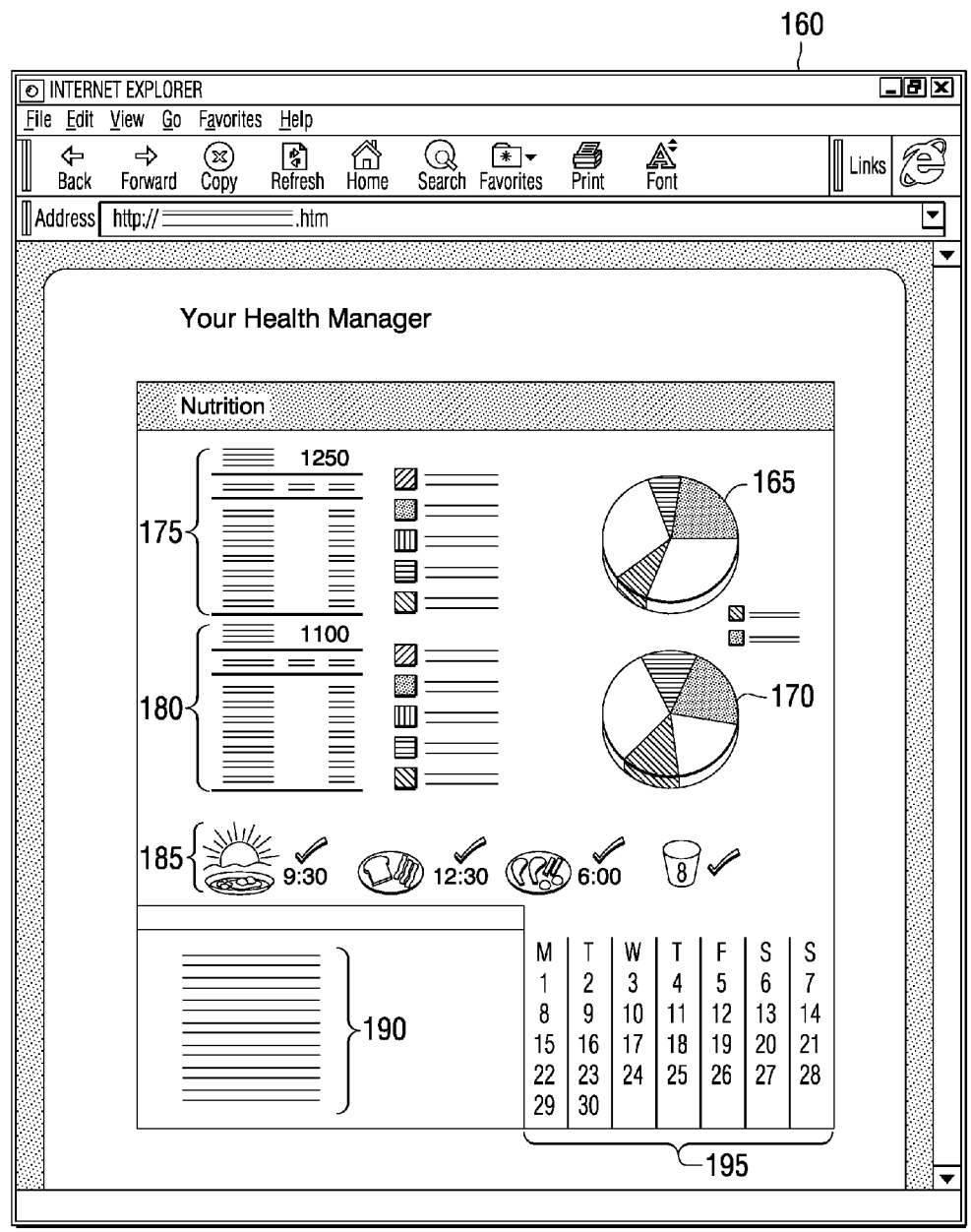
FIG. 6 is a representation of a preferred embodiment of the nutrition web page according to an aspect of the present invention.

Nutritional information is presented to the user through nutrition web page 160 as shown in FIG. 6. The preferred nutritional web page 160 includes nutritional fact charts 165 and 170 which illustrate actual and target nutritional facts, respectively as pie charts, and nutritional intake charts 175 and 180 which show total actual nutritional intake and target nutritional intake, respectively as pie charts. Nutritional fact charts 165 and 170 preferably show a percentage breakdown of items such as carbohydrates, protein and fat, and nutritional intake charts 175 and 180 are preferably broken down to show components such as total and target calories, fat, carbohydrates, protein, and vitamins. Web page 160 also includes meal and water consumption tracking 185 with time entries, hyperlinks 190 which allow the user to directly access nutrition-related news items and articles, suggestions for refining or improving daily routine with respect to nutrition and affiliate advertising elsewhere on the network, and calendar 195 for choosing between views having variable and selectable time periods. The items shown at 190 may be selected and customized based on information learned about the individual in the survey and on their performance as measured by the Health Index.

In the weight management embodiment, a user may also have access through central monitoring unit 30 to a software platform referred to as the Weight Manager which may be included in the Health Manager module or independent. It is also contemplated that Weight Manager may be a web-based application.

When the Weight Manager software platform is initialized, a registered user may login to the Weight Manager. If a user is not registered, they must complete the registration process before using another part of the software platform. The user begins the registration process by selecting a user name and password and entering the serial number of the apparatus.

Figure 7:
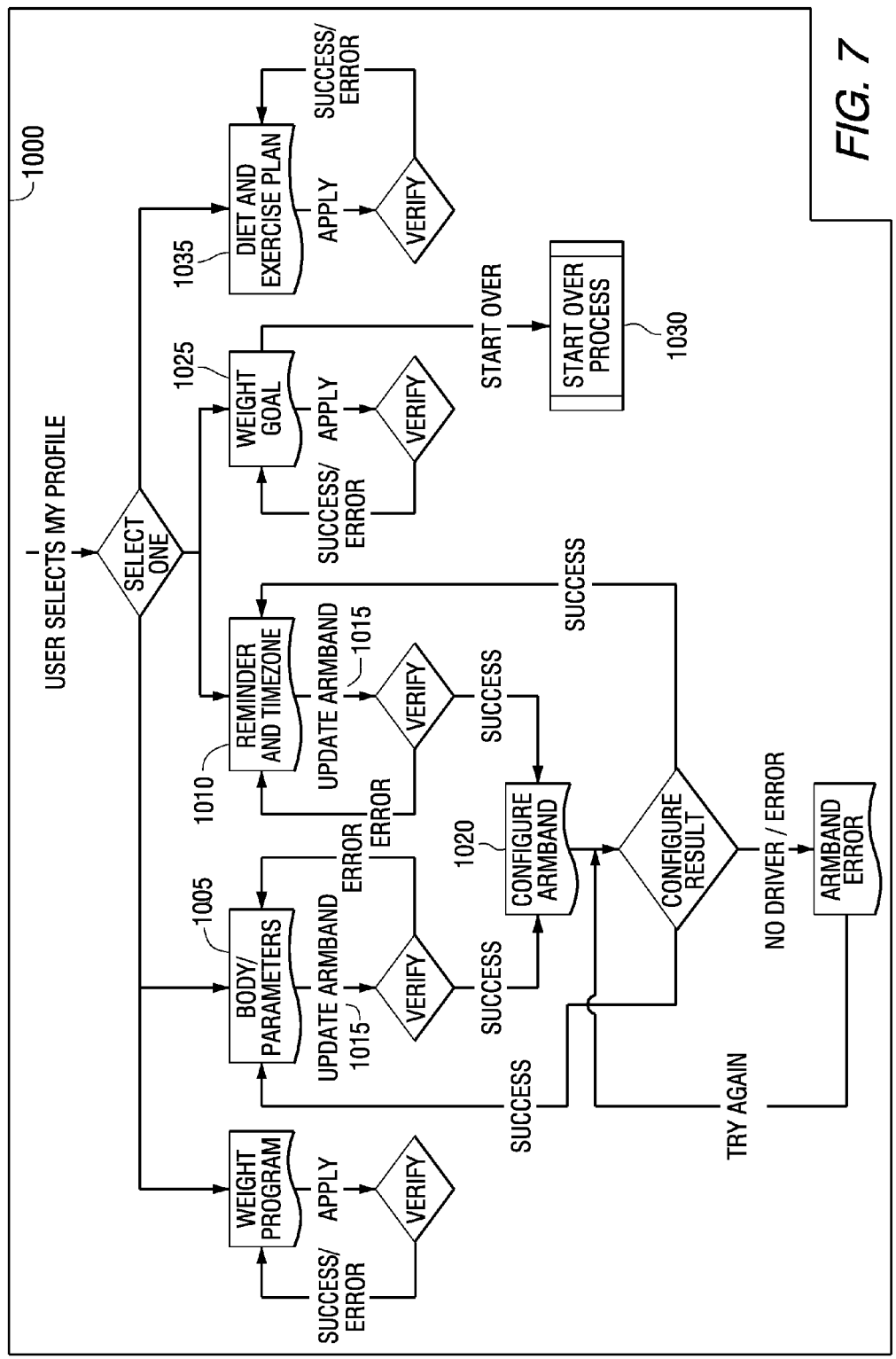
FIG. 7 is an block diagram representing the configuration of the management system for a specific user according to an aspect of the present invention.

FIG. 7 is a block diagram illustrating the steps used to configure the personalized Weight Manager. During the initial configuration of the Weight Manager, the user may personalize the system with specific information in the user profile 1000 of the Weight Manager. The user may also return to the user profile 1000 at any time during the use of the system to modify the information. On the body parameters screen 1005 the user may enter specific information including: name, birth date, height, weight, sex, waistline measurement, right or left handedness, body frame size, smoker/nonsmoker, physical activity level, bed time and wake time. On the reminders screen 1010 the user may select a time zone from a pull-down menu in addition to setting a reminder. If any information on the body parameter screen 1005 or the reminders screen 1010 is modified, an armband update button 1015 allows the user to start the upload process for armband configuration 1020.

On the weight goals screen 1025, the user is given the option of setting weight loss goals. If the user selects this option, the user will be asked to enter the following information to establish these goals: current weight, goal weight, goal date to reach the goal weight, the target daily caloric intake and the target daily caloric burn rate. The system will then calculate the following: body mass index at the user's current weight, the body mass index at the goal weight, weight loss per week required to reach goal weight by the target date, and the daily caloric balance at the entered daily intake and burn rates. The screen may also display risk factor bars that show the risk of certain conditions such as diabetes, heart disease, hypertension, stroke and premature death at the user's current weight in comparison to the risk at the goal weight. The current and goal risk factors of each disease state may be displayed side-by-side for the user. The user is given a start over option 1030 if they have not entered any information for more than 5 days.

The user may also establish a diet and exercise plan on the diet and exercise plan screen 1035 from a selection of plans which may include a low carb, high protein diet plan or a more health condition related diet and exercise plan such as that prescribed by the American Heart Association or the American Diabetes Association. It is to be specifically noted that all such diets, including many not listed herein, are interchangeable for the purposes of this application. The user's diet plan is selected from a pull-down menu. The user also enters their expected intake of fat, carbohydrates and protein as percentages of their overall caloric intake. The user also selects appropriate exercises from a pull down menu or these exercises can be manually entered.

According to one aspect of the present invention, the system generates individualized daily meal plans to help the user attain their health and fitness goals. The system uses a database of food and meals (combinations of foods) to create daily menus. The database of food and meals is used in conjunction with user preferences, health and fitness goals, lifestyle, body type and dietary restrictions which constrain the types of meals included in the menu. These individual constraints determine a personalized calorie range and nutritional breakdown for the user's meal plan. Meals are assigned to menus in a best-first strategy to fall within a desired tolerance of the optimal daily caloric and nutritional balance.

According to another aspect of the present invention, the system may utilize the information regarding the user's daily energy expenditure to produce menus with calories that may compensate for the user's actual energy expenditure throughout the day. For example, if a user typically exercises right before lunch, the lunch can be made slightly larger. The feedback between the information gathered from the armband and the menus can help the user achieve fitness and health goals more quickly.

The user logs meals on a daily basis by selecting individual food items from the food database. The food database provides an extensive list of commonly consumed foods, e.g., milk, bread, common foods available at certain regional or national restaurant chains, e.g., McDonald's and Burger King, as well as brand name entrees, e.g., Weight Watchers or Mrs. T's, available in grocery stores. The name of the food, caloric content of the food and the nutrient information is stored in the database. Equivalent foods can be found in the case of simple preparations. If the user elects to not provide detailed nutritional information, a summary meal entry, such as large, medium or small meal, may be substituted. This will provide a baseline nutritional input for the energy balance features described herein. Over time, as described more fully below, the accuracy of these estimations can be improved through feedback of the system which monitors and estimates the amount of calories actually consumed and correlates the same to the large, medium and small categories.

For greater accuracy, the capability to add custom preparations is an option. There are two ways a user can add a custom food. The first is by creating a custom food or meal by adding either the ingredients or dishes of a larger composite dish or meal. The second way is by entering the data found on the back of processed or packaged foods. Either way constitutes an addition to the user's food database for later retrieval. If the user wants to add their own custom food, the food database provides the capability to the user to name their own preparation, enter the ingredients and also the caloric and nutrient contents. When entering a custom preparation, the user must specify a name and at least one ingredient. Once the preparation is added as a custom food to the database, it is available to be selected as the rest of the foods in the database for that user. The custom food data may include calories, total fat, sodium content, total carbohydrate content, total protein content, fiber and cholesterol in each serving. These values may be estimated based on the ingredients entered.

Another aspect of the current invention is to utilize adaptive and inferential methods to further simplify the food entry process. These methods include helping the user correctly choose the portion sizes of meals or ingredients and by automatically simplifying the system for the user over time. One example of the first method is to query the user when certain foods are entered. For example, when lasagna is entered, the user is queried about details of the lasagna dish to help narrow down the caloric content of the food. Furthermore, the user's portion sizes can be compared to the typical portion sizes entered for the given meal, and the user is queried when their entry is out of range. Finally, the user can be queried about commonly related foods when certain foods are entered. For example, when a turkey sandwich is entered, the user can be prompted about condiments, since it is highly likely that some condiments were consumed. In general, these suggestions are driven based on conditional probabilities. Given that the user had beer, for example, the system might suggest pizza. These suggestions can be hard-coded or derived from picking out common patterns in the population database or a regional, familial, seasonal or individual subset.

In a similar vein, the user's patterns and their relationship to the rest of the population can also be used to drive other aspects of the food entry interaction. For example, if the user has a particular combination of foods regularly, the system suggests that the user make that combination a custom meal.

Another aspect of this invention is that the order of foods in the frequent food list or in the database lookup can be designed to maximize the probability that the user will select foods with the fewest clicks possible. Instead of launching the page with a blank meal, the system can also guess at the meal using the historical meal entry information, the physiological data, the user's body parameters, general population food entry data, or in light of relationships with specific other users. For example, if the system has noticed that two or more users often have nearly identical meals on a regular pattern, the system can use one user's entry to prompt the second user. For example, if a wife had a cheeseburger, the system can prompt the husband with the same meal. For a group of six individuals that seems to all have a particular brand of sandwiches for lunch on Tuesdays, the system can use the input from one to drive the promptings for the other users. Additionally, in institutional settings, such as a hospital or lo assisted living center, where large numbers of the same meal or meals are being distributed, a single entry for each meal component could be utilized for all of the wearer/patients. Another aspect is to use the physiology directly to drive suggestions, for example, if the system detects a large amount of activity, sports drinks can be prompted.

The food input screen is the front end to the food database. The user interface provides the capability to search the food database. The search is both interactive and capable of letter and phrase matching to speed input. The user begins a search by entering at least three characters in the input box. The search should be case insensitive and order independent of the words entered into the input box. The results of the food search may be grouped in categories such as My Foods, Popular Foods or Miscellaneous Foods. Within each group in the search results, the foods should be listed first with foods that start with the search string and then alphabetically. After selecting a food item, the user selects the portion size of the selected food. The portion size and the measure depend upon the food selected, e.g., item, serving, gram, ounce. Meal information can also be edited after it is entered. The user may enter as many different meals per day as they choose including breakfast, after breakfast snack, lunch, after lunch snack, dinner and after dinner snack. The system may also automatically populate the user's database of custom foods with the entries from their selected meal plan. This will provide a simple method for the user to track what they have consumed and also a self reported way of tracking compliance with the program.

Figure 8:
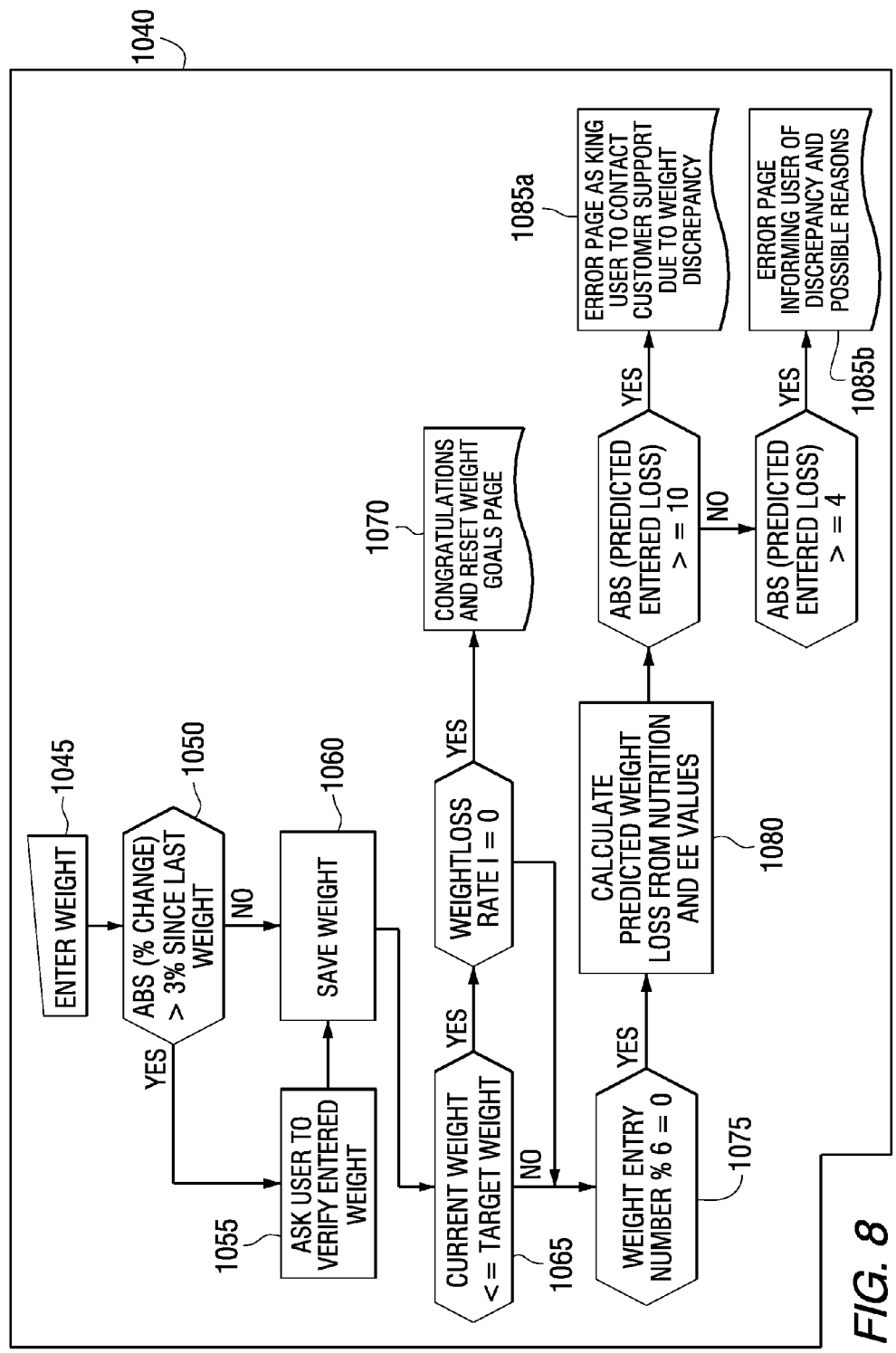
FIG. 8 is a block diagram of a preferred embodiment of the weight tracking system according to an aspect of the present invention.

FIG. 8 is a block diagram illustrating a weight tracking subsystem 1040 which allows a user to record weight changes over time and receive feedback. A user enters an initial weight entry 1045 into the weight tracking subsystem 1040. The weight tracking subsystem 1040 calculates the percent weight change 1050 since the last time the user has made a weight entry. If a newly entered weight is more than 3% above or below the last weight, a weight verification page 1055 is displayed for the user to confirm that the entered weight is correct. If the entered weight is not more than 3% above or below the last weight, the weight tracking subsystem 1040 saves the entry as the current weight 1060. It is to be specifically noted that the weight tracking subsystem 1040 may utilize body fat measurements and calculations in addition to, or in substitution for, the weight entry 1045.

The current weight 1060 is compared to the target weight selected by the user through a weight loss comparison 1065. If a weight is entered which is equal to or below the goal weight, a congratulatory page 1070 displays which has fields for resetting the goal weight. In the preferred embodiment, a comparison is made every six entries between the current weight x and the $(x-6)^{th}$ weight to determine an interval weight loss 1075. Based on the information provided by the user in the registration process regarding weight loss goals, in addition to the input of the user through use of the system, an expected weight loss 1080 is calculated based on these nutritional and energy expenditure values. If interval weight loss 1075 between the two weights is greater than 10 or more pounds from the preprogrammed expected weight loss 1080, the user may be directed to a weight discrepancy error page 1085a directing the user to contact technical support. If the difference between the two weights if four pounds or more, the user may be directed a second weight discrepancy error page 1085b displaying a list of potential reasons for the discrepancy.

Another aspect of the weight tracking subsystem is the estimation of the date at which the user's weight should equal the defined goal value input by the user during the registration or as updated at a later time. An algorithm calculates a rate of weight change based on the sequence of the user's recorded weight entries. A Kalman smoother is applied to the sequence to eliminate the effects of noise due to scale imprecision and day to day weight variability. The date at which the user will reach their weight goal is predicted based on the rate of weight change.

The total energy expenditure of the user can be estimated either by using the apparatus or by manually entering the duration and type of activities. The apparatus automates the estimation process to speed up and simplify data entry, but it is not required for the use of the system. It is known that total body metabolism is measured as total energy expenditure (TEE) according to the following equation:

$$TEE=BMR+AE+TEF+AT,$$

wherein BMR is basal metabolic rate, which is the energy expended by the body during rest such as sleep; AE is activity energy expenditure, which is the energy expended during physical activity; TEF is thermic effect of food, which is the energy expended while digesting and processing the food that is eaten; and AT is adaptive thermogenesis, which is a mechanism by which the body modifies its metabolism to extreme temperatures. It is estimated that it costs humans about 10% of the value of food that is eaten to process the food. TEF is therefore estimated to be 10% of the total calories consumed. Thus, a reliable and practical method of measuring TEF would enable caloric consumption to be measured without the need to manually track or record food related information. Specifically, once TEF is measured, caloric consumption can be accurately estimated by dividing TEF by 0.1 (TEF=0.1*Calories Consumed; Calories Consumed=TEF/0.1).

Figure 9:
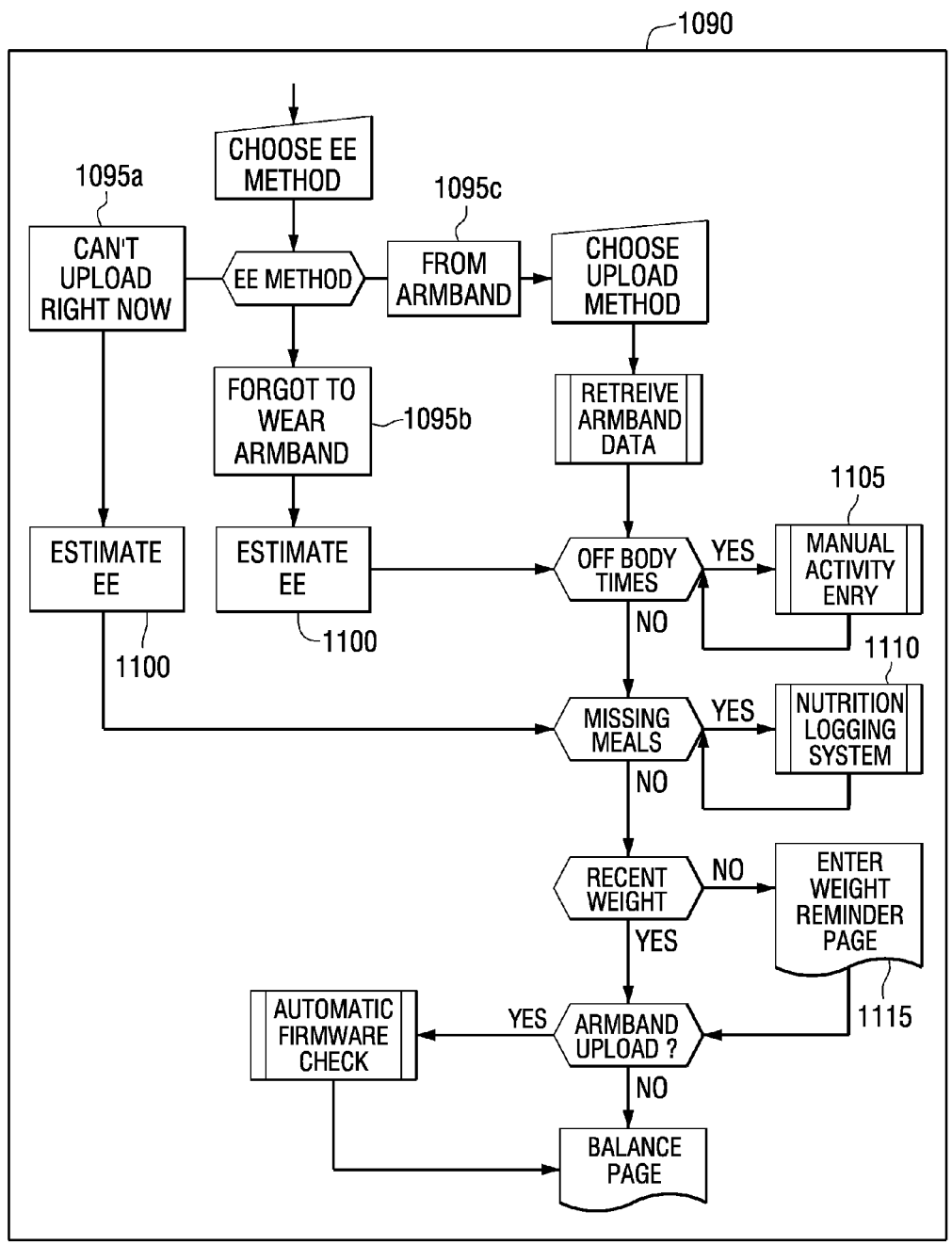
FIG. 9 is a block diagram of a preferred embodiment of the update information wizard interface according to one aspect of the present invention.

FIG. 9 is a block diagram of the update information wizard interface 1090 illustrating the process of data retrieval from the apparatus to update energy expenditure. The user is given at least three options for updating energy expenditure including: an unable to upload armband data option 1095a, a forgot to wear armband data option 1095b, and an upload armband data option 1095c.

When data is retrieved from the apparatus, the system may provide a semi-automated interface. The system is provided with the capability to communicate with the apparatus both wirelessly and with a wired USB connection. The system prompts the user to select the mode of communication before the retrieval of data. It is contemplated that the most common usage model may be wireless retrieval. If wireless retrieval is used, a wired connection could be used primarily for field upgrades of the firmware in the armband. Each apparatus is associated with a particular user and the apparatus is personalized so that it cannot be interchanged between different users.

The system will use the data collected by the armband for estimating the total energy expenditure. This value is calculated using an algorithm contained within the software. The database stores the minute-by-minute estimates of the energy expenditure values, the number of steps, the amount of time the apparatus was worn, the active energy expenditure values, the user's habits, which, in the preferred embodiment are stored as typical hourly non-physically active energy expenditure, their reported exercise while not wearing the apparatus, and the time spent actively.

Referring again to FIG. 9, if the user selects the unable to upload armband data option 1095*a* or the forgot to wear armband option 1095*b*, the user may elect the estimate energy expenditure option 1100, If the user selects the upload armband data option 1095*c*, the user may begin retrieving the data from the apparatus. If the apparatus was worn intermittently or not worn for a period of time, the system can provide the user with a manual activity entry option 1105 to manually enter the type of activity they have engaged in during this period. The options available include a sedentary option, a list of activities from the American College of Sports Medicine Metabolic Equivalent Table and a list of activities previously entered during the use of the device. Over time, the options may be presented in order of highest to lowest incidence, speeding the data input by placing the most frequent options at the top of the list. Additionally, the system may observe patterns of activity based upon time of day, day of the week and the like and suggest an activity with high probability for the particular missing time period. If nothing was entered for activities, the system will estimate the user's energy expenditure using their previously stored data. In the preferred embodiment, this is done using a histogram estimation and analysis incorporating a set of hourly data sets, each of which includes a running average of the non-exercise energy expenditure recorded by the apparatus.

Additionally, the user may select a exercise calculator to estimate the calories burned during any particular activity in the database. The user selects the appropriate activity from a list and a time period for the activity. The system calculates the approximate calories that would be burned by the user during that time period, based upon either or both of (i) a lookup table of average estimate data or (ii) prior measurements for that user during those specific activities.

According to an aspect of the present invention, the armband may detect when the user is physically active and sedentary. During the physically active times, the usage patterns are not updated. Instead the user is asked to report on their highly active periods. During the non-physically active times, the usage pattern is updated and the information gathered is then used during reported sedentary time when the user did not wear the armband.

The system, either through the software platform, the body monitor, or both, can improve its performance in making accurate statements about the wearer by gathering and analyzing data, finding patterns, finding relations, or correlating data about the person over time. For example, if the user gives explicit feedback, such as time stamping a particular activity to the system, the system can this to directly improve the system's ability to identify that activity. As another example, the system can build a characterization of an individual's habits over time to further improve the quality of the derived measures. For example, knowing the times a user tends to exercise, for how long they tend to exercise, or the days they tend not to exercise can all be valuable inputs to the prediction of when physical activity is occurring.

It will be obvious to one skilled in the art that the characterizations of habits and detected patterns are themselves possible derived parameters. Furthermore, these characterizations of habits and patterns can allow the system to be intuitive when the sensors are not working or the apparatus is not attached to the user's body. For example, if the user does not wear the apparatus and measured energy expenditure is not available, or neglects to input a meal, the data can be estimated from the characterizations of habits and prior observed meals and activities, as stated more fully herein.

For the more general embodiment, the Activity Level category of Health Index 155 is designed to help users monitor how and when they move around during the day and utilizes both data input by the user and data sensed by sensor device 10. The data input by the user may include details regarding the user's daily activities, for example the fact that the user worked at a desk from 8 a.m. to 5 p.m. and then took an aerobics class from 6 p.m. to 7 p.m. Relevant data sensed by sensor device 10 may include heart rate, movement as sensed by a device such as an accelerometer, heat flow, respiration rate, calories burned, GSR and hydration level, which may be derived by sensor device 60 or central monitoring unit 30. Calories burned may be calculated in a variety of manners, including: the multiplication of the type of exercise input by the user by the duration of exercise input by the user; sensed motion multiplied by time of motion multiplied by a filter or constant; or sensed heat flux multiplied by time multiplied by a filter or constant.

The Activity Level Health Index piston level is preferably determined with respect to a suggested healthy daily routine that includes: exercising aerobically for a pre-set time period, preferably 20 minutes, or engaging in a vigorous lifestyle activity for a pre-set time period, preferably one hour, and burning at least a minimum target number of calories, preferably 205 calories, through the aerobic exercise and/or lifestyle activity. The minimum target number of calories may be set according to information about the user, such as sex, age, height and/or weight. Parameters utilized in the calculation of the relevant piston level include the amount of time spent exercising aerobically or engaging in a vigorous lifestyle activity as input by the user and/or sensed by sensor device 10, and the number of calories burned above pre-calculated energy expenditure parameters.

Figure 10:
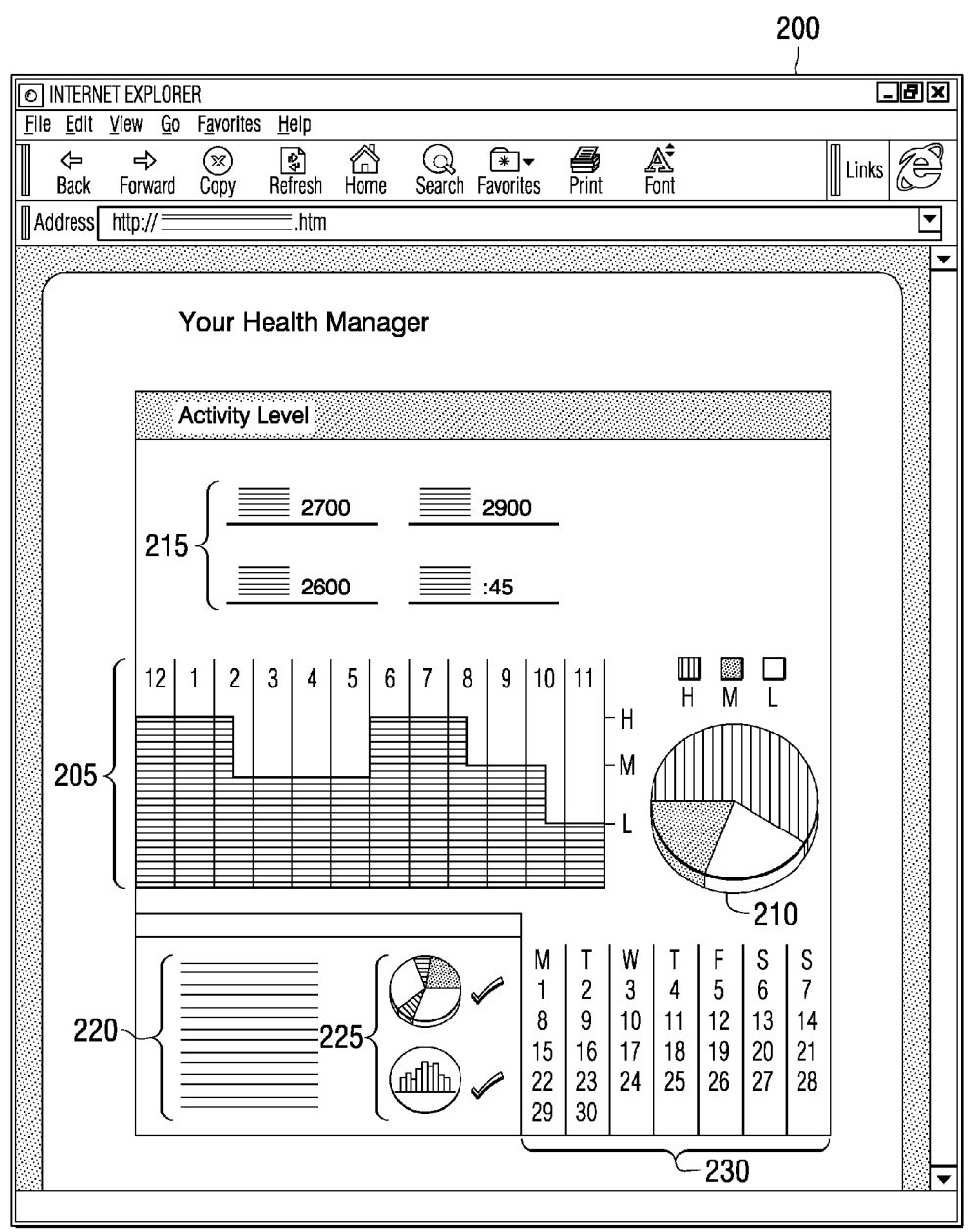
FIG. 10 is a representation of a preferred embodiment of the activity level web page according to an aspect of the present invention.
Figure 11:
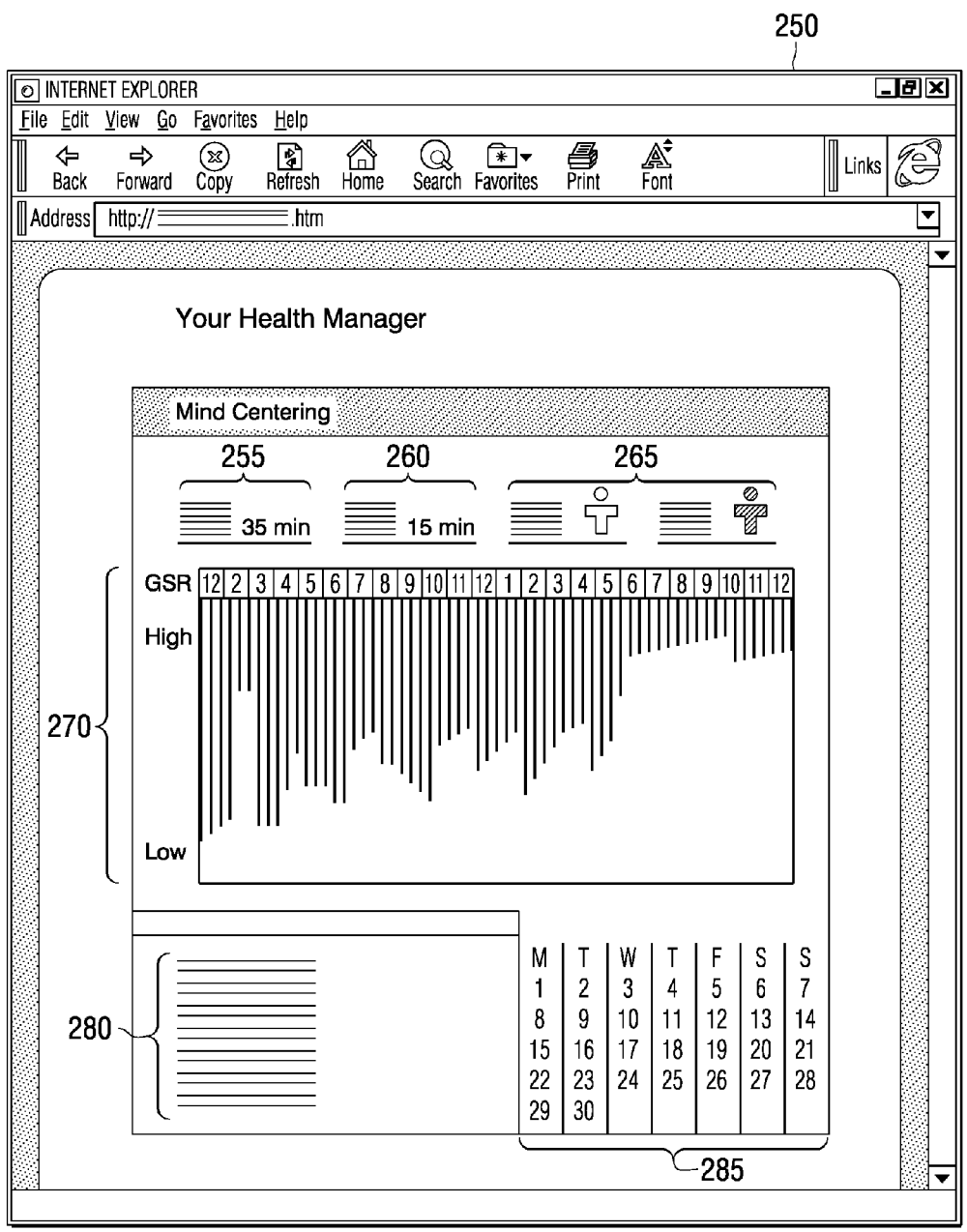
FIG. 11 is a representation of a preferred embodiment of the mind centering web page according to an aspect of the present invention.

Information regarding the individual user's movement is presented to the user through activity level web page 200 shown in FIG. 10, which may include activity graph 205 in the form of a bar graph, for monitoring the individual user's activities in one of three categories: high, medium and low intensity with respect to a pre-selected unit of time. Activity percentage chart 210, in the form or a pie chart, may also be provided for showing the percentage of a pre-selected time period, such as one day, that the user spent in each category. Activity level web page 200 may also include calorie section 215 for displaying items such as total calories burned, daily target calories burned, total caloric intake, and duration of aerobic activity. Finally, activity level web page 200 may include at least one hyperlink 220 to allow a user to directly access relevant news items and articles, suggestions for refining or improving daily routine with respect to activity level and affiliate advertising elsewhere on the network. Activity level web page 200 may be viewed in a variety of formats, and may include user-selectable graphs and charts such as a bar graph, pie chart, or both, as selectable by Activity level check boxes 225. Activity level calendar 230 is provided for selecting among views having variable and selectable time periods. The items shown at 220 may be selected and customized based on information learned about the individual in the survey and on their performance as measured by the Health Index.

The Mind Centering category of Health Index 155 is designed to help users monitor the parameters relating to time spent engaging in certain activities which allow the body to achieve a state of profound relaxation while the mind becomes focused, and is based upon both data input by the user and data sensed by the sensor device 10. In particular, a user may input the beginning and end times of relaxation activities such as yoga or meditation. The quality of those activities as determined by the depth of a mind centering event can be measured by monitoring parameters including skin temperature, heart rate, respiration rate, and heat flow as sensed by sensor device 10. Percent change in GSR as derived either by sensor device 10 or central monitoring unit 30 may also be utilized.

The Mind Centering Health Index piston level is preferably calculated with respect to a suggested healthy daily routine that includes participating each day in an activity that allows the body to achieve profound relaxation while the mind stays highly focused for at least fifteen minutes. Parameters utilized in the calculation of the relevant piston level include the amount of time spent in a mind centering activity, and the percent change in skin temperature, heart rate, respiration rate, heat flow or GSR as sensed by sensor device 10 compared to a baseline which is an indication of the depth or quality of the mind centering activity.

Information regarding the time spent on self-reflection and relaxation is presented to the user through mind centering web page 250 shown in FIG. 1*l*. For each mind centering activity, referred to as a session, the preferred mind centering web page 250 includes the time spent during the session, shown at 255, the target time, shown at 260, comparison section 265 showing target and actual depth of mind centering, or focus, and a histogram 270 that shows the overall level of stress derived from such things as skin temperature, heart rate, respiration rate, heat flow and/or GSR. In comparison section 265, the human figure outline showing target focus is solid, and the human figure outline showing actual focus ranges from fuzzy to solid depending on the level of focus. The preferred mind centering web page may also include an indication of the total time spent on mind centering activities, shown at 275, hyperlinks 280 which allow the user to directly access relevant news items and articles, suggestions for refining or improving daily routine with respect to mind centering and affiliate advertising, and a calendar 285 for choosing among views having variable and selectable time periods. The items shown at 280 may be selected and customized based on information learned about the individual in the survey and on their performance as measured by the Health Index.

The Sleep category of Health Index 155 is designed to help users monitor their sleep patterns and the quality of their sleep. It is intended to help users learn about the importance of sleep in their healthy lifestyle and the relationship of sleep to circadian rhythms, being the normal daily variations in body functions. The Sleep category is based upon both data input by the user and data sensed by sensor device 10. The data input by the user for each relevant time interval includes the times the user went to sleep and woke up and a rating of the quality of sleep. As noted in Table 2, the data from sensor device 10 that is relevant includes skin temperature, heat flow, beat-to-beat heart variability, heart rate, pulse rate, respiration rate, core temperature, galvanic skin response, EMG, EEG, EOG, blood pressure, and oxygen consumption. Also relevant is ambient sound and body movement or motion as detected by a device such as an accelerometer. This data can then be used to calculate or derive sleep onset and wake time, sleep interruptions, and the quality and depth of sleep.

The Sleep Health Index piston level is determined with respect to a healthy daily routine including getting a minimum amount, preferably eight hours, of sleep each night and having a predictable bed time and wake time. The specific parameters which determine the piston level calculation include the number of hours of sleep per night and the bed time and wake time as sensed by sensor device 10 or as input by the user, and the quality of the sleep as rated by the user or derived from other data.

Figure 12:
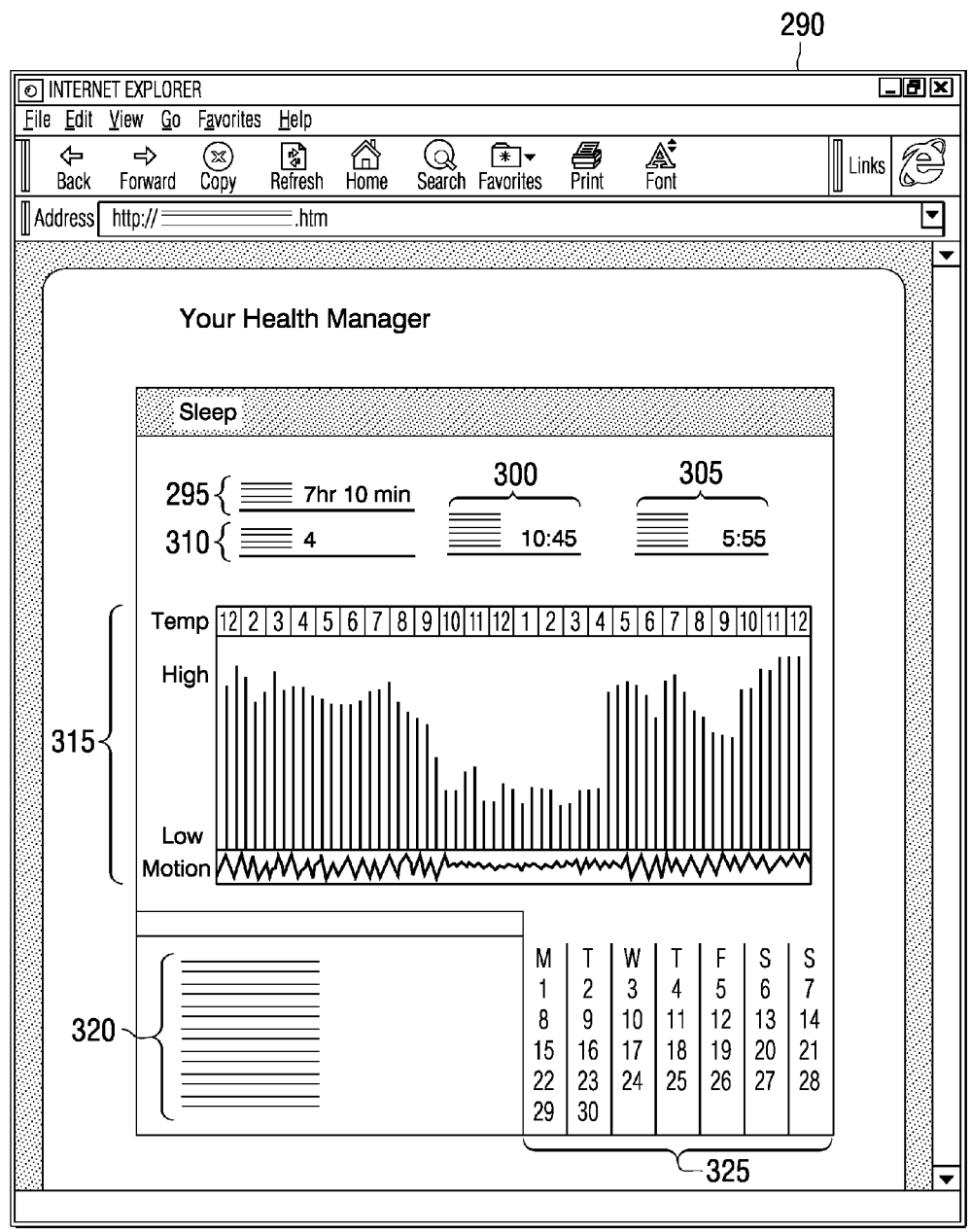
FIG. 12 is a representation of a preferred embodiment of the sleep web page according to an aspect of the present invention.

Information regarding sleep is presented to the user through sleep web page 290 shown in FIG. 12. Sleep web page 290 includes a sleep duration indicator 295, based on either data from sensor device 10 or on data input by the user, together with user sleep time indicator 300 and wake time indicator 305. A quality of sleep rating 310 input by the user may also be utilized and displayed. If more than a one day time interval is being displayed on sleep web page 290, then sleep duration indicator 295 is calculated and displayed as a cumulative value, and sleep time indicator 300, wake time indicator 305 and quality of sleep rating 310 are calculated and illustrated as averages. Sleep web page 290 also includes a user-selectable sleep graph 315 which calculates and displays one sleep related parameter over a pre-selected time interval. For illustrative purposes, FIG. 12 shows heat flow over a one-day period, which tends to be lower during sleeping hours and higher during waking hours. From this informnation, a person's bio-rhythms can be derived. Sleep graph 315 may also include a graphical representation of data from an accelerometer incorporated in sensor device 10 which monitors the movement of the body. The sleep web page 290 may also include hyperlinks 320 which allow the user to directly access sleep related news items and articles, suggestions for refining or improving daily routine with respect to sleep and affiliate advertising available elsewhere on the network, and a sleep calendar 325 for choosing a relevant time interval. The items shown at 320 may be selected and customized based on information learned about the individual in the survey and on their performance as measured by the Health Index.

The Activities of Daily Living category of Health Index 155 is designed to help users monitor certain health and safety related activities and risks and is based in part on data input by the user. Other data which is utilized by the Activities of Daily Living category is derived from the sensor data, in the form of detected activities which are recognized based on physiological and/or contextual data, as described more fully in this application. The Activities of Daily Living category is divided into four sub-categories: personal hygiene, which allows the user to monitor activities such as brushing and flossing his or her teeth and showering; health maintenance, that tracks whether the user is taking prescribed medication or supplements and allows the user to monitor tobacco and alcohol consumption and automobile safety such as seat belt use; personal time, that allows the user to monitor time spent socially with family and friends, leisure, and mind centering activities; and responsibilities, that allows the user to monitor certain work and financial activities such as paying bills and household chores.

The Activities of Daily Living Health Index piston level is preferably determined with respect to the healthy daily routine described below. With respect to personal hygiene, the routine requires that the users shower or bathe each day, brush and floss teeth each day, and maintain regular bowel habits. With respect to health maintenance, the routine requires that the user take medications and vitamins and/or supplements, use a seat belt, refrain from smoking, drink moderately, and monitor health each day with the Health Manager. With respect to personal time, the routine requires the users to spend at least one hour of quality time each day with family and/or friends, restrict work time to a maximum of nine hours a day, spend some time on a leisure or play activity each day, and engage in a mind stimulating activity. With respect to responsibilities, the routine requires the users to do household chores, pay bills, be on time for work, and keep appointments. The piston level is calculated based on the degree to which the user completes a list of daily activities as determined by information input by the user.

Figure 13:
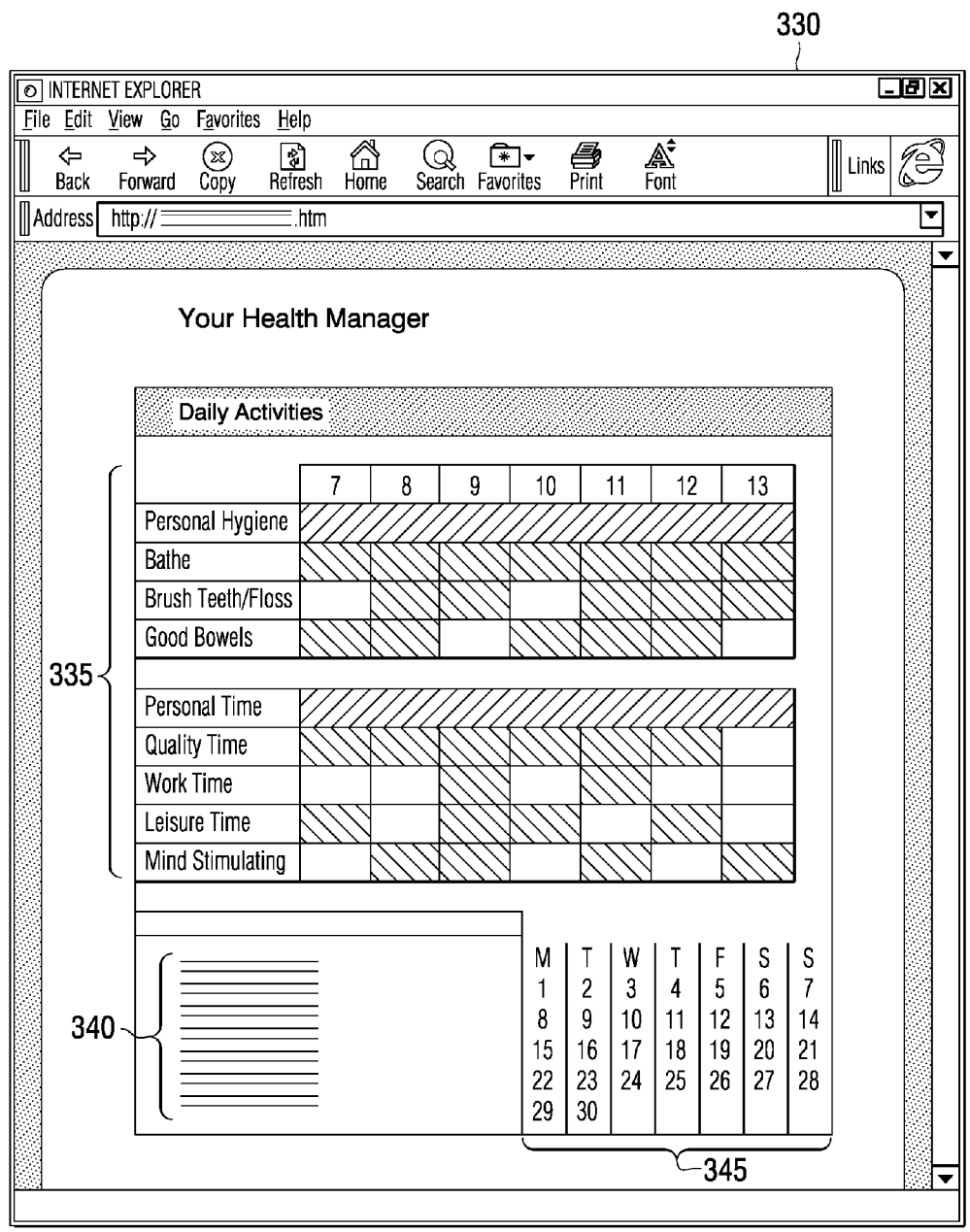
FIG. 13 is a representation of a preferred embodiment of the daily activities web page according to an aspect of the present invention.

Information relating to these activities is presented to the user through daily activities web page 330 shown in FIG. 13. In preferred daily activities web page 330, activities chart 335, selectable for one or more of the sub-categories, shows whether the user has done what is required by the daily routine. A colored or shaded box indicates that the user has done the required activity, and an empty, non-colored or shaded box indicates that the user has not done the activity. Activities chart 335 can be created and viewed in selectable time intervals. For illustrative purposes, FIG. 13 shows the personal hygiene and personal time sub-categories for a particular week. In addition, daily activities web page 330 may include daily activity hyperlinks 340 which allow the user to directly access relevant news items and articles, suggestions for improving or refining daily routine with respect to activities of daily living and affiliate advertising, and a daily activities calendar 345 for selecting a relevant time interval. The items shown at 340 may be selected and customized based on information learned about the individual in the survey and on their performance as measured by the Health Index.

The How You Feel category of Health Index 155 is designed to allow users to monitor their perception of how they felt on a particular day, and is based on information, essentially a subjective rating, that is input directly by the user. A user provides a rating, preferably on a scale of 1 to 5, with respect to the following nine subject areas: mental sharpness; emotional and psychological well being; energy level; ability to cope with life stresses; appearance; physical well being; self-control; motivation; and comfort in relating to others. Those ratings are averaged and used to calculate the relevant piston level.

Figure 14:
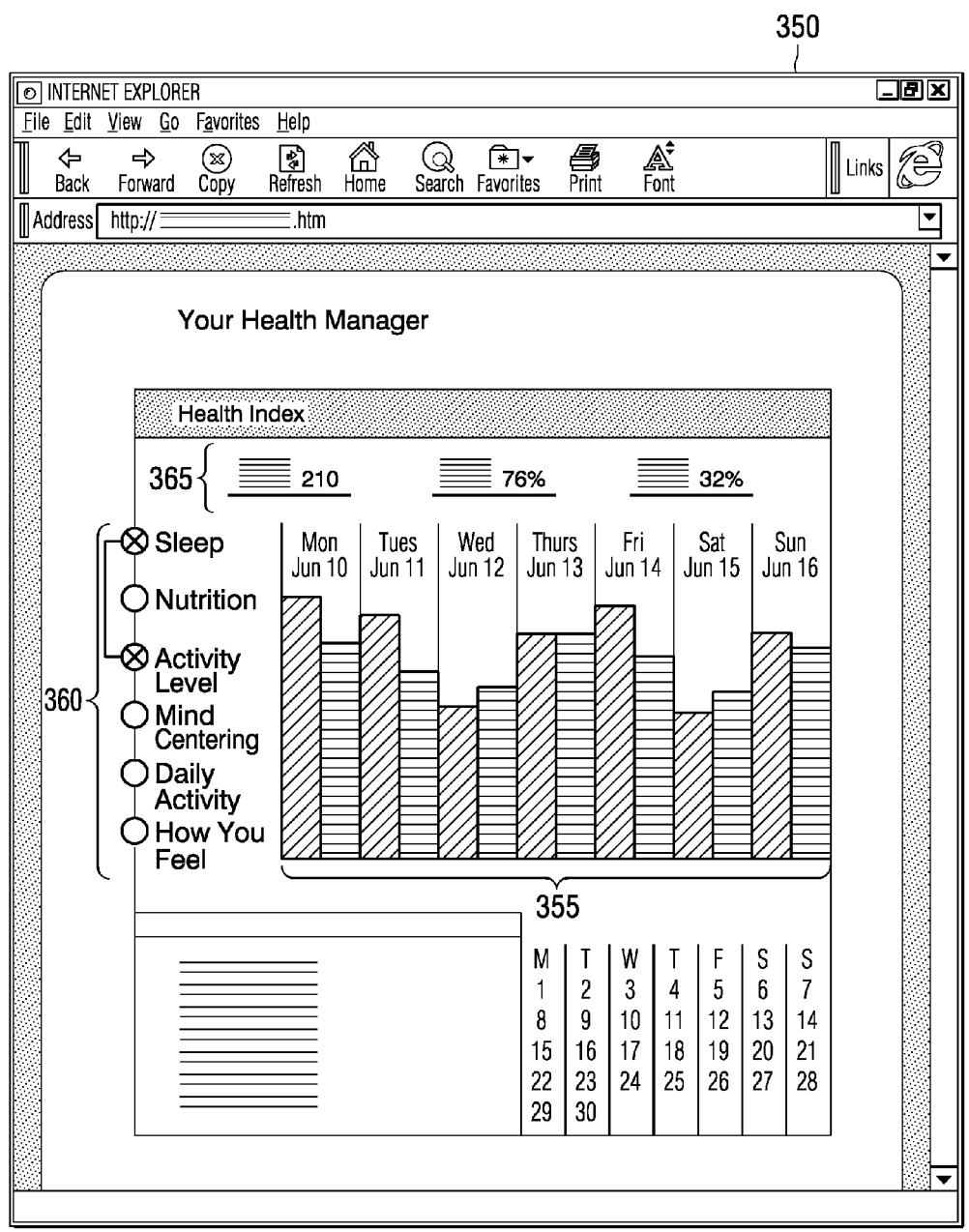
FIG. 14 is a representation of a preferred embodiment of the Health Index web page according to an aspect of the present invention.

Referring to FIG. 14, Health Index web page 350 is shown. Health Index web page 350 enables users to view the performance of their Health Index over a user selectable time interval including any number of consecutive or non-consecutive days. Using Health Index selector buttons 360, the user can select to view the Health Index piston levels for one category, or can view a side-by-side comparison of the Health Index piston levels for two or more categories. For example, a user might want to just turn on Sleep to see if their overall sleep rating improved over the previous month, much in the same way they view the performance of their favorite stock. Alternatively, Sleep and Activity Level might be simultaneously displayed in order to compare and evaluate Sleep ratings with corresponding Activity Level ratings to determine if any day-to-day correlations exist. Nutrition ratings might be displayed with How You Feel for a pre-selected time interval to determine if any correlation exists between daily eating habits and how they felt during that interval. For illustrative purposes, FIG. 14 illustrates a comparison of Sleep and Activity Level piston levels for the week of June 10 through June 16. Health Index web page 350 also includes tracking calculator 365 that displays access information and statistics such as the total number of days the user has logged in and used the Health Manager, the percentage of days the user has used the Health Manager since becoming a subscriber, and percentage of time the user has used the sensor device 10 to gather data.

Referring again to FIG. 5, opening Health Manager web page 150 may include a plurality of user selectable category summaries 156a through 156f, one corresponding to each of the Health Index 155 categories. Each category summary 156a through 156f presents a pre-selected filtered subset of the data associated with the corresponding category. Nutrition category summary 156a displays daily target and actual caloric intake. Activity Level category summary 156b displays daily target and actual calories burned. Mind Centering category summary 156c displays target and actual depth of mind centering or focus. Sleep category summary 156d displays target sleep, actual sleep, and a sleep quality rating. Daily Activities category summary 156e displays a target and actual score based on the percentage of suggested daily activities that are completed. The How You Feel category summary 156f shows a target and actual rating for the day.

Opening Health Manager web page 150 also may include Daily Dose section 157 which provides, on a daily time interval basis, information to the user, including, but not limited to, hyperlinks to news items and articles, commentary and reminders to the user based on tendencies, such as poor nutritional habits, determined from the initial survey. The commentary for Daily Dose 157 may, for example, be a factual statement that drinking 8 glasses of water a day can reduce the risk of colon cancer by as much as 32%, accompanied by a suggestion to keep a cup of water by your computer or on your desk at work and refill often. Opening Health Manager web page 150 also may include a Problem Solver section 158 that actively evaluates the user's performance in each of the categories of Health Index 155 and presents suggestions for improvement. For example, if the system detects that a user's Sleep levels have been low, which suggest that the user has been having trouble sleeping, Problem Solver 158 can provide suggestions for way to improve sleep. Problem Solver 158 also may include the capability of user questions regarding improvements in performance. Opening Health Manager web page 150 may also include a Daily Data section 159 that launches an input dialog box. The input dialog box facilitates input by the user of the various data required by the Health Manager. As is known in the art, data entry may be in the form of selection from pre-defined lists or general free form text input. Finally, opening Health Manager web page 150 may include Body Stats section 161 which may provide information regarding the user's height, weight, body measurements, body mass index or BMI, and vital signs such as heart rate, blood pressure or any of the identified physiological parameters.

Referring again to the weight management embodiment, energy balance is utilized to track and predict weight loss and progress. The energy balance equation has two components, energy intake and energy expenditure, and the difference between these two values is the energy balance. Daily caloric intake equals the number of calories that a user consumes within a day. Total energy expenditure is the amount of calories expended by a user whether at rest or engaging in any type of activity. The goal of the system is to provide a way to track daily caloric intake and automatically monitor total energy expenditure accurately so users can track their status and progress with respect to these two parameters. The user is also provided with feedback regarding additional activities necessary to achieve their energy balance. To achieve weight loss the energy balance should be negative which means that fewer calories were consumed than expended. A positive energy balance has the potential to result in weight gain or no loss of weight. The management system automates the ability of the user to track energy balance through the energy intake tracking subsystem, the energy expenditure tracking subsystem and the energy balance and feedback subsystem.

Referring again to FIG. 9, if the user has not entered any meals or food items consumed since the last update, the user will be prompted to initiate the energy intake subsystem 1110 to log caloric intake for the appropriate meals. The energy intake subsystem may estimate the average daily caloric intake of the user using the total energy expenditure estimate and the change in the user's weight and/or body fat composition. The inputs to this system include the user's body fat composition or weight, at regular intervals related to the relevant time period, and the energy expenditure estimation. If the user has not updated their weight within the last 7 days, they will be directed to a weight reminder page 1115. The energy expenditure estimation is based on the basic equivalence of 3500 kcal equal to a 1 lb change in weight. The software program will also attempt to smooth the estimation by accounting for fluctuations in water retained by the body and for differences in the way the user has collected weight readings, e.g. different times of the day or different weight scales.

It is to be specifically noted that the system may also be utilized to derive the caloric intake from the energy expenditure of the user and the changes in weight which are input by the user or otherwise detected by the system. This is accomplished by utilizing the same basic calculations described herein, however the net weight gain or loss is utilized as the reference input. In the equation A+B=C, A is equal to caloric intake, B equal to energy expenditure and C equal to the net weight gain or loss. The system may not be able to determine the specific information regarding the type of food items consumed by the user, but it can calculate what the caloric intake for the user would be, given the known physiological parameters and the energy expenditure measured during the relevant time period. Changes in body fat and water weight may also be incorporated into this calculation for greater accuracy.

This calculation of daily caloric intake may also be performed even when the user is entering nutritional information as a check against the accuracy of the data input, or to tune the correlation between the small, medium and large size meal options described above, in the more simplified method of caloric input, and the actual calorie consumption of the user, as is disclosed in co-pending U.S. patent application Ser. No. 10/682,759, the specification of which is incorporated herein by reference. Lastly, this reverse calculation can be utilized in the institutional setting to determine whether or to what degree the patients are consuming the meals provided and entered into the system.

Logging of the foods consumed is completely optional for the user. By using this feature the user can get feedback about how much food they think they consumed compared to what they actually consumed, as measured by the energy intake estimation subsystem described above. If the user chooses to log food intake, a semi automated interface guides the user through the breakfast, after breakfast snack, lunch, after lunch snack, dinner, and after dinner snack progression. If the user does not have the need to enter any data, e.g., the user did not have a snack after breakfast, options may be provided to skip the entry. Immediate feedback about the caloric content of the selected foods also may be provided.

For any of the 6 meal events, the software assumes one of the following scenarios to be true: a user has eaten the meal and wants to log in what they ate food by food; a user has eaten the meal but has eaten the same thing as a previous day; a user has eaten the meal but can not recall what they ate; a user has eaten the meal, can recall what they ate, but does not want to enter in what they ate food by food; a user has skipped the meal; a user has not eaten the meal yet. The software forces the user to apply these scenarios for each meal chronologically since the last meal event was entered into the system. This ensures there are no gaps in the data. Gaps in the data lead to misleading calculations of calorie balance.

If the user wants to log food items, the software responds by prompting the user to type in the first few letters of a food into the dynamic search box which automatically pulls the closest matches from the food database into a scrollable drop down list just below the entry. Upon selection of an entry, the food appears in a consumed foods list to the right of the drop down, where addition of information such as unit of measure and serving size can be edited, or the food can be deleted from the consumed foods list. The total number of calories per meal is automatically calculated at the bottom of the consumed foods list. This method is repeated until the meal has been recounted. In the event that a food does not exist in the database, a message appears in the drop down box suggesting that the user can add a custom food to their personal database.

If a user has eaten the same thing as a previous day, the user selects the appropriate day and the meal chosen appears to the right. The user hits the next button to enter it into the system. This specifically capitalizes on the tendency of people to have repetitive eating patterns such as the same foods for the same meals over increments of time.

If a user cannot recall a meal, the software responds by bringing up a screen that calculates an average of the total number of calories consumed for that meal over a certain number of days and presents that number to the user.

If the user has eaten a meal, but does not want to enter the consumed food items, the software may bring up a screen that enables the user to quickly estimate caloric intake by either entering a number of calories consumed or selecting a word amount such as normal, less than normal, more than normal, a lot or very little. Depending on the selection, estimated caloric intake increases or decreases from the average, or what is typical based on an average range. For example, if on average the user consumes between 850 and 1000 kcal for dinner, and specifies that for the relevant meal that he ate more than usual, the estimate may be higher than 1000 kcal.

If a user specifies that they did not eat a certain meal yet, they may choose to proceed to the weight management center. This accounts for the fact that users eat meals at different points of the day, but never one before the other.

To keep the amount of time a user has to spend entering the meal information to a minimum, the system may also offer the option to select from a list of frequently consumed foods. The user can select food items from the frequent foods list and minimize the need to search the database for commonly consumed foods. The frequent foods tool is designed to further expedite the task of accurately recalling and entering food consumption. It is based on the observation that people tend to eat only 35-50 unique foods seasonally. People tend to eat a core set of favorite breakfast foods, snacks, side dishes, lunches, and fast food based on personal preference, and issues concerning convenience, like places they can walk or drive to from work for lunch. The frequent foods tool works by tallying the number of times specific food entries are selected from the database by the user for each of the six daily meal events. The total number of selections of a specific food entry is recorded, and the top foods with the most selections appears in a frequent foods list in order of popularity. Additionally, the system is also aware of other meal related parameters of the user, such as meal plan or diet type, and speeds data entry by limiting choices or placing more relevant foods at the top of the lists.

Figure 15:
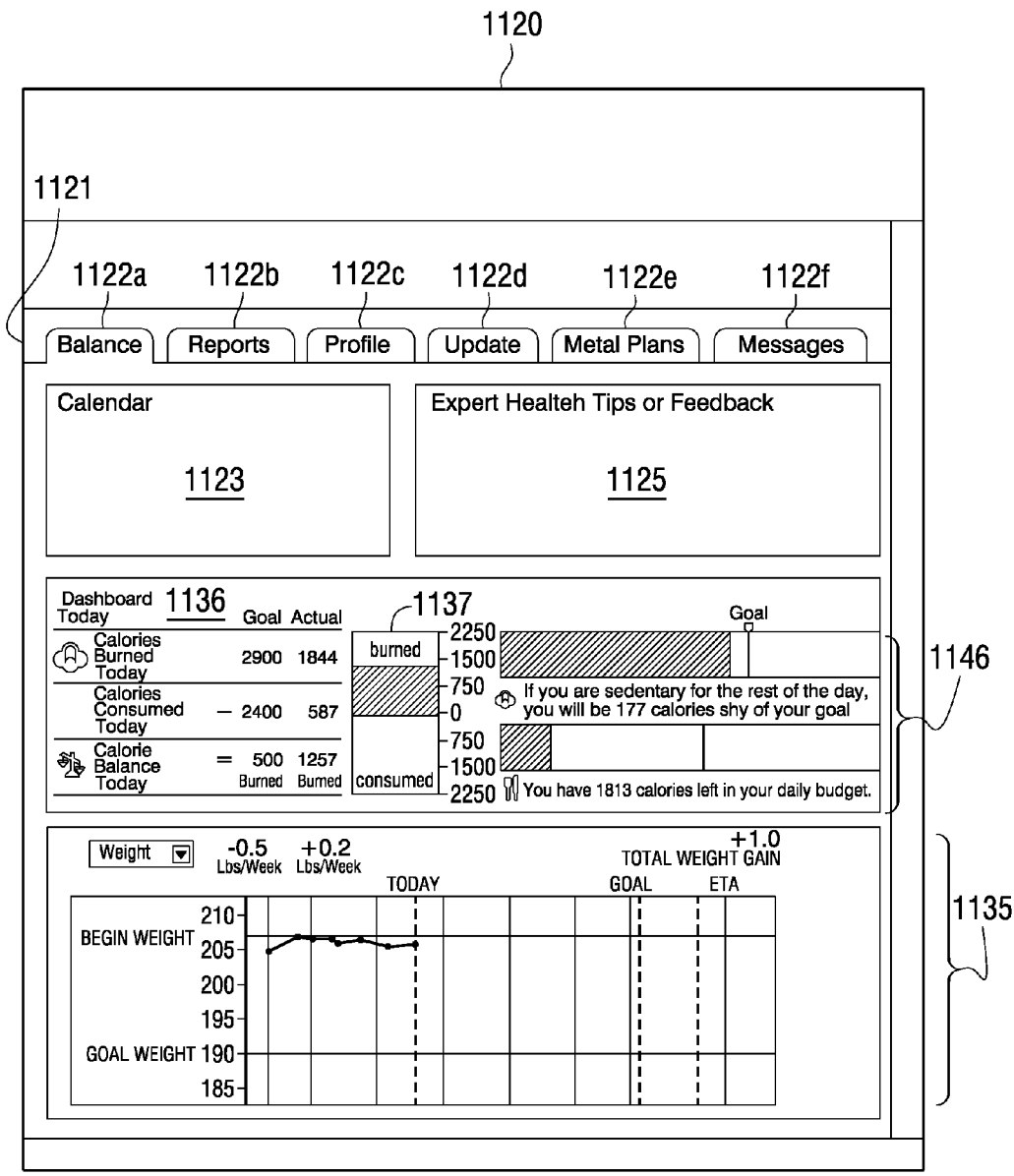
FIG. 15 is a representation of a preferred embodiment of the Weight Manager interface according to an aspect of the present invention.

FIG. 15 is a representation of a preferred embodiment of the Weight Manager interface 1120. Weight Manager interface 1120 is provided with a multi section screen having a navigation bar 1121 which comprises a series of subject matter tabs 1122. The tabs are customizable with the program but typically include sections for report writing and selection 1122*b*, a navigation tab to the user's profile 1122*c*, a navigation tab to the armband sensor device update section 1122*d*, a navigation tab to the meal entry section 1122*e* and a message section 1122*f*. The interface 1120 is further provided, as shown in FIG. 15, with an operational section 1122*a* entitled balance which comprises the primary user functions of the Weight Manager interface 1120. A calendar section 1123 provides the user with the ability to select and view data from or for any particular date. A feedback section 1125 provide commentary as described herein, and a dashboard section 1126 provides graphical output regarding the selected days energy intake and expenditure. Finally, a weight loss progress section 1135 provides a graphical output of weight versus time for any given date selected in calendar section 1123.

A feedback and coaching engine analyzes the data generated by the total energy expenditure and daily caloric intake calculations, as previously discussed, to provide the user with feedback in the feedback section 1125. The feedback may present a variety of choices depending on the current state of the progress of the user. If the user is both losing weight and achieving the target daily caloric intake and total energy expenditure goals, they are encouraged to continue the program without making any adjustments. If the user is not losing weight according to the preset goals, the user may be presented with an option to increase the total energy expenditure, decrease the daily caloric intake, combination of increase in total energy expenditure and decrease in daily caloric intake to reach energy balance goals or reset goals to be more achievable. The feedback may further include suggestions as to meal and vitamin supplements. This feedback and coaching may also be incorporated in the intermittent status reports described below, as both present similar information.

If the user chooses to decrease daily caloric intake the user may be presented with an option to generate a new meal plan to suit their new daily caloric goal. If the user chooses to increase total expenditure energy goal, the user may be presented with an exercise plan to guide them to the preset goals. A total energy expenditure estimation calculator utility may also be available to the users. The calculator utility may enable the user to select from multiple exercise options. If the user chooses to increase total energy expenditure and decrease daily caloric intake to reach the preset goals, the meal plan and exercise choices may be adjusted accordingly. Safety limitations may be placed on both the daily caloric intake and total energy expenditure recommendations. For example, a meal plan with fewer than 1200 kcal a day and exercise recommendations for more than an hour a day may not be recommended based on the imposed safety limitations.

Additionally, the user may be provided with suggestions for achieving a preset goal. These suggestions may include simple hints, such as to wear their armband more often, visit the gym more, park farther from the office, or log food items more regularly, as well as specific hints about why the user might not be seeing the expected results.

In an alternative embodiment, the recommendations given by the coaching engine are based on a wider set of inputs, including the past history of recommendations and the user's physiological data. The feedback engine can optionally engage the user in a serious of questions to elicit the underlying source for their failure to achieve a preset goal. For example, the system can ask questions including whether the user had visitors, was the user out of town over the weekend, was the user too busy to have time to exercise, or if the user dine out a lot during the week. Asking these questions gives the user encouragement and helps the user understand the reasons that a preset goal has not been achieved.

Another aspect of this alternative embodiment of the feedback system is that the system can evaluate the results of giving the feedback to the user. This is accomplished through the tracking of the parameters which are the subject of the feedback, such as context and estimated daily caloric intake or logged intake. This feature enables the system to be observational and not just result based, because it can monitor the nature of compliance and modify the feedback accordingly. For example, if the system suggests eating less, the system can measure how much less the user eats in the next week and use this successful response as feedback to tune the system's effectiveness with respect to the user's compliance with the original feedback or suggestions.

Other examples of such delayed feedback for the system are whether the user exercises more when the system suggests it, whether the user undertakes more cardiovascular exercise when prompted to, and whether the user wears the armband more when it is suggested. This type of delayed feedback signal, and the system's subsequent adaptation thereto is identified as reinforcement learning, as is well known in the art. This learning system tunes the behavior of a system or agent based on delayed feedback signals.

In this alternate embodiment, the system is tuned at three levels of specificity through the reinforcement learning framework. First, the feedback is adapted for the entire population for a given situation, e.g. what is the right feedback to give when the user is in a plateau. Second, the feedback is adapted for groups of people, e.g. what is the right feedback in situation X for people like person Y or what is the right feedback for women when the person hasn't been achieving intake goals for three weeks, which may be different from the nature or character or tone of the feedback given to men under the same conditions. Finally, the system can also adapt itself directly based on the individual, e.g. i.e., what is the best feedback for this particular user who has not exercised enough in a given week.

In another aspect of the invention, the feedback provided to the user might be predictive in nature. At times, an individual may experience non-goal or negatively oriented situations, such as weight gain, during a weight loss regimen. The situations may also be positive or neutral. Because of the continuous monitoring of data through the use of the system, the events surrounding, that is, immediately prior and subsequent to, the situation can be analyzed to determine and classify the type of event. The sequence of events, readings or parameters can be recorded as a pattern, which the system can store and review. The system can compare current data regarding this situation to prior data or patterns to determine if a similar situation has occurred previously and further to predict if a past episode is going to occur in the near term. The system may then provide feedback regarding the situation, and, with each occurrence, the system can tailor the feedback provided to the user, based on the responses provided by or detected from the user. The system can further tailor the feedback based on the effectiveness of the feedback. As the system is further customized for the user, the system may also proactively make suggestions based on the user's detected responses to the feedback. For example, in the situation where a user has reached a plateau in weight management, the system may formulate new suggestions to enable a user to return to a state of progress.

Furthermore, the system modifies the reinforcement learning framework with regard to detected or nondetected responses to the provided feedback. For example, if the system suggests that the user should increase their energy expenditure, but the individual responds by wearing the armband more often, the system can modify the framework based on the user's sensitivities to the feedback. The reinforcement is not only from the direct interaction of the user with the system, but also any difference in behavior, even if the connection is not immediately obvious.

It should be specifically noted that the predictive analysis of the data regarding negatively positively or neutrally oriented situations may be based on the user's personal history or patterns or based on aggregate data of similar data from other users in the population. The population data may be based on the data gathered from users of any of the embodiments of the system, including but not limited to weight management.

Moreover, as the user experiences multiple occasions of similar situations, the system may begin to understand how the individual arrived at this stage and how the person attempted to correct the situation, successfully or unsuccessfully. The system reinforces its learning and adaptation through pattern matching to further modify future feedback the next time this situation may occur. For example, it is not uncommon in weight management for a user to experience a plateau, which is the slowing of the user's metabolism to slow in order to conserve calories and also a period during which a user may not realize any progress toward preset goals. Also, occasions may occur which cause the user to deviate from a preset goal either temporarily or long-term such as long weekends, vacations, business trips or periods of consistent weather conditions, the system may provide reminders prior to the plateau or the event, warning of an impending problem and providing suggestions for avoidance.

In an alternate embodiment, when the user experiences a negative, positive or neutral situation that is likely to affect achieved progress, the system may display the risk factors discussed above as they are affected by the situation. For example, if the user has experienced a negative situation that has caused an increase in weight, the system may determine that the user's risk for heart disease is now elevated. This current elevated risk is displayed accordingly in the risk factor bar for that condition and compared to the risk at the user's goal level.

It will be clear to one skilled in the art that the description just given for guiding a person through an automated process of behavior modification with reinforcement with respect to a series of physiologic and/or contextual states of the individual's body and their previous behavior responses, while described for the specific behavior modification goal of weight management, need not be limited to that particular behavior modification goal. The process could also be adapted and applied without limitation to sleep management, pregnancy wellness management, diabetes disease management, cardiovascular disease management, fitness management, infant wellness management, and stress management, with the same or other additional inputs or outputs to the system.

Equally appreciable is a system in which a user is a diabetic using the tool for weight management and, therefore, insulin level and has had a serious or series of symptoms or sudden changes in blood glucose level recorded in the data. In this embodiment, the inputs would be the same as the weight embodiment, calories ingested, types of calories, activity and energy expenditure and weight. With respect to the insulin level, management where the feedback of this system was specifically tuned for predicted body insulin levels, calorie intake, calorie burn, activity classifications and weight measurement could be utilized. User input would include glucometer readings analogous to the weight scale of the weight loss embodiment. It should be noted that insulin level is indirectly related to energy balance and therefore weight management. Even for a non-diabetic, a low insulin level reflects a limitation on energy expenditure, since the body is unable to obtain its maximum potential.

In addition to monitoring of physiological and contextual parameters, environmental parameters may also be monitored to determine the effect on the user. These parameters may include ozone, pollen count, and humidity and may be useful for, but not limited to, a system of asthma management.

There are many aspects to the feedback that can be adapted in different embodiments of this system. For example, the medium of the feedback can be modified. Based on performance, the system can choose to contact the user through phone, email, fax, or the web site. The tone or format of the message itself can be modified, for example by choosing a strong message delivered as a pop-up message. A message such as "You've been too lazy! I'm ordering you to get out there and exercise more this week" or a more softly toned message delivered in the feedback section of the site, such as "You've been doing pretty well,. but if you can find more time to exercise this week, you'll stay closer to your targets".

The system may also include a reporting feature to provide a summary of the energy expenditure, daily caloric intake, energy balance or nutritional information for a period of time. The user may be provided with an interface to visualize graphically and analyze the numbers of their energy balance. The input values for the energy balance calculation are the daily caloric intake that was estimated using the total energy expenditure and weight or body fat changes and total energy expenditure estimates based on the usage of the energy expenditure tracking system. The user may be provided with this information both in an equation form and visually. Shortcuts are provided for commonly used summary time periods, such as daily, yesterday, last 7 days, last 30 days and since beginning.

The report can also be customized in various ways including what the user has asked to see in the past or what the user actually has done. The reports may be customized by third party specifications or by user selection. If the user has not exercised, the exercise tab can be left out. The user may ask to see a diary of past feedback to see the type of feedback previously received. If the feedback has all been about controlling daily caloric intake, the reports can be more about nutrition. One skilled in the art will recognize that the reports can be enhanced in all the ways that the feedback engine can be enhanced and can be viewed as an extension of the feedback engine.

Referring again to FIG. 15, the balance tab 1122a presents a summary of the user's weight loss progress in a variety of formats. For the balance section 1122a, a weight loss progress graph 1135 illustrates the user's weight loss progress from day the user began using the total weight loss system to the present date. Energy balance section 1136 provides details regarding the user's actual and goal energy balance including the actual and goal calories consumed and actual and goal calories burned. Energy balance graph 1137 is a graphical representation of this same information. Dashboard section 1126 also has a performance indicator section 1146 which lets the user know the state of their energy balance in relation to their goal. The information contained within the performance indicator section 1146 may be a graphical representation of the information in the feedback section 1125. Optionally, the system may display a list of the particular foods consumed during the relevant time period and the nutritional aspects of the food, such as calories, carbohydrate and fat content in chart form. Similarly, the display may include a charted list of all activities conducted during the relevant time period together with relevant data such as the duration of the activity and the calories burned. The system may further be utilized to log such activities at a user-selected level of detail, including individual exercises, calisthenics and the like.

In an alternative embodiment, the system may also provide intermittent feedback to the user in the feedback section 1125, alone or in conjunction with the feedback and coaching engine. The feedback and coaching engine is a more specific or alternative embodiment of the Problem Solver, as described above. The feedback may also be presented in an additional display box or window, as appropriate, in the form of a periodic or intermittent status report 1140. The intermittent status report 1140 may also be requested by the user at any time. The status report may be an alert located in a box on a location of the screen and is typically set off to attract the user's attention. Status reports and images are generated by creating a key string, or parameter set, based on the user's current view and state and may provide information to the user about their weight loss goal progress. This information typically includes suggestions to meet the user's calorie balance goal for the day.

Intermittent status reports 1140 are generated on the balance tab 1122a of the Weight Manager Interface 1120. The purpose of the intermittent status report 1140 is to provide immediate instructional feedback to the user for the selected view. A properties file containing key value pairs is searched to match message and images which establishes certain selection criteria to the corresponding key.

In the preferred embodiment, there are four possible views for intermittent status reports 1140: Today, Specific Day, Average (Last 7 or 30 Day) and Since Beginning.

A user state is incorporated as part of the selection criteria for intermittent status report 1140. The user state is based on the actual and goal values of energy expenditure and daily caloric intake as previously described. The goal and predicted energy balance based, on the respective energy expenditure and daily caloric intake values, is also utilized as an additional comparison factor in user states 4 and 5. The possible user states are shown in Table 3:

TABLE 3

| State | Description | Calculation |
|---|---|---|
| 1 | A user will not reach energy goal and daily caloric intake is below budget | (energy expenditure < goal energy expenditure) and (daily caloric intake <= goal daily caloric intake) Where = has a tolerance of ± is 50 calories |
| 2 | A user has or will have burned more calories than the goal, and daily caloric intake is below budget | (energy expenditure >= goal energy expenditure) and (daily caloric intake <= goal daily caloric intake) Where = has a tolerance of ± is 50 calories |
| 3 | A user hasn't exercised enough and has eaten too much | (energy expenditure < goal energy expenditure) and (daily caloric intake > goal daily caloric intake) Where = has a tolerance of ± is 50 calories |
| 4 | A user has exceeded caloric intake goals, but energy expenditure should make up for it | (energy expenditure >= goal energy expenditure) and (daily caloric intake > goal daily caloric intake) && (predicted energy balance >= goal energy balance) Where = has a tolerance of ± is 50 calories |
| 5 | A user has exceeded caloric intake goals, but energy expenditure goals will not make up for it | (energy expenditure >= goal energy expenditure) and (daily caloric intake > goal daily caloric intake) && (predicted energy balance < goal energy balance) Where = has a tolerance of ± is 50 calories |

The user's current energy balance is also used to determine part of the selection criteria.

TABLE 4

| String | Calculation |
|---|---|
| Black | (energy expenditure - daily caloric intake) > 40 |
| Even | −40 < (energy expenditure - daily caloric intake) < 40 |
| Red | 40 < (energy expenditure - daily caloric intake) |

The last part of the selection criteria depends on the type of view selected, as previously described above. Specifically, the today view incorporates two parameters to predict the ability of the user to correct the energy balance deficiencies by the end of the relevant time period:

TABLE 5

| String | Description |
|---|---|
| Early | A favorite activity takes less than an hour to correct the energy balance and it is before 11:00 PM; or an activity appropriate for the user will correct the energy balance and enough time remains in the relevant period for its completion. |
| Late | A favorite activity takes more than an hour to correct the energy balance or it is after 11:00 PM; or there is insufficient time to complete an activity which will return a positive result for energy balance. |

All other views use two types of information for estimating the validity of the goals:

TABLE 6

| String | Calculation |
|---|---|
| validgoals | If (state 2 or 4) then 80% > % DCI or % EE > 120% and there is a valid activity to make up the difference in less than an hour else just based on percent |

TABLE 6-continued

| String | Calculation |
|---|---|
| suspectgoals | If (state 2 or 4) then 80% > % DCI or % EE > 120% or there is NOT a valid activity to make up the difference in less than an hour else just based on percent | where % DCI or % EE represents the current percent of daily caloric intake or energy expenditure, as appropriate, in relation to the goal of the user.

A similar method is used to determine the messages below each horizontal bar chart as shown in FIG. 15. The next part of the selection criteria is achievement status, which is determined by the current value of daily caloric intake or energy expenditure in relation to the goal set by the user. The parameters are as follows:

TABLE 7

| String | Calculation |
|---|---|
| above | Value > goal |
| even | Value = goal |
| below | Value < goal |

In alternative embodiments, the representation underlying the method for choosing the feedback could be, but are not limited to being, a decision tree, planning system, constraint satisfaction system, frame based system, case based system rule-based system, predicate calculus, general purpose planning system, or a probabilistic network. In alternative embodiments, another aspect of the method is to adapt the subsystem choosing the feedback. This can be done, for example, using a decision-theoretic adaptive probabilistic system, a simple adaptive planning system, or a gradient descent method on a set of parameters.

With respect to the calculation of energy balance, the armband sensor device continuously measures a person's energy expenditure. During the day the human body is continuously burning calories. The minimal rate that a human body expends energy is called resting metabolic rate, or RMR. For an average person, the daily RMR is about 1500 calories. It is more for larger people.

Energy expenditure is different than RMR because a person knows throughout the day how many calories have been burned so far, both at rest and when active. At the time when the user views energy expenditure information, two things are known. First, the caloric burn of that individual from midnight until that time of day, as recorded by armband sensor device. Second, that user's RMR from the current time until the end of the day. The sum of these numbers is a prediction of the minimum amount of calories that the user expends during the day.

This estimate may be improved by applying a multiplicative factor to RMR. A person's lifestyle contributes greatly to the amount of energy they expend. A sedentary person who does not exercise burns calories only slightly more than those consumed by their RMR. An athlete who is constantly active burns significantly more calories than RMR. These lifestyle effects on RMR may be estimated as multiplicative factors to RMR ranging from 1.1 for a sedentary person to 1.7 for an athlete. This multiplicative factor may also calculated from an average measurement of the person's wear time based on the time of day or the time of year, or it may be determined from information a user has entered in date or time management program, as described above. Using such a factor greatly improves the predictive nature of the estimated daily expenditure for an individual.

The final factor in predicting a weight-loss trend is a nutrition log. A nutrition log allows a person keeps track of the food they are eating. This records the amount of calories consumed so far during the day.

Knowing the amount of calories consumed and a prediction of the amount of calories a person can burn allows the armband sensor device to compute a person's energy balance. Energy balance is the difference between calories burned and calories consumed. If a person is expending more calories than they are consuming, they are on a weight-loss trend. A person who is consuming more calories than they are burning is on a weight-gain trend. An energy balance prediction is an estimate made at any time during the day of a person's actual daily energy balance for that day.

Suggestions are provided in the form of intermittent status reports, which take one of three general forms. First, a person may be in compliance to achieve the preset goal. This means that the energy balance prediction is within a tolerance range which approximates the daily goal. Second, a person may have already achieved the preset goal. If that user's energy balance indicates that more calories may be burned during the day than have been consumed, the user may be congratulated for surpassing the preset goal. Lastly, a user may have consumed more calories than what is projected to be burned. In this case, the system can calculate how many more calories that user may need to burn to meet the goal. Using the predicted energy expenditure associated with common activities, such as walking, the system can also make suggestions on methods for achieving the goal within a defined period. For example, a person who needs to burn 100 more calories might be advised to take a 30 minute walk in order to achieve a goal given that the system is aware that such activity can burn the necessary calories.

Many people settle into routines, especially during the work week. For example, a person may wake up at about the same time every day, go to work, then exercise after work before going home and relaxing. Their eating patterns may also be similar from day to day. Detecting such similarities in a person's behaviors can allow the armband sensor device to make more accurate predictions about a person's energy balance and therefore that person's weight-loss trends.

There are several ways the energy balance predications can be improved by analyzing an user's past data. First, the amount of rest verses activity in a person's lifestyle can be used to improve the RMR estimate for the remainder of the day. Second, the day can be broken down into time units to improve estimation. For example, a person who normally exercises in the morning and rests in the evening has a different daily profile than a person who exercises in the evening. The energy expenditure estimate can be adjusted based on time-of-day to better predict an individual's energy balance. A person's activity may also vary depending on a daily or weekly schedule, the time of the year, or degree of progress toward preset goals. The energy expenditure estimate can therefore be adjusted accordingly. Again, this information may be obtained from a time or date management program. Third, creating an average of a person's daily energy expenditure over a certain time can also be used to predict how many calories a person normally burns.

Likewise, detecting trends in a person's eating habits can be used to estimate how many calories a person is expected to consume. For example, a person who eats a large breakfast but small dinner has a different profile than a person who skips breakfast but eats a number of small meals during the day. These different eating habits can also be reflected in an user's energy balance to provide a more accurate daily estimate.

The concept of energy balance is not limited to single days. It may also be applied to multiple days, weeks, months or even years. For example, people often overeat on special occasions such as holidays, birthdays or anniversaries. Such unusual consumption eating spurts may be spurious or may contribute to long-term patterns. Actual energy balance over time can indicate weight-loss or weight-gain trends and help an individual adjust his goal to match actual exercise and eating habits.

Figure 16:
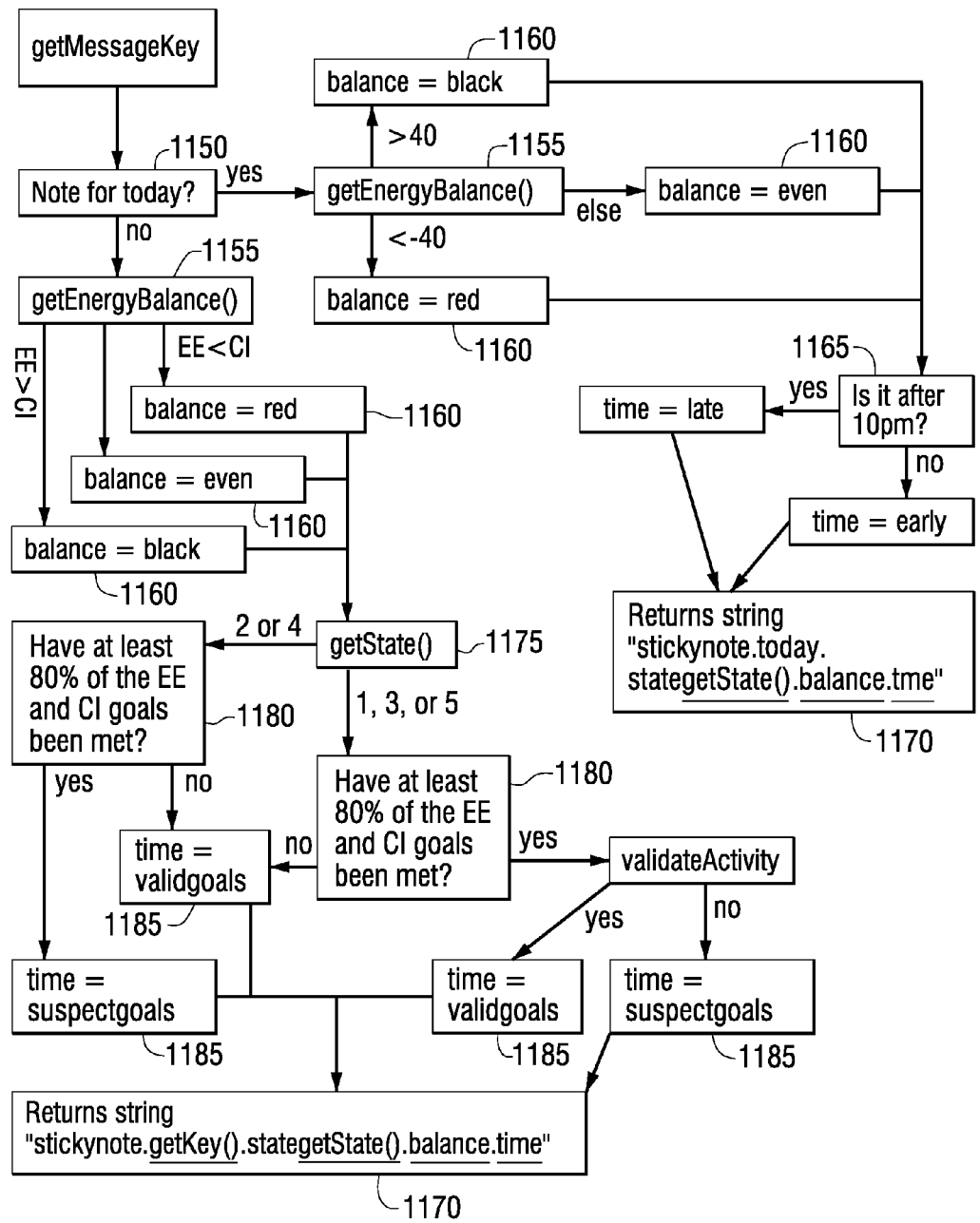
FIG. 16 is a logical diagram illustrating the generation of intermittent status reports according to an aspect of the present invention.

The logic for the calculation of the intermittent status reports 1140 is provided in the references to FIGS. 16-19. FIG. 16 illustrates the calculation of the intermittent status reports 1140 using information from both the energy expenditure and caloric intake values. If the intermittent status report status 1150 indicates that an intermittent status report 1140 has already been prepared for today, the intermittent status report program returns the energy balance value 1155 which is the difference between the energy expenditure and the daily caloric intake. An arbitrary threshold, for example 40 calories, is chosen as a goal tolerance to place the user into one of three categories. If the difference between the energy expenditure and the daily caloric intake is greater than +40 calories, a balance status indicator 1160 indicates that the user has significantly exceeded a daily energy balance goal for the day. If the difference between the values is less than −40 calories, a balance status indicator 1160 indicates that the user has failed to meet a daily energy balance goal. If the difference between the values is near or equal to 0, as defined by the tolerance between ±40 calories difference, a balance status indicator 1160 indicates that the user has met a daily energy balance goal. The program performs a time check 1165. Depending on whether the current time is before or after an arbitrary time limit, the program determines if it is early or late. Further, the program displays an energy balance goal intermittent status report 1170 indicating whether an individual has time to meet their energy balance goal within the time limit of the day or other period, based on the time of day, in addition to a suggestion for an energy expenditure activity to assist in accomplishing the goal, all based upon the prior intermittent status report 1040 for that day.

If the intermittent status report status 1150 determines that an intermitted status report 1040 has not been prepared for today, the program retrieves the energy balance value 1155 and determines if the energy expenditure is greater or less than the caloric intake value. Depending on the value of the difference between the energy expenditure value and the caloric intake value which is indicated by the balance status indicator 1160, the program performs a user state determination. The user state determination 1175 is the overall relationship between the user's goal and actual energy expenditure for the relevant time periods and the goal and actual daily caloric intake for that same period. After the program determines the user's state, the program determines the goal status 1180 of the user. If the status of the goals is within a certain percentage of completion, the program performs a time determination 1185 in regard to whether or not the user can still meet these goals, within the time frame, by performing a certain activity. The program displays a relevant energy balance goal intermittent status report 1170 to the user. The content of intermittent status report 1170 is determined by the outcome of these various determinations and is selected from an appropriate library of reference material.

Figure 17:
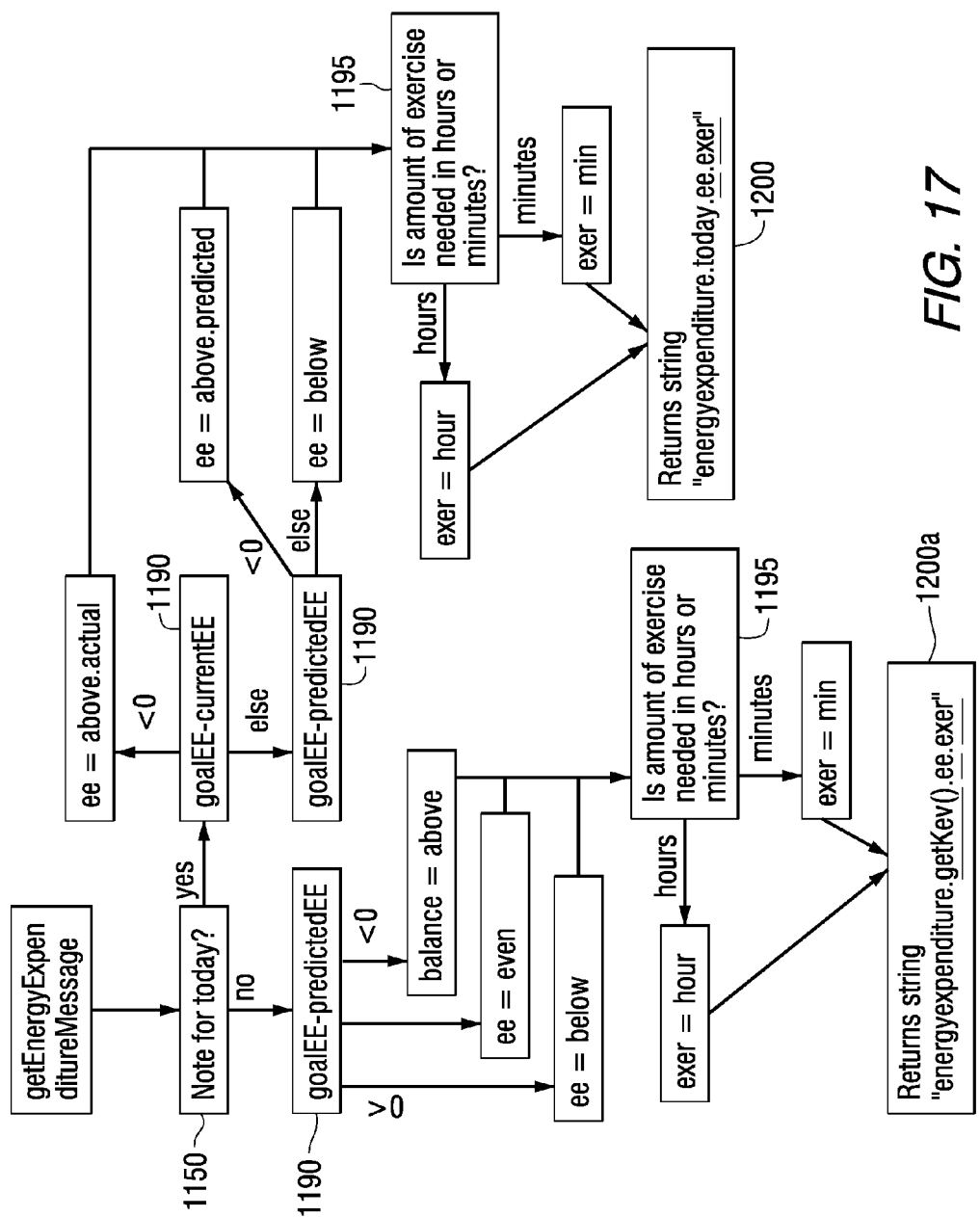
FIG. 17 is a logical diagram illustrating the generation of an intermittent status report based on energy expenditure values according to an aspect of the present invention.

FIG. 17 illustrates the generation of an intermittent status report based only on energy expenditure. If the intermittent status report status 1150 indicates that an intermittent status report 104 has been prepared for the day, the program calculates the energy expenditure goal progress 1190 which is the difference between the goal energy expenditure and the current energy expenditure. If the energy expenditure exceeds the goal energy expenditure, the program determines any required exercise amount 1195 that may be needed to enable the user to achieve energy expenditure goals for the day. Similarly, if the current or predicted energy expenditure value is less than the goal energy expenditure, the program determines any required exercise amount 1195 to enable to the user to meet the daily goal. An energy expenditure intermittent status report 1200 will be generated based on this information with suggested exercise activity.

If an intermittent status report 1040 has not already been prepared for the relevant time period, the intermittent status report status 1150 instructs the program to calculate the energy expenditure goal progress 1190 using the goal and predicted energy expenditure values. Based on this value, the program determines any required exercise amount 1195 to enable the user to achieve energy expenditure goals. An energy expenditure intermittent status report 1200a is generated based on this information with any suggested exercise activity.

Figure 18:
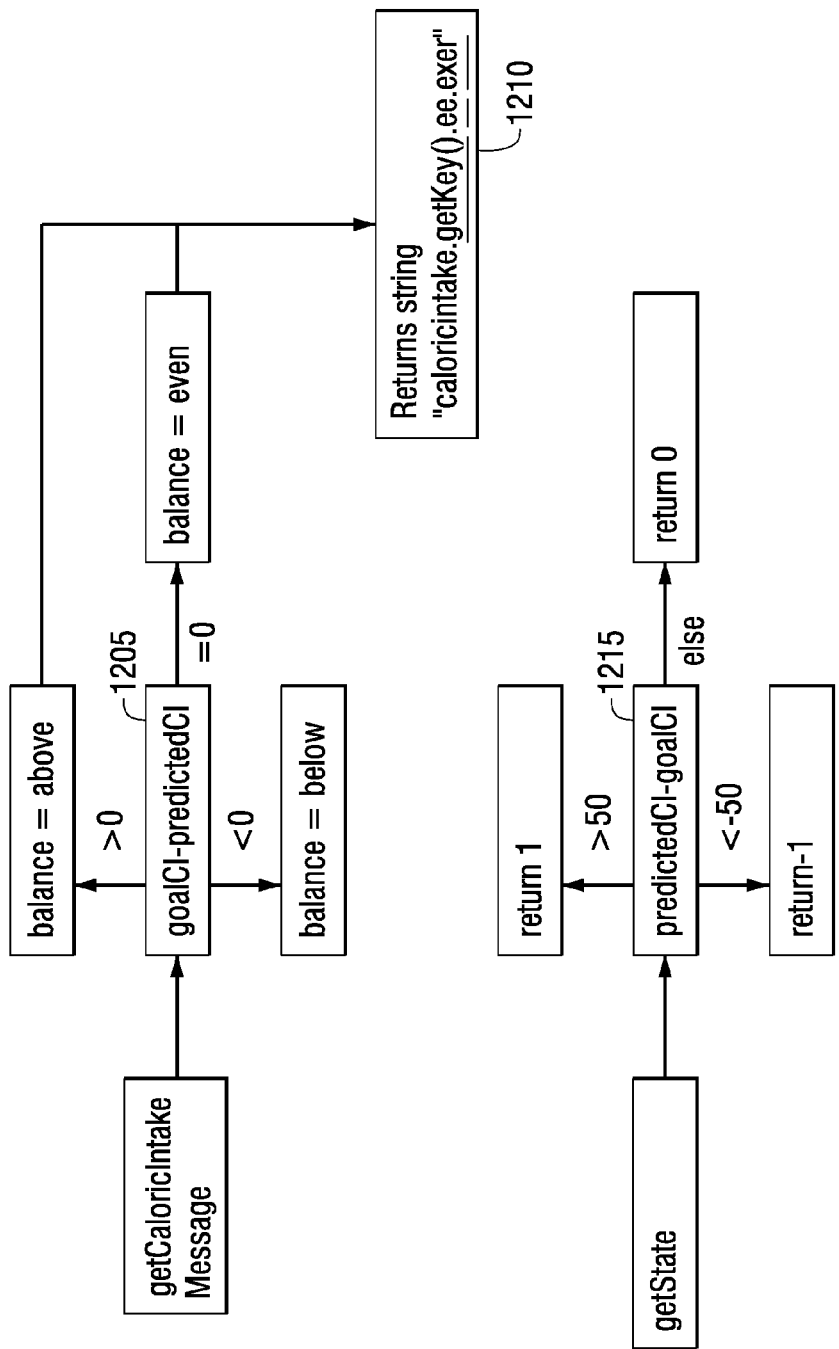
FIG. 18 is a logical diagram illustrating the generation of an intermittent status report based on caloric intake in addition to state status determination according to an aspect of the present invention.

FIG. 18 illustrates how the program generates an intermittent status report based solely on caloric intake. The caloric status 1205 is calculated, which is the difference between the goal caloric intake and predicted caloric intake. If the predicted caloric intake is greater than the goal caloric intake, the user has exceeded the caloric budget. If the predicted caloric intake is less than the goal caloric intake the user has consumed less calories than the caloric budget. If the value is near or equal to 0, the user has met their caloric budget. A caloric intake intermittent status report 1210 is generated based on this information.

Similarly, FIG. 18 illustrates how the program makes a user state status determination 1215 of the user's caloric intake. This calculation may be the same for the determination of the user's state of energy expenditure. The user state status is determined by subtracting the difference between the predicted caloric intake and the goal caloric intake. An arbitrary threshold, for example 50, is chosen as a goal tolerance to place the user into one of three categories. If the difference between the predicted caloric intake and the goal caloric intake is greater than +50 calories, the state status determination result is 1. If the difference between the predicted caloric intake and the goal caloric intake is less than −50 calories, the state status determination result is −1. If the goal amount is greater than the predicted amount, the program returns a negative 1. If the difference between the values is near or equal to 0, as defined by the tolerance between ±50 caloric difference, the state status determination result is 0.

Based on the user state status determination described above, FIG. 19 illustrates how the program ultimately makes the user state determination 1175. The program makes a user state status determination 1215 of the user's caloric intake determination based on the above calculation. After the program returns the value of 1, 0 or −1, the program makes a user state status determination 1215 of the user's energy expenditure. Based on the combination of the values, a user state determination 1 175 is calculated.

Figure 25:
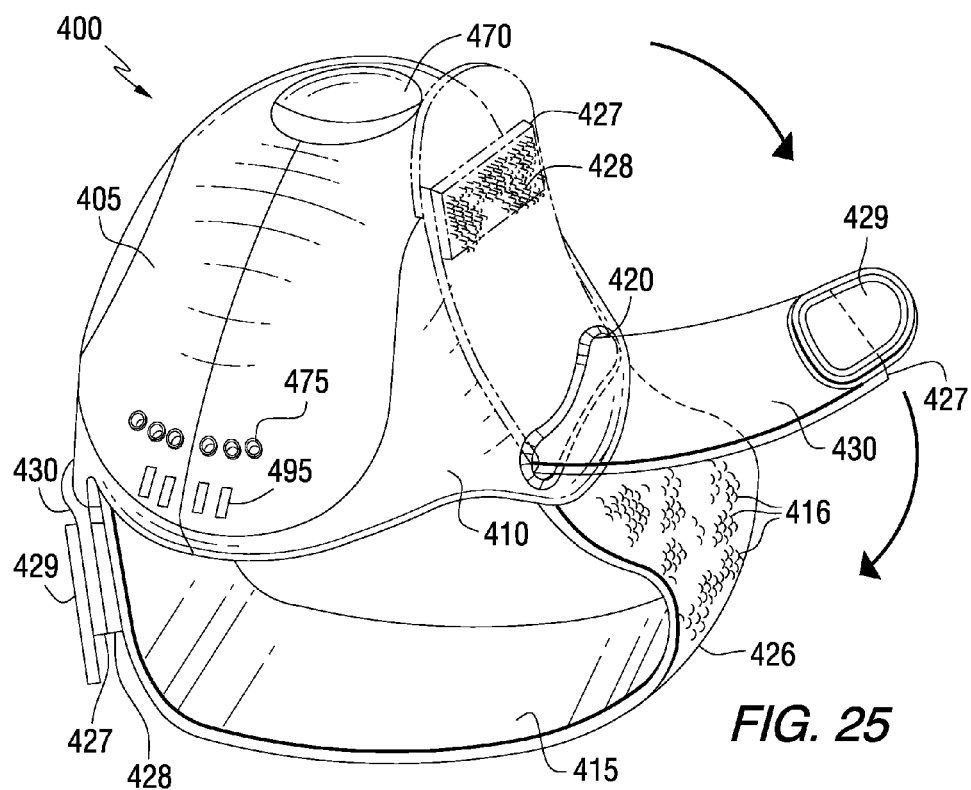
Figure 26:
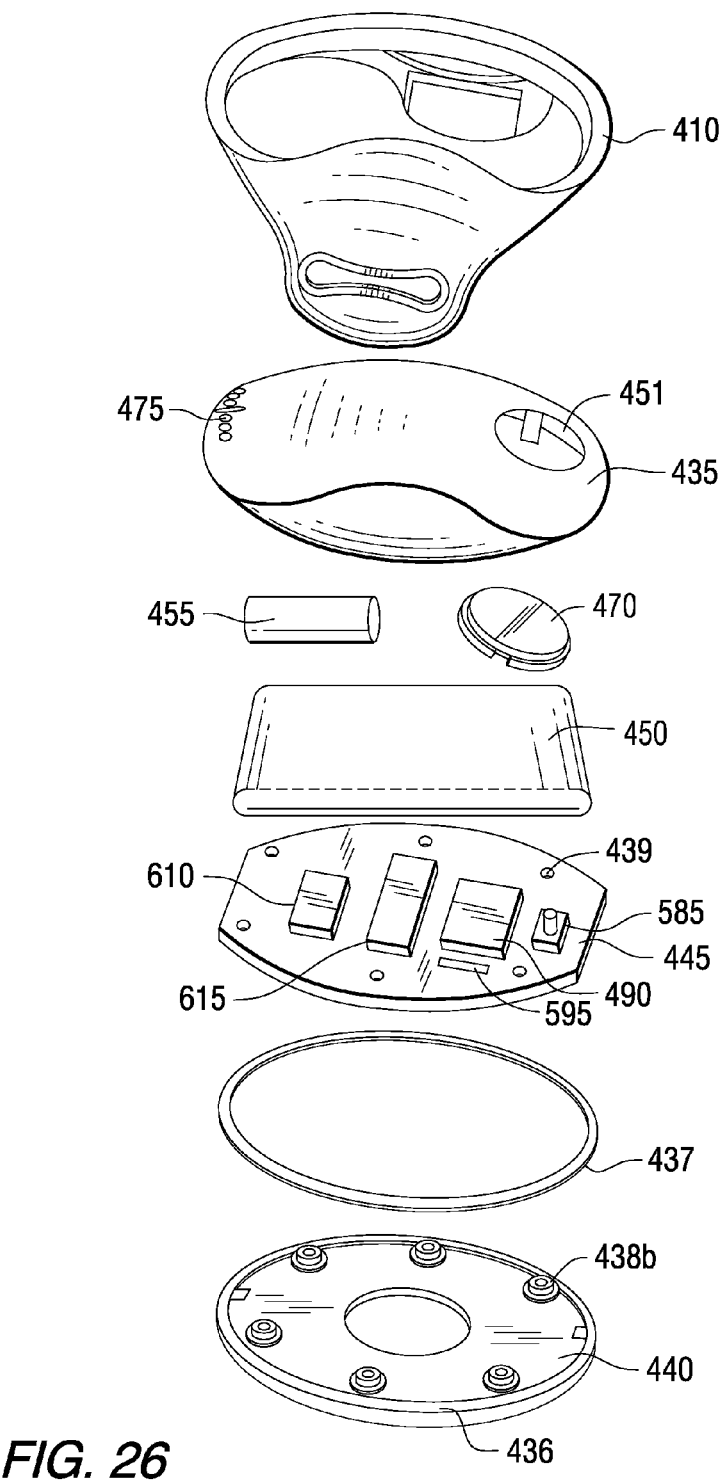
FIG. 26 is an exploded side perspective view of a specific embodiment of the sensor device shown in FIG. 1.

A specific embodiment of sensor device 10 is shown which is in the form of an armband adapted to be worn by an individual on his or her upper arm, between the shoulder and the elbow, as illustrated in FIGS. 20-25. Although a similar sensor device may be worn on other parts of the individual's body, these locations have the same function for single or multi-sensor measurements and for the automatic detection and/or identification of the user's activities or state. For the purpose of this disclosure, the specific embodiment of sensor device 10 shown in FIGS. 20-25 will, for convenience, be referred to as armband sensor device 400. Armband sensor device 400 includes computer housing 405, flexible wing body 410, and, as shown in FIG. 25, elastic strap 415. Computer housing 405 and flexible wing body 410 are preferably made of a flexible urethane material or an elastomeric material such as rubber or a rubber-silicone blend by a molding process. Flexible wing body 410 includes first and second wings 418 each having a thru-hole 420 located near the ends 425 thereof. First and second wings 418 are adapted to wrap around a portion of the wearer's upper arm.

Elastic strap 415 is used to removably affix armband sensor device 400 to the individual's upper arm. As seen in FIG. 25, bottom surface 426 of elastic strap 415 is provided with velcro loops 416 along a portion thereof. Each end 427 of elastic strap 415 is provided with velcro hook patch 428 on bottom surface 426 and pull tab 429 on top surface 430. A portion of each pull tab 429 extends beyond the edge of each end 427.

In order to wear armband sensor device 400, a user inserts each end 427 of elastic strap 415 into a respective thru-hole 420 of flexible wing body 410. The user then places his arm through the loop created by elastic strap 415, flexible wing body 410 and computer housing 405. By pulling each pull tab 429 and engaging velcro hook patches 428 with velcro loops 416 at a desired position along bottom surface 426 of elastic strap 415, the user can adjust elastic strap 415 to fit comfortably. Since velcro hook patches 428 can be engaged with velcro loops 416 at almost any position along bottom surface 426, armband sensor device 400 can be adjusted to fit arms of various sizes. Also, elastic strap 415 may be provided in various lengths to accommodate a wider range of arm sizes. As will be apparent to one of skill in the art, other means of fastening and adjusting the size of elastic strap may be used, including, but not limited to, snaps, buttons, or buckles. It is also possible to use two elastic straps that fasten by one of several conventional means including velcro, snaps, buttons, buckles or the like, or merely a single elastic strap affixed to wings 418.

Alternatively, instead of providing thru-holes 420 in wings 418, loops having the shape of the letter D, not shown, may be attached to ends 425 of wings 418 by one of several conventional means. For example, a pin, not shown, may be inserted through ends 425, wherein the pin engages each end of each loop. In this configuration, the D-shaped loops would serve as connecting points for elastic strap 415, effectively creating a thru-hole between each end 425 of each wing 418 and each loop.

As shown in FIG. 18, which is an exploded view of armband sensor device 400, computer housing 405 includes a top portion 435 and a bottom portion 440. Contained within computer housing 405 are printed circuit board or PCB 445, rechargeable battery 450, preferably a lithium ion battery, and vibrating motor 455 for providing tactile feedback to the wearer, such as those used in pagers, suitable examples of which are the Model 12342 and 12343 motors sold by MG Motors Ltd. of the United Kingdom.

Top portion 435 and bottom portion 440 of computer housing 405 sealingly mate along groove 436 into which 0-ring 437 is fit, and may be affixed to one another by screws, not shown, which pass through screw holes 438*a* and stiffeners 438*b* of bottom portion 440 and apertures 439 in PCB 445 and into threaded receiving stiffeners 451 of top portion 435. Alternately, top portion 435 and bottom portion 440 may be snap fit together or affixed to one another with an adhesive. Preferably, the assembled computer housing 405 is sufficiently water resistant to permit armband sensor device 400 to be worn while swimming without adversely affecting the performance thereof.

Figure 21:
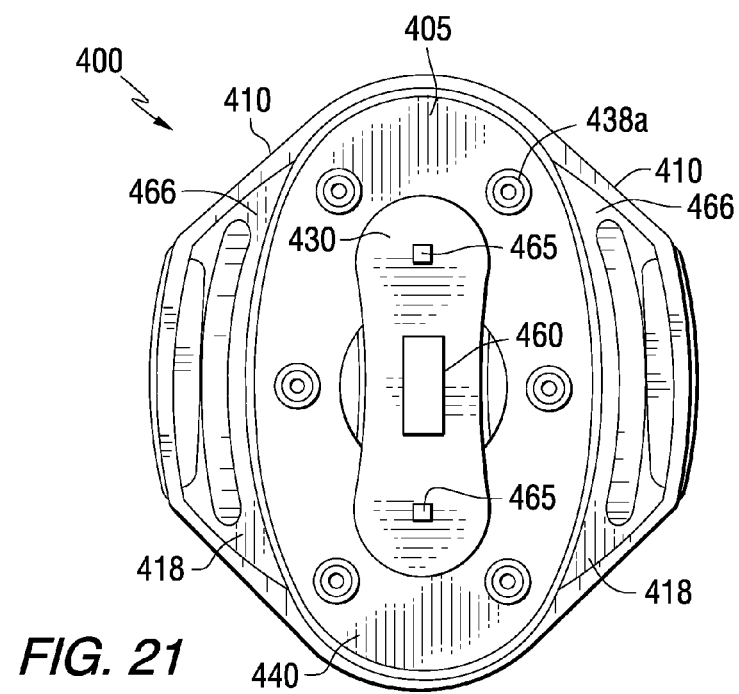
FIG. 21 is a back view of a specific embodiment of the sensor device shown in FIG. 1.
Figure 22:
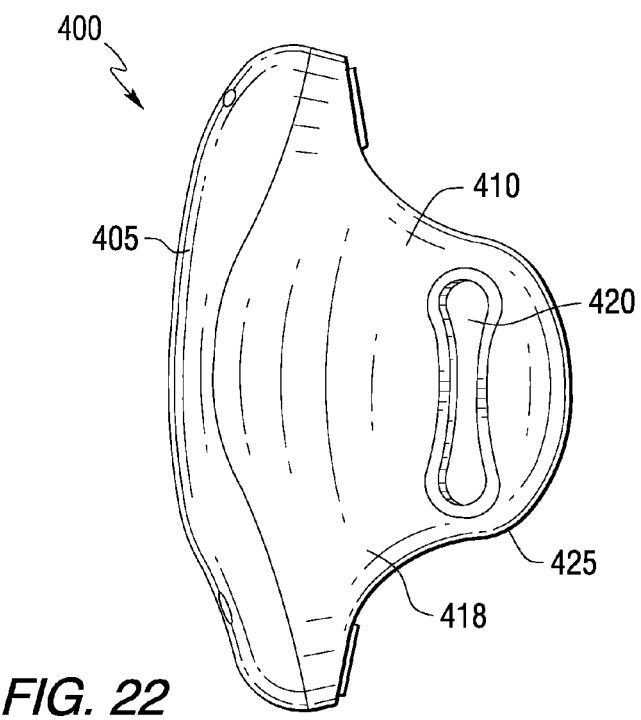
FIG. 22 is a side view of a specific embodiment of the sensor device shown in FIG. 1.
Figure 23:
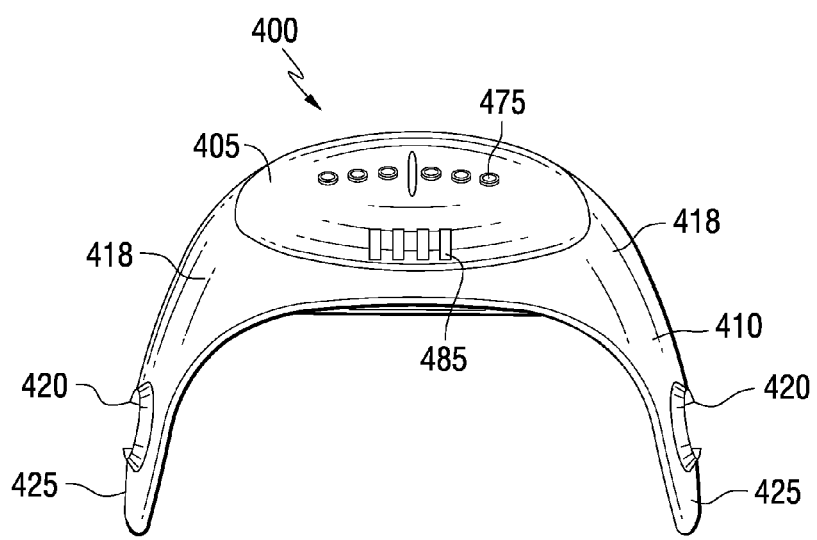
FIG. 23 is a bottom view of a specific embodiment of the sensor device shown in FIG. 1.
Figure 24:
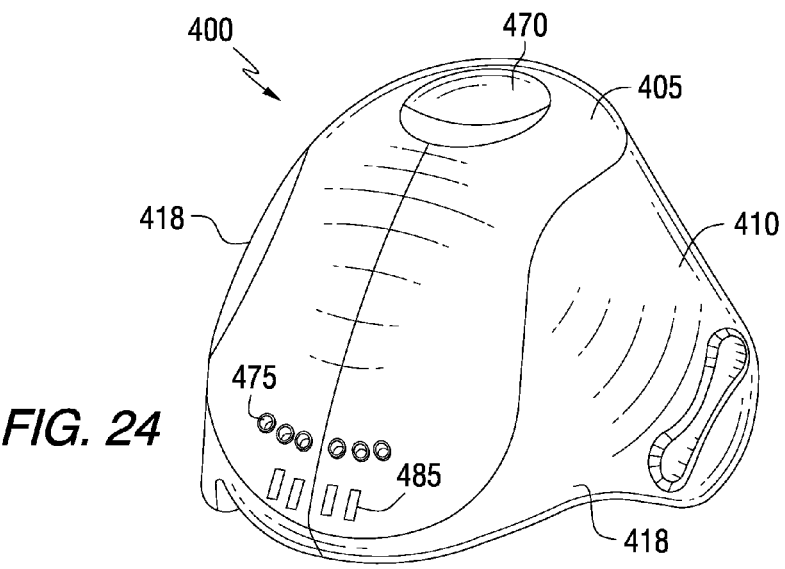
FIGS. 24 and 25 are front perspective views of a specific embodiment of the sensor device shown in FIG. 1.

As can be seen in FIG. 13, bottom portion 440 includes, on a bottom side thereof, a raised platform 430. Affixed to raised platform 430 is heat flow or flux sensor 460, a suitable example of which is the micro-foil heat flux sensor sold by RdF Corporation of Hudson, N.H. Heat flux sensor 460 functions as a self-generating thermopile transducer, and preferably includes a carrier made of a polyamide film. Bottom portion 440 may include on a top side thereof, that is on a side opposite the side to which heat flux sensor 460 is affixed, a heat sink, not shown, made of a suitable metallic material such as aluminum. Also affixed to raised platform 430 are GSR sensors 465, preferably comprising electrodes formed of a material such as conductive carbonized rubber, gold or stainless steel. Although two GSR sensors 465 are shown in FIG. 21, it will be appreciated by one of skill in the art that the number of GSR sensors 465 and the placement thereof on raised platform 430 can vary as long as the individual GSR sensors 465, i.e., the electrodes, are electrically isolated from one another. By being affixed to raised platform 430, heat flux sensor 460 and GSR sensors 465 are adapted to be in contact with the wearer's skin when armband sensor device 400 is worn. Bottom portion 440 of computer housing 405 may also be provided with a removable and replaceable soft foam fabric pad, not shown, on a portion of the surface thereof that does not include raised platform 430 and screw holes 438*a*. The soft foam fabric is intended to contact the wearer's skin and make armband sensor device 400 more comfortable to wear.

Electrical coupling between heat flux sensor 460, GSR sensors 465, and PCB 445 may be accomplished in one of various known methods. For example, suitable wiring, not shown, may be molded into bottom portion 440 of computer housing 405 and then electrically connected, such as by soldering, to appropriate input locations on PCB 445 and to heat flux sensor 460 and GSR sensors 465. Alternatively, rather than molding wiring into bottom portion 440, thru-holes may be provided in bottom portion 440 through which appropriate wiring may pass. The thru-holes would preferably be provided with a water tight seal to maintain the integrity of computer housing 405.

Rather than being affixed to raised platform 430 as shown in FIG. 21, one or both of heat flux sensor 460 and GSR sensors 465 may be affixed to the inner portion 466 of flexible wing body 410 on either or both of wings 418 so as to be in contact with the wearer's skin when armband sensor device 400 is worn. In such a configuration, electrical coupling between heat flux sensor 460 and GSR sensors 465, whichever the case may be, and the PCB 445 may be accomplished through suitable wiring, not shown, molded into flexible wing body 410 that passes through one or more thru-holes in computer housing 405 and that is electrically connected, such as by soldering, to appropriate input locations on PCB 445. Again, the thru-holes would preferably be provided with a water tight seal to maintain the integrity of computer housing 405. Alternatively, rather than providing thru-holes in computer housing 405 through which the wiring passes, the wiring may be captured in computer housing 405 during an overmolding process, described below, and ultimately soldered to appropriate input locations on PCB 445.

As shown in FIGS. 12, 16, 17 and 18, computer housing 405 includes a button 470 that is coupled to and adapted to activate a momentary switch 585 on PCB 445. Button 470 may be used to activate armband sensor device 400 for use, to mark the time an event occurred or to request system status information such as battery level and memory capacity. When button 470 is depressed, momentary switch 585 closes a circuit and a signal is sent to processing unit 490 on PCB 445. Depending on the time interval for which button 470 is depressed, the generated signal triggers one of the events just described. Computer housing 405 also includes LEDs 475, which may be used to indicate battery level or memory capacity or to provide visual feedback to the wearer. Rather than LEDs 475, computer housing 405 may also include a liquid crystal display or LCD to provide battery level, memory capacity or visual feedback information to the wearer. Battery level, memory capacity or feedback information may also be given to the user tactily or audibly.

Armband sensor device 400 may be adapted to be activated for use, that is collecting data, when either of GSR sensors 465 or heat flux sensor 460 senses a particular condition that indicates that armband sensor device 400 has been placed in contact with the user's skin. Also, armband sensor device 400 may be adapted to be activated for use when one or more of heat flux sensor 460, GSR sensors 465, accelerometer 495 or 550, or any other device in communication with armband sensor device 400, alone or in combination, sense a particular condition or conditions that indicate that the armband sensor device 400 has been placed in contact with the user's skin for use. At other times, armband sensor device 400 would be deactivated, thus preserving battery power.

Figure 27:
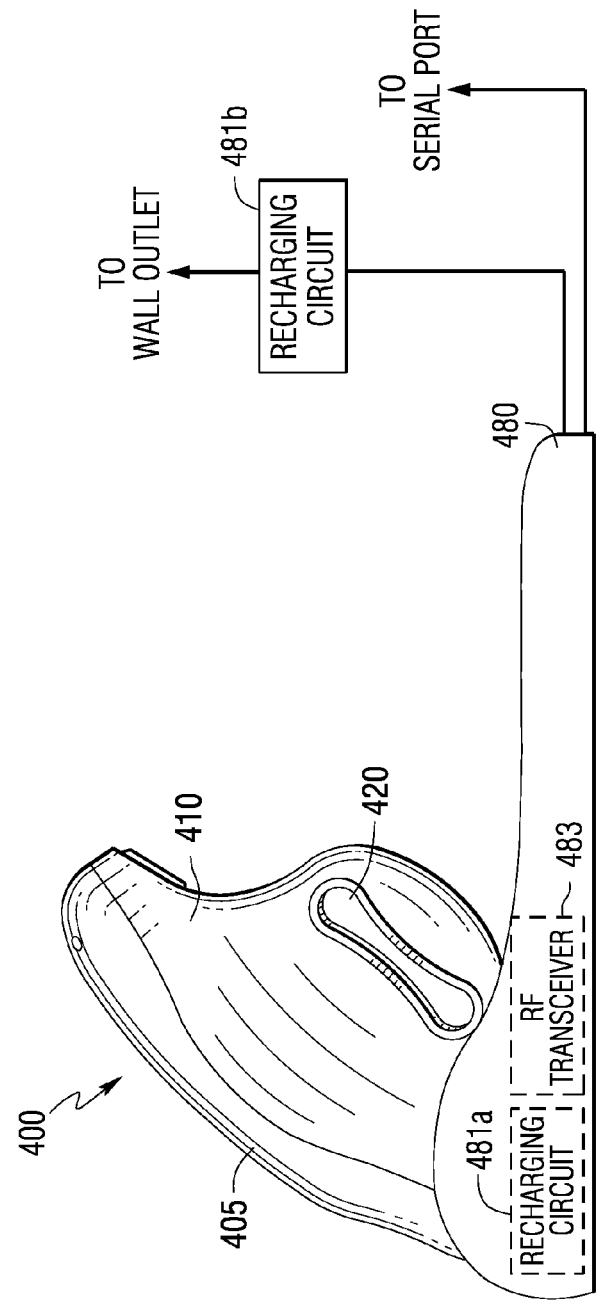
FIG. 27 is a side view of the sensor device shown in FIGS. 20 through 26 inserted into a battery recharger unit.

Computer housing 405 is adapted to be coupled to a battery recharger unit 480 shown in FIG. 27 for the purpose of recharging rechargeable battery 450. Computer housing 405 includes recharger contacts 485, shown in FIGS. 12, 15, 16 and 17, that are coupled to rechargeable battery 450. Recharger contracts 485 may be made of a material such as brass, gold or stainless steel, and are adapted to mate with and be electrically coupled to electrical contacts, not shown, provided in battery recharger unit 480 when armband sensor device 400 is placed therein. The electrical contacts provided in battery recharger unit 480 may be coupled to recharging circuit 481 a provided inside battery recharger unit 480. In this configuration, recharging circuit 481 would be coupled to a wall outlet, such as by way of wiring including a suitable plug that is attached or is attachable to battery recharger unit 480. Alternatively, electrical contacts 480 may be coupled to wiring that is attached to or is attachable to battery recharger unit 480 that in turn is coupled to recharging circuit 481b external to battery recharger unit 480. The wiring in this configuration would also include a plug, not shown, adapted to be plugged into a conventional wall outlet.

Figure 19:
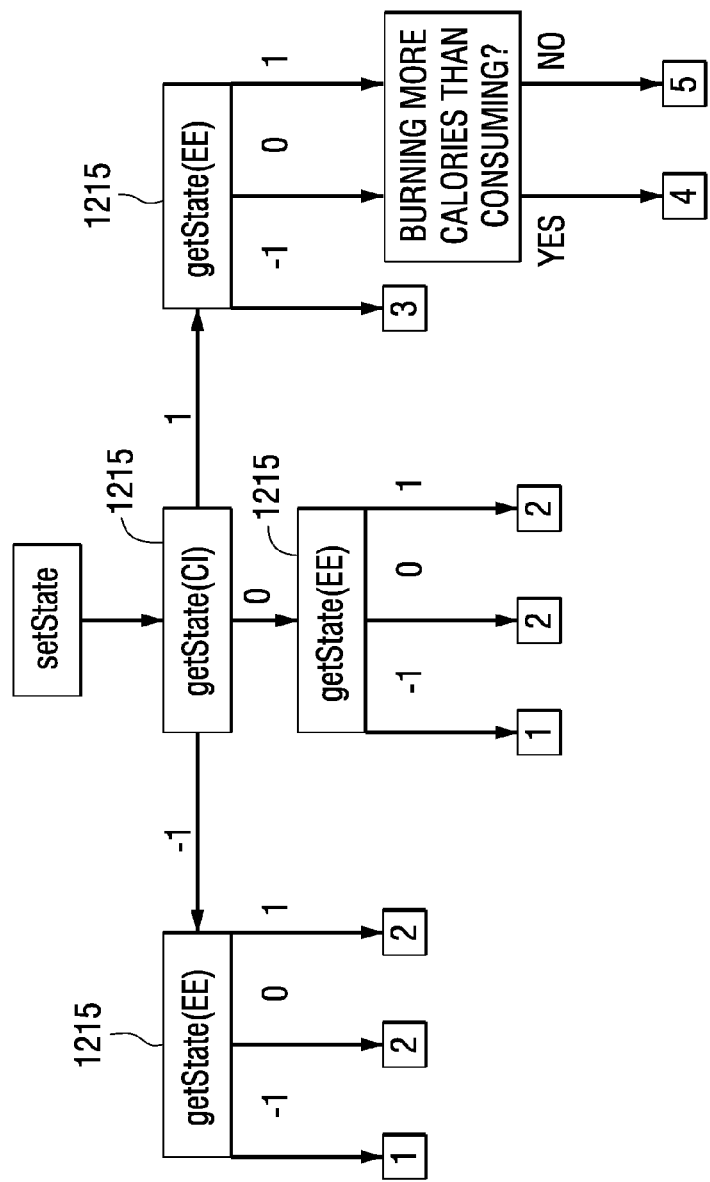
FIG. 19 is a logical diagram illustrating the calculation of state determination according to an aspect of the present invention.
Figure 20:
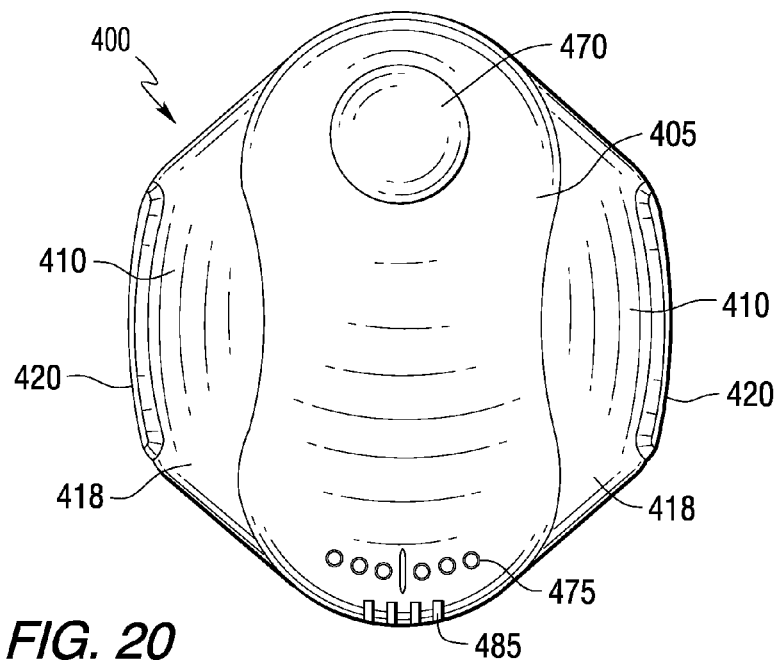
FIG. 20 is a front view of a specific embodiment of the sensor device shown in FIG. 1.
Figure 28:
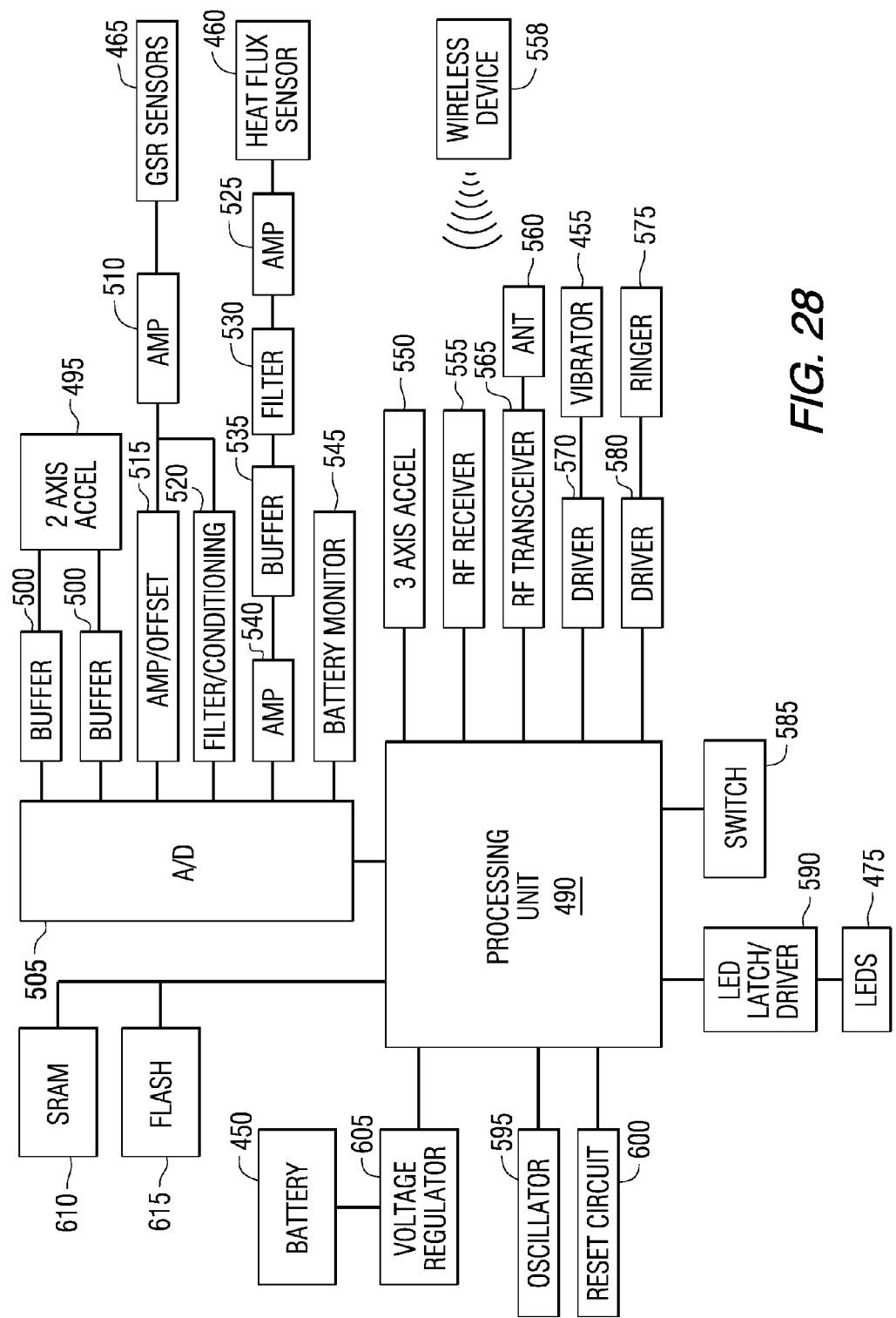
FIG. 28 is a block diagram illustrating all of the components either mounted on or coupled to the printed circuit board forming a part of the sensor device shown in FIGS. 20 through 26.

Also provided inside battery recharger unit 480 is RF transceiver 483 adapted to receive signals from and transmit signals to RF transceiver 565 provided in computer housing 405 and shown in FIG. 28. RF transceiver 483 is adapted to be coupled, for example by a suitable cable, to a serial port, such as an RS 232 port or a USB port, of a device such as personal computer 35 shown in FIG. 1. Thus, data may be uploaded from and downloaded to armband sensor device 400 using RF transceiver 483 and RF transceiver 565. It will be appreciated that although RF transceivers 483 and 565 are shown in FIGS. 19 and 20, other forms of wireless transceivers may be used, such as infrared transceivers. Alternatively, computer housing 405 may be provided with additional electrical contacts, not shown, that would be adapted to mate with and be electrically coupled to additional electrical contacts, not shown, provided in battery recharger unit 480 when armband sensor device 400 is placed therein. The additional electrical contacts in the computer housing 405 would be coupled to the processing unit 490 and the additional electrical contacts provided in battery recharger unit 480 would be coupled to a suitable cable that in turn would be coupled to a serial port, such as an RS R32 port or a USB port, of a device such as personal computer 35. This configuration thus provides an alternate method for uploading of data from and downloading of data to armband sensor device 400 using a physical connection.

FIG. 28 is a schematic diagram that shows the system architecture of armband sensor device 400, and in particular each of the components that is either on or coupled to PCB 445.

As shown in FIG. 25, PCB 445 includes processing unit 490, which may be a microprocessor, a microcontroller, or any other processing device that can be adapted to perform the functionality described herein. Processing unit 490 is adapted to provide all of the functionality described in connection with microprocessor 20 shown in FIG. 2. A suitable example of processing unit 490 is the Dragonball EZ sold by Motorola, Inc. of Schaumburg, Ill. PCB 445 also has thereon a two-axis accelerometer 495, a suitable example of which is the Model ADXL210 accelerometer sold by Analog Devices, Inc. of Norwood; Mass. Two-axis accelerometer 495 is preferably mounted on PCB 445 at an angle such that its sensing axes are offset at an angle substantially equal to 45 degrees from the longitudinal axis of PCB 445 and thus the longitudinal axis of the wearer's arm when armband sensor device 400 is worn. The longitudinal axis of the wearer's arm refers to the axis defined by a straight line drawn from the wearer's shoulder to the wearer's elbow. The output signals of two-axis accelerometer 495 are passed through buffers 500 and input into analog to digital converter 505 that in turn is coupled to processing unit 490. GSR sensors 465 are coupled to amplifier 510 on PCB 445. Amplifier 510 provides amplification and low pass filtering functionality, a suitable example of which is the Model AD8544 amplifier sold by Analog Devices, Inc. of Norwood, Mass. The amplified and filtered signal output by amplifier 510 is input into amp/offset 515 to provide further gain and to remove any bias voltage and into filter/conditioning circuit 520, which in turn are each coupled to analog to digital converter 505. Heat flux sensor 460 is coupled to differential input amplifier 525, such as the Model INA amplifier sold by Burr-Brown Corporation of Tucson, Ariz., and the resulting amplified signal is passed through filter circuit 530, buffer 535 and amplifier 540 before being input to analog to digital converter 505. Amplifier 540 is configured to provide further gain and low pass filtering, a suitable example of which is the Model AD8544 amplifier sold by Analog Devices, Inc. of Norwood, Mass. PCB 445 also includes thereon a battery monitor 545 that monitors the remaining power level of rechargeable battery 450. Battery monitor 545 preferably comprises a voltage divider with a low pass filter to provide average battery voltage. When a user depresses button 470 in the manner adapted for requesting battery level, processing unit 490 checks the output of battery monitor 545 and provides an indication thereof to the user, preferably through LEDs 475, but also possibly through vibrating motor 455 or ringer 575. An LCD may also be used.

PCB 445 may include three-axis accelerometer 550 instead of or in addition to two-axis accelerometer 495. The three-axis accelerometer outputs a signal to processing unit 490. A suitable example of three-axis accelerometer is the μPAM product sold by I.M. Systems, Inc. of Scottsdale, Ariz. Three-axis accelerometer 550 is preferably tilted in the manner described with respect to two-axis accelerometer 495.

PCB 445 also includes RF receiver 555 that is coupled to processing unit 490. RF receiver 555 may be used to receive signals that are output by another device capable of wireless transmission, shown in FIG. 28 as wireless device 558, worn by or located near the individual wearing armband sensor device 400. Located near as used herein means within the transmission range of wireless device 558. For example, wireless device 558 may be a chest mounted heart rate monitor such as the Tempo product sold by Polar Electro of Oulu, Finland. Using such a heart rate monitor, data indicative of the wearer's heart rate can be collected by armband sensor device 400. Antenna 560 and RF transceiver 565 are coupled to processing unit 490 and are provided for purposes of uploading data to central monitoring unit 30 and receiving data downloaded from central monitoring unit 30. RF transceiver 565 and RF receiver 555 may, for example, employ Bluetooth technology as the wireless transmission protocol. Also, other forms of wireless transmission may be used, such as infrared transmission.

Vibrating motor 455 is coupled to processing unit 490 through vibrator driver 570 and provides tactile feedback to the wearer. Similarly, ringer 575, a suitable example of which is the Model SMT916A ringer sold by Projects Unlimited, Inc. of Dayton, Ohio, is coupled to processing unit 490 through ringer driver 580, a suitable example of which is the Model MMBTA14 CTI darlington transistor driver sold by Motorola, Inc. of Schaumburg, Ill., and provides audible feedback to the wearer. Feedback may include, for example, celebratory, cautionary and other threshold or event driven messages, such as when a wearer reaches a level of calories burned during a workout.

Also provided on PCB 445 and coupled to processing unit 490 is momentary switch 58.5. Momentary switch 585 is also coupled to button 470 for activating momentary switch 585. LEDs 475, used to provide various types of feedback information to the wearer, are coupled to processing unit 490 through LED latch/driver 590.

Oscillator 595 is provided on PCB 445 and supplies the system clock to processing unit 490. Reset circuit 600, accessible and triggerable through a pin-hole in the side of computer housing 405, is coupled to processing unit 490 and enables processing unit 490 to be reset to a standard initial setting.

Rechargeable battery 450, which is the main power source for the armband sensor device 400, is coupled to processing unit 490 through voltage regulator 605. Finally, memory functionality is provided for armband sensor device 400 by SRAM 610, which stores data relating to the wearer of arm band sensor device 400, and flash memory 615, which stores program and configuration data, provided on PCB 445. SRAM 610 and flash memory 615 are coupled to processing unit 490 and each preferably have at least 512K of memory.

In manufacturing and assembling armband sensor device 400, top portion 435 of computer housing 405 is preferably formed first, such as by a conventional molding process, and flexible wing body 410 is then overmolded on top of top portion 435. That is, top portion 435 is placed into an appropriately shaped mold, i.e., one that, when top portion 435 is placed therein, has a remaining cavity shaped according to the desired shape of flexible wing body 410, and flexible wing body 410 is molded on top of top portion 435. As a result, flexible wing body 410 and top portion 435 will merge or bond together, forming a single unit. Alternatively, top portion 435 of computer housing 405 and flexible wing body 410 may be formed together, such as by molding in a single mold, to form a single unit. The single unit however formed may then be turned over such that the underside of top portion 435 is facing upwards, and the contents of computer housing 405 can be placed into top portion 435, and top portion 435 and bottom portion 440 can be affixed to one another. As still another alternative, flexible wing body 410 may be separately formed, such as by a conventional molding process, and computer housing 405, and in particular top portion 435 of computer housing 405, may be affixed to flexible wing body 410 by one of several known methods, such as by an adhesive, by snap-fitting, or by screwing the two pieces together. Then, the remainder of computer housing 405 would be assembled as described above. It will be appreciated that rather than assembling the remainder of computer housing 405 after top portion 435 has been affixed to flexible wing body 410, the computer housing 405 could be assembled first and then affixed to flexible wing body 410.

In a variety of the embodiments described above, it is specifically contemplated that the activity or nutritional data be input or detected by the system for derivation of the necessary data. As identified in several embodiments, the automatic detection of certain activities and/or nutritional intake may be substituted for such manual input. One aspect of the present invention relates to a sophisticated algorithm development process for creating a wide range of algorithms for generating information relating to a variety of variables from the data received from the plurality of physiological and/or contextual sensors on sensor device 400. Such variables may include, without limitation, energy expenditure, including resting, active and total values, daily caloric intake, sleep states, including in bed, sleep onset, sleep interruptions, wake, and out of bed, and activity states, including exercising, sitting, traveling in a motor vehicle, and lying down, and the algorithms for generating values for such variables may be based on data from, for example, the 2-axis accelerometer, the heat flux sensor, the GSR sensor, the skin temperature sensor, the near-body ambient temperature sensor, and the heart rate sensor in the embodiment described above.

Note that there are several types of algorithms that can be computed. For example, and without limitation, these include algorithms for predicting user characteristics, continual measurements, durative contexts, instantaneous events, and cumulative conditions. User characteristics include permanent and semi-permanent parameters of the wearer, including aspects such as weight, height, and wearer identity. An example of a continual measurement is energy expenditure, which constantly measures, for example on a minute by minute basis, the number of calories of energy expended by the wearer. Durative contexts are behaviors that last some period of time, such as sleeping, driving a car, or jogging. Instantaneous events are those that occur at a fixed or over a very short time period, such as a heart attack or falling down. Cumulative conditions are those where the person's condition can be deduced from their behavior over some previous period of time. For example, if a person hasn't slept in 36 hours and hasn't eaten in 10 hours, it is likely that they are fatigued. Table 8 below shows numerous examples of specific personal characteristics, continual measurements, durative measurements, instantaneous events, and cumulative conditions.

TABLE 8

| | |
|---|---|
| personal characteristics | age, sex, weight, gender, athletic ability, conditioning, disease, height, susceptibility to disease, activity level, individual detection, handedness, metabolic rate, body composition |
| continual measurements | mood, beat-to-beat variability of heart beats, respiration, energy expenditure, blood glucose levels, level of ketosis, heart rate, stress levels, fatigue levels, alertness levels, blood pressure, readiness, strength, endurance, amenability to |

TABLE 8-continued

| | |
|---|---|
| durative measurements | interaction, steps per time period, stillness level, body position and orientation, cleanliness, mood or affect, approachability, caloric intake, TEF, XEF, 'in the zone'-ness, active energy expenditure, carbohydrate intake, fat intake, protein intake, hydration levels, truthfulness, sleep quality, sleep state, consciousness level, effects of medication, dosage prediction, water intake, alcohol intake, dizziness, pain, comfort, remaining processing power for new stimuli, proper use of the armband, interest in a topic, relative exertion, location, blood-alcohol level exercise, sleep, lying down, sitting, standing, ambulation, running, walking, biking, stationary biking, road biking, lifting weights, aerobic exercise, anaerobic exercise, strength-building exercise, mind-centering activity, periods of intense emotion, relaxing, watching TV, sedentary, REM detector, eating, in-the-zone, interruptible, general activity detection, sleep stage, heat stress, heat stroke, amenable to teaching/learning, bipolar decompensation, abnormal events (in heart signal, in activity level, measured by the user, etc), startle level, highway driving or riding in a car, airplane travel, helicopter travel, boredom events, sport detection (football, baseball, soccer, etc), studying, reading, intoxication, effect of a drug |
| instantaneous events | falling, heart attack, seizure, sleep arousal events, PVCs, blood sugar abnormality, acute stress or disorientation, emergency, heart arrhythmia, shock, vomiting, rapid blood loss, taking medication, swallowing |
| cumulative conditions | Alzheimer's, weakness or increased likelihood of falling, drowsiness, fatigue, existence of ketosis, ovulation, pregnancy, disease, illness, fever, edema, anemia, having the flu, hypertension, mental disorders, acute dehydration, hypothermia, being-in-the-zone |

It will be appreciated that the present invention may be utilized in a method for doing automatic journaling of a wearer's physiological and contextual states. The system can automatically produce a journal of what activities the user was engaged in, what events occurred, how the user's physiological state changed over time, and when the user experienced or was likely to experience certain conditions. For example, the system can produce a record of when the user exercised, drove a car, slept, was in danger of heat stress, or ate, in addition to recording the user's hydration level, energy expenditure level, sleep levels, and alertness levels throughout a day. These detected conditions can be utilized to time- or event-stamp the data record, to modify certain parameters of the analysis or presentation of the data, as well as trigger certain delayed or real time feedback events.

According to the algorithm development process, linear or non-linear mathematical models or algorithms are constructed that map the data from the plurality of sensors to a desired variable. The process consists of several steps. First, data is collected by subjects wearing sensor device 400 who are put into situations as close to real world situations as possible, with respect to the parameters being measured, such that the subjects are not endangered and so that the variable that the proposed algorithm is to predict can, at the same time, be reliably measured using, for example, highly accurate medical grade lab equipment. This first step provides the following two sets of data that are then used as inputs to the algorithm development process: (i) the raw data from sensor device 400, and (ii) the data consisting of the verifiably accurate data measurements and extrapolated or derived data made with or calculated from the more accurate lab equipment. This verifiable data becomes a standard against which other analytical or measured data is compared. For cases in which the variable that the proposed algorithm is to predict relates to context detection, such as traveling in a motor vehicle, the verifiable standard data is provided by the subjects themselves, such as through information input manually into sensor device 400, a PC, or otherwise manually recorded. The collected data, i.e., both the raw data and the corresponding verifiable standard data, is then organized into a database and is split into training and test sets.

Next, using the data in the training set, a mathematical model is built that relates the raw data to the corresponding verifiable standard data. Specifically, a variety of machine learning techniques are used to generate two types of algorithms: 1) algorithms known as features, which are derived continuous parameters that vary in a manner that allows the prediction of the lab-measured parameter for some subset of the data points. The features are typically not conditionally independent of the lab-measured parameter e.g. VO2 level information from a metabolic cart, douglas bag, or doubly labeled water, and 2) algorithms known as context detectors that predict various contexts, e.g., running, exercising, lying down, sleeping or driving, useful for the overall algorithm. A number of well known machine learning techniques may be used in this step, including artificial neural nets, decision trees, memory-based methods, boosting, attribute selection through cross-validation, and stochastic search methods such as simulated annealing and evolutionary computation.

After a suitable set of features and context detectors are found, several well known machine learning methods are used to combine the features and context detectors into an overall model. Techniques used in this phase include, but are not limited to, multilinear regression, locally weighted regression, decision trees, artificial neural networks, stochastic search methods, support vector machines, and model trees. These models are evaluated using cross-validation to avoid over-fitting.

At this stage, the models make predictions on, for example, a minute by minute basis. Inter-minute effects are next taken into account by creating an overall model that integrates the minute by minute predictions. A well known or custom windowing and threshold optimization tool may be used in this step to take advantage of the temporal continuity of the data. Finally, the model's performance can be evaluated on the test set, which has not yet been used in the creation of the algorithm. Performance of the model on the test set is thus a good estimate of the algorithm's expected performance on other unseen data. Finally, the algorithm may undergo live testing on new data for further validation.

Further examples of the types of non-linear functions and/or machine learning method that may be used in the present invention include the following: conditionals, case statements, logical processing, probabilistic or logical inference, neural network processing, kernel based methods, memory-based lookup including kNN and SOMs, decision lists, decision-tree prediction, support vector machine prediction, clustering, boosted methods, cascade-correlation, Boltzmann classifiers, regression trees, case-based reasoning, Gaussians, Bayes nets, dynamic Bayesian networks, HMMs, Kalman filters, Gaussian processes and algorithmic predictors, e.g. learned by evolutionary computation or other program synthesis tools.

Although one can view an algorithm as taking raw sensor values or signals as input, performing computation, and then producing a desired output, it is useful in one preferred embodiment to view the algorithm as a series of derivations that are applied to the raw sensor values. Each derivation produces a signal referred to as a derived channel. The raw sensor values or signals are also referred to as channels, specifically raw channels rather than derived channels. These derivations, also referred to as functions, can be simple or complex but are applied in a predetermined order on the raw values and, possibly, on already existing derived channels. The first derivation must, of course, only take as input raw sensor signals and other available baseline information such as manually entered data and demographic information about the subject, but subsequent derivations can take as input previously derived channels. Note that one can easily determine, from the order of application of derivations, the particular channels utilized to derive a given derived channel. Also note that inputs that a user provides on an Input/Output, or I/O, device or in some fashion can also be included as raw signals which can be used by the algorithms. For example, the category chosen to describe a meal can be used by a derivation that computes the caloric estimate for the meal. In one embodiment, the raw signals are first summarized into channels that are sufficient for later derivations and can be efficiently stored. These channels include derivations such as summation, summation of differences, and averages. Note that although summarizing the high-rate data into compressed channels is useful both for compression and for storing useful features, it may be useful to store some or all segments of high rate data as well, depending on the exact details of the application. In one embodiment, these summary channels are then calibrated to take minor measurable differences in manufacturing into account and to result in values in the appropriate scale and in the correct units. For example, if, during the manufacturing process, a particular temperature sensor was determined to have a slight offset, this offset can be applied, resulting in a derived channel expressing temperature in degrees Celsius.

For purposes of this description, a derivation or function is linear if it is expressed as a weighted combination of its inputs together with some offset. For example, if G and H are two raw or derived channels, then all derivations of the form $A*G+B*H+C$, where A, B, and C are constants, is a linear derivation. A derivation is non-linear with respect to its inputs if it can not be expressed as a weighted sum of the inputs with a constant offset. An example of a nonlinear derivation is as follows: if $G>7$ then return $H*9$, else return $H*3.5\pm912$. A channel is linearly derived if all derivations involved in computing it are linear, and a channel is nonlinearly derived if any of the derivations used in creating it are nonlinear. A channel nonlinearly mediates a derivation if changes in the value of the channel change the computation performed in the derivation, keeping all other inputs to the derivation constant.

Figure 29:
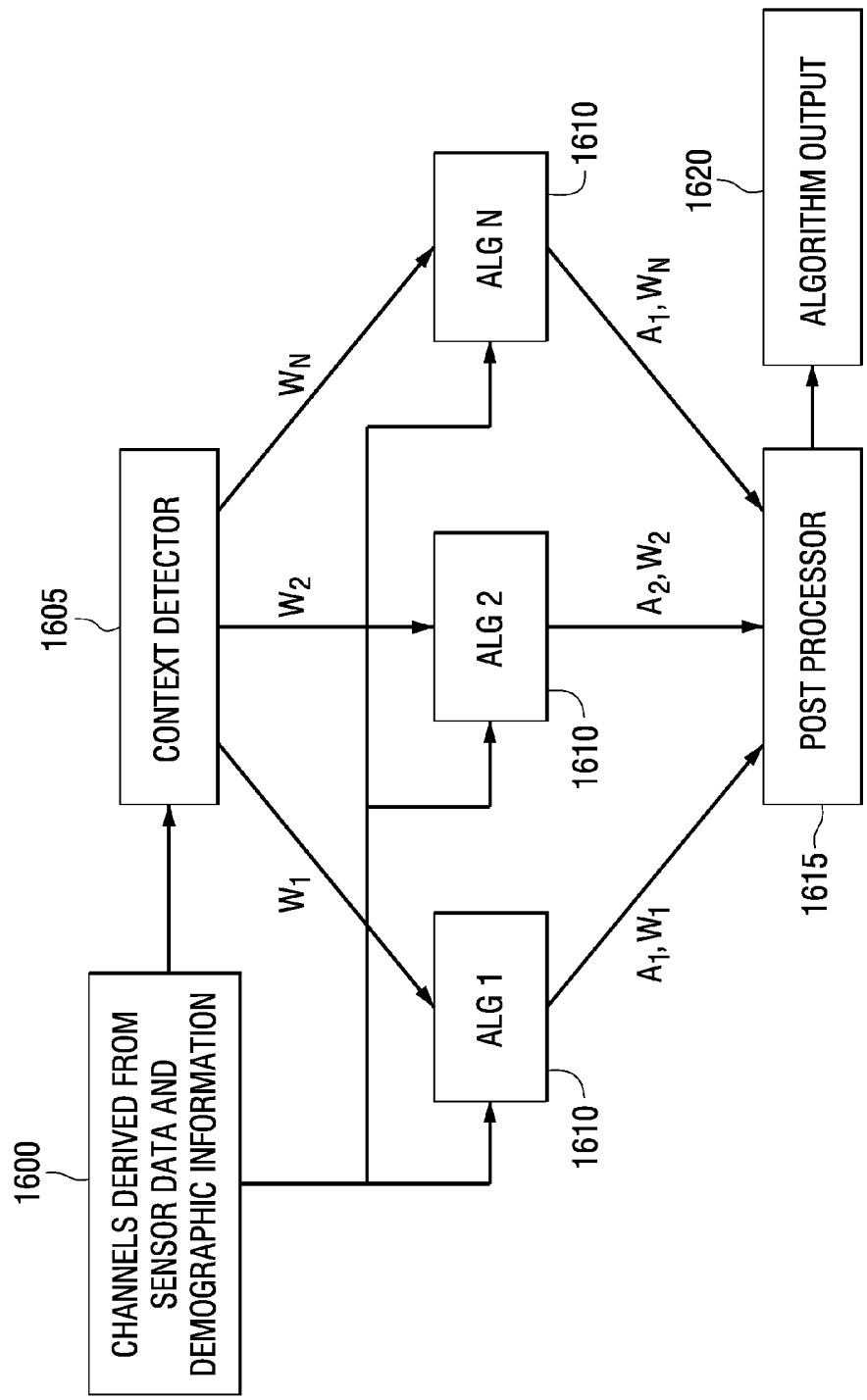
FIG. 29 is a block diagram showing the format of algorithms that are developed according to an aspect of the present invention.

According to a preferred embodiment of the present invention, the algorithms that are developed using this process will have the format shown conceptually in FIG. 29. Specifically, the algorithm will take as inputs the channels derived from the sensor data collected by the sensor device from the various sensors, and demographic information for the individual as shown in box 1600. The algorithm includes at least one context detector 1605 that produces a weight, shown as W1 through WN, expressing the probability that a given portion of collected data, such as is collected over a minute, was collected while the wearer was in each of several possible contexts. Such contexts may include whether the individual was at rest or active. In addition, for each context, a regression algorithm 1610 is provided where a continuous prediction is computed taking raw or derived channels as input. The individual regressions can be any of a variety of regression equations or methods, including, for example, multivariate linear or polynomial regression, memory based methods, support vector machine regression, neural networks, Gaussian processes, arbitrary procedural functions and the like. Each regression is an estimate of the output of the parameter of interest in the algorithm, for example, energy expenditure. Finally, the outputs of each regression algorithm 1610 for each context, shown as A1 through AN, and the weights W1 through WN are combined in a post-processor 1615 which outputs the parameter of interest being measured or predicted by the algorithm, shown in box 1620. In general, the post-processor 1615 can consist of any of many methods for combining the separate contextual predictions, including committee methods, boosting, voting methods, consistency checking, or context based recombination.

Figure 30:
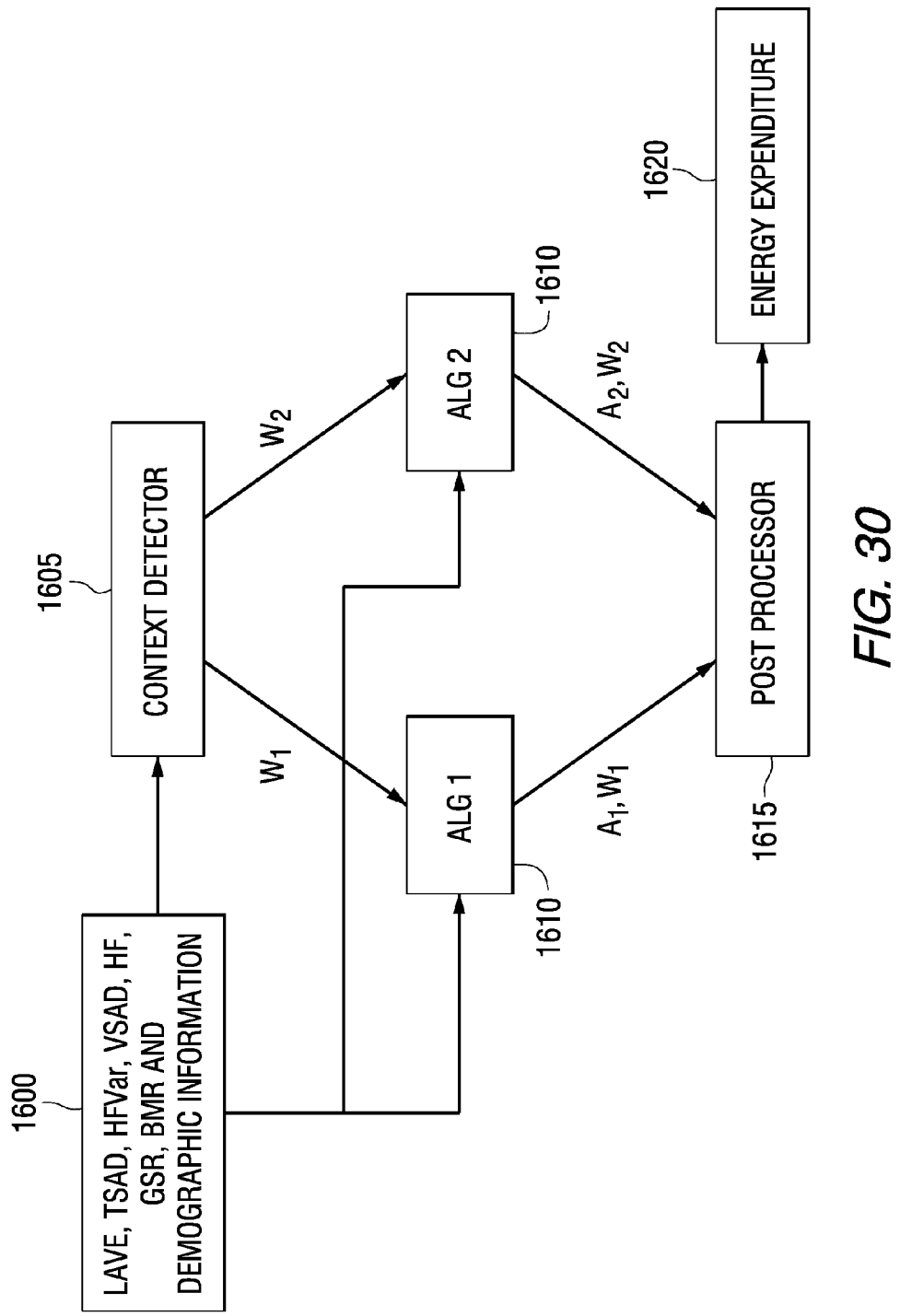
FIG. 30 is a block diagram illustrating an example algorithm for predicting energy expenditure according to the present invention.

Referring to FIG. 30, an example algorithm for measuring energy expenditure of an individual is shown. This example algorithm may be run on sensor device 400 having at least an accelerometer, a heat flux sensor and a GSR sensor, or an I/O device 1200 that receives data from such a sensor device as is disclosed in co-pending U.S. patent application Ser. No. 10/682,759, the specification of which is incorporated herein by reference. In this example algorithm, the raw data from the sensors is calibrated and numerous values based thereon, i.e., derived channels, are created. In particular, the following derived channels, shown at 1600 in FIG. 30, are computed from the raw signals and the demographic information: (1) longitudinal accelerometer average, or LAVE, based on the accelerometer data; (2) transverse accelerometer sum of average differences, or TSAD, based on the accelerometer data; (3) heat flux high gain average variance, or HFvar, based on heat flux sensor data; (4) vector sum of transverse and longitudinal accelerometer sum of absolute differences or SADs, identified as VSAD, based on the accelerometer data; (5) galvanic skin response, or GSR, in both low and combined gain embodiments; and (6) Basal Metabolic Rate or BMR, based on demographic information input by the user. Context detector 1605 consists of a naive Bayesian classifier that predicts whether the wearer is active or resting using the LAVE, TSAD, and HFvar derived channels. The output is a probabilistic weight, W1 and W2 for the two contexts rest and active. For the rest context, the regression algorithm 1610 is a linear regression combining channels derived from the accelerometer, the heat flux sensor, the user's demographic data, and the galvanic skin response sensor. The equation, obtained through the algorithm design process, is $A*VSAD+B*HFvar+C*GSR+D*BMR+E$, where A, B, C, D and E are constants. The regression algorithm 1610 for the active context is the same, except that the constants are different. The post-processor 1615 for this example is to add together the weighted results of each contextual regression. If A1 is the result of the rest regression and A2 is the result of the active regression, then the combination is just $W1*A1+W2*A2$, which is energy expenditure shown at 1620. In another example, a derived channel that calculates whether the wearer is motoring, that is, driving in a car at the time period in question might also be input into the post-processor 1615. The process by which this derived motoring channel is computed is algorithm 3. The post-processor 1615 in this case might then enforce a constraint that when the wearer is predicted to be driving by algorithm 3, the energy expenditure is limited for that time period to a value equal to some factor, e.g. 1.3 times their minute by minute basal metabolic rate.

This algorithm development process may also be used to create algorithms to enable sensor device 400 to detect and measure various other parameters, including, without limitation, the following: (i) when an individual is suffering from duress, including states of unconsciousness, fatigue, shock, drowsiness, heat stress and dehydration; and (ii) an individual's state of readiness, health and/or metabolic status, such as in a military environment, including states of dehydration, under-nourishment and lack of sleep. In addition, algorithms may be developed for other purposes, such as filtering, signal clean-up and noise cancellation for signals measured by a sensor device as described herein. As will be appreciated, the actual algorithm or function that is developed using this method will be highly dependent on the specifics of the sensor device used, such as the specific sensors and placement thereof and the overall structure and geometry of the sensor device. Thus, an algorithm developed with one sensor device will not work as well, if at all, on sensor devices that are not substantially structurally identical to the sensor device used to create the algorithm.

Another aspect of the present invention relates to the ability of the developed algorithms to handle various kinds of uncertainty. Data uncertainty refers to sensor noise and possible sensor failures. Data uncertainty is when one cannot fully trust the data. Under such conditions, for example, if a sensor, for example an accelerometer, fails, the system might conclude that the wearer is sleeping or resting or that no motion is taking place. Under such conditions it is very hard to conclude if the data is bad or if the model that is predicting and making the conclusion is wrong. When an application involves both model and data uncertainties, it is very important to identify the relative magnitudes of the uncertainties associated with data and the model. An intelligent system would notice that the sensor seems to be producing erroneous data and would either switch to alternate algorithms or would, in some cases, be able to fill the gaps intelligently before making any predictions. When neither of these recovery techniques are possible, as was mentioned before, returning a clear statement that an accurate value can not be returned is often much preferable to returning information from an algorithm that has been determined to be likely to be wrong. Determining when sensors have failed and when data channels are no longer reliable is a non-trivial task because a failed sensor can sometimes result in readings that may seem consistent with some of the other sensors and the data can also fall within the normal operating range of the sensor.

Clinical uncertainty refers to the fact that different sensors might indicate seemingly contradictory conclusions. Clinical uncertainty is when one cannot be sure of the conclusion that is drawn from the data. For example, the accelerometers might indicate that the wearer is motionless, leading toward a conclusion of a resting user, the galvanic skin response sensor might provide a very high response, leading toward a conclusion of an active user, the heat flow sensor might indicate that the wearer is still dispersing substantial heat, leading toward a conclusion of an active user, and the heart rate sensor might indicate that the wearer has an elevated heart rate, leading toward a conclusion of an active user. An inferior system might simply try to vote among the sensors or use similarly unfounded methods to integrate the various readings. The present invention weights the important joint probabilities and determines the appropriate most likely conclusion, which might be, for this example, that the wearer is currently performing or has recently performed a low motion activity such as stationary biking.

According to a further aspect of the present invention, a sensor device such as sensor device 400 may be used to automatically measure, record, store and/or report a parameter Y relating to the state of a person, preferably a state of the person that cannot be directly measured by the sensors. State parameter Y may be, for example and without limitation, calories consumed, energy expenditure, sleep states, hydration levels, ketosis levels, shock, insulin levels, physical exhaustion and heat exhaustion, among others. The sensor device is able to observe a vector of raw signals consisting of the outputs of certain of the one or more sensors, which may include all of such sensors or a subset of such sensors. As described above, certain signals, referred to as channels same potential terminology problem here as well, may be derived from the vector of raw sensor signals as well. A vector X of certain of these raw and/or derived channels, referred to herein as the raw and derived channels X, will change in some systematic way depending on or sensitive to the state, event and/or level of either the state parameter Y that is of interest or some indicator of Y, referred to as U, wherein there is a relationship between Y and U such that Y can be obtained from U. According to the present invention, a first algorithm or function f1 is created using the sensor device that takes as inputs the raw and derived channels X and gives an output that predicts and is conditionally dependent, expressed with the symbol $\pi$, on (i) either the state parameter Y or the indicator U, and (ii) some other state parameter(s) Z of the individual. This algorithm or function f1 may be expressed as follows:

$$f1(X) \; \pi \; U+Z$$

or $$f1(X) \; \pi \; Y+Z$$

According to the preferred embodiment, f1 is developed using the algorithm development process described elsewhere herein which uses data, specifically the raw and derived channels X, derived from the signals collected by the sensor device, the verifiable standard data relating to U or Y and Z contemporaneously measured using a method taken to be the correct answer, for example highly accurate medical grade lab equipment, and various machine learning techniques to generate the algorithms from the collected data. The algorithm or function f1 is created under conditions where the indicator U or state parameter Y, whichever the case may be, is present. As will be appreciated, the actual algorithm or function that is developed using this method will be highly dependent on the specifics of the sensor device used, such as the specific sensors and placement thereof and the overall structure and geometry of the senor device. Thus, an algorithm developed with one sensor device will not work as well, if at all, on sensor devices that are not substantially structurally identical to the sensor device used to create the algorithm or at least can be translated from device to device or sensor to sensor with known conversion parameters.

Next, a second algorithm or function f2 is created using the sensor device that takes as inputs the raw and derived channels X and gives an output that predicts and is conditionally dependent on everything output by f1 except either Y or U, whichever the case may be, and is conditionally independent, indicated by the symbol $\perp$, of either Y or U, whichever the case may be. The idea is that certain of the raw and derived channels X from the one or more sensors make it possible to explain away or filter out changes in the raw and derived channels X coming from non-Y or non-U related events. This algorithm or function f2 may be expressed as follows:

$$f2(X) \; \pi \; Z \text{ and } (f2(X) \perp Y \text{ or } f2(X) \perp U$$

Preferably, f2, like f1, is developed using the algorithm development process referenced above. f2, however, is developed and validated under conditions where U or Y, whichever the case may be, is not present. Thus, the gold standard data used to create f2 is data relating to Z only measured using highly accurate medical grade lab equipment.

Thus, according to this aspect of the invention, two functions will have been created, one of which, f1, is sensitive to U or Y, the other of which, f2, is insensitive to U or Y. As will be appreciated, there is a relationship between f1 and f2 that will yield either U or Y, whichever the case may be. In other words, there is a function f3 such that f3 (f1, f2)=U or f3 (f1, f2)=Y. For example, U or Y may be obtained by subtracting the data produced by the two functions (U=f1−f2 or Y=f1−f2). In the case where U, rather than Y, is determined from the relationship between f1 and f2, the next step involves obtaining Y from U based on the relationship between Y and U. For example, Y may be some fixed percentage of U such that Y can be obtained by dividing U by some factor.

One skilled in the art will appreciate that in the present invention, more than two such functions, e.g. (f1, f2, f3, . . . f_n−1) could be combined by a last function f_n in the manner described above. In general, this aspect of the invention requires that a set of functions is combined whose outputs vary from one another in a way that is indicative of the parameter of interest. It will also be appreciated that conditional dependence or independence as used here will be defined to be approximate rather than precise.

The method just described may, for example, be used to automatically measure and/or report the caloric consumption or intake of a person using the sensor device, such as that person's daily caloric intake, also known as DCI. Automatic measuring and reporting of caloric intake would be advantageous because other non-automated methods, such as keeping diaries and journals of food intake, are hard to maintain and because caloric information for food items is not always reliable or, as in the case of a restaurant, readily available.

It is known that total body metabolism is measured as total energy expenditure (TEE) according to the following equation:

$$TEE = BMR + AE + TEF + AT,$$

wherein BMR is basal metabolic rate, which is the energy expended by the body during rest such as sleep, AE is activity energy expenditure, which is the energy expended during physical activity, TEF is thermic effect of food, which is the energy expended while digesting and processing the food that is eaten, and AT is adaptive thermogenesis, which is a mechanism by which the body modifies its metabolism to extreme temperatures. It is estimated that it costs humans about 10% of the value of food that is eaten to process the food. TEF is therefore estimated to be 10% of the total calories consumed. Thus, a reliable and practical method of measuring TEF would enable caloric consumption to be measured without the need to manually track or record food related information. Specifically, once TEF is measured, caloric consumption can be accurately estimated by dividing TEF by 0.1 (TEF=0.1*Calories Consumed; Calories Consumed=TEF/0.1).

According to a specific embodiment of the present invention relating to the automatic measurement of a state parameter Y as described above, a sensor device as described above may be used to automatically measure and/or record calories consumed by an individual. In this embodiment, the state parameter Y is calories consumed by the individual and the indicator U is TEF. First, the sensor device is used to create f1, which is an algorithm for predicting TEE. f1 is developed and validated on subjects who ate food, in other words, subjects who were performing activity and who were experiencing a TEF effect. As such, f1 is referred to as EE(gorge) to represent that it predicts energy expenditure including eating effects. The verifiable standard data used to create f1 is a VO2 machine. The function f1, which predicts TEE, is conditionally dependent on and predicts the item U of interest, which is TEF. In addition, f1 is conditionally dependent on and predicts Z which, in this case, is BMR+AE+AT. Next, the sensor device is used to create f2, which is an algorithm for predicting all aspects of TEE except for TEF. f2 is developed and validated on subjects who fasted for a period of time prior to the collection of data, preferably 4-6 hours, to ensure that TEF was not present and was not a factor. Such subjects will be performing physical activity without any TEF effect. As a result, f2 is conditionally dependent to and predicts BMR+AE+AT but is conditionally independent of and does not predict TEF. As such, f2 is referred to as EE(fast) to represent that it predicts energy expenditure not including eating effects. Thus, f1 so developed will be sensitive to TEF and f2 so developed will be insensitive to TEF. As will be appreciated, in this embodiment, the relationship between f1 and f2 that will yield the indicator U, which in this case is TEF, is subtraction. In other words, EE (gorge)−EE (fast)=TEF.

Once developed, functions $f_1$ and $f_2$ can be programmed into software stored by the sensor device and executed by the processor of the sensor device. Data from which the raw and derived channels X can be derived can then be collected by the sensor device. The outputs of $f_1$ and $f_2$ using the collected data as inputs can then be subtracted to yield TEF. Once TEF is determined for a period of time such as a day, calories consumed can be obtained for that period by dividing TEF by 0.1, since TEF is estimated to be 10% of the total calories consumed. The caloric consumption data so obtained may be stored, reported and/or used in lieu of the manually collected caloric consumption data utilized in the embodiments described elsewhere herein.

Preferably, the sensor device is in communication with a body motion sensor such as an accelerometer adapted to generate data indicative of motion, a skin conductance sensor such as a GSR sensor adapted to generate data indicative of the resistance of the individual's skin to electrical current, a heat flux sensor adapted to generate data indicative of heat flow off the body, a body potential sensor such as an ECG sensor adapted to generate data indicative of the rate or other characteristics of the heart beats of the individual, and a temperature sensor adapted to generate data indicative of a temperature of the individual's skin. In this preferred embodiment, these signals, in addition the demographic information about the wearer, make up the vector of signals from which the raw and derived channels X are derived. Most preferably, this vector of signals includes data indicative of motion, resistance of the individual's skin to electrical current and heat flow off the body.

As a limiting case of attempting to estimate TEF as described above, one can imagine the case where the set of additional state parameters Z is zero. This results in measuring TEF directly through the derivational process using linear and non-linear derivations described earlier. In this variation, the algorithmic process is used to predict TEF directly, which must be provided as the verifiable-standard training data.

As an alternative to TEF, any effect of food on the body, such as, for example, drowsiness, urination or an electrical effect, or any other signs of eating, such as stomach sounds, may be used as the indicator U in the method just described for enabling the automatic measurement of caloric consumption. The relationship between U and the state parameter Y, which is calories consumed, may, in these alternative embodiments, be based on some known or developed scientific property or equation or may be based on statistical modeling techniques.

As an alternate embodiment, DCI can be estimated by combining measurements of weight taken at different times with estimates of energy expenditure. It is known from the literature that weight change (measured multiple times under the same conditions so as to filter out effects of water retention and the digestive process) is related to energy balance and caloric intake as follows: (Caloric Intake−Energy Expenditure)/K=weight gain in pounds, where K is a constant preferably equal to 3500. Thus, given that an aspect of the present invention relates to a method and apparatus for measuring energy expenditure that may take input from a scale, the caloric intake of a person can be accurately estimated based on the following equation: Caloric Intake=Energy Expenditure+(weigh gain in pounds*K). This method requires that the user weigh themselves regularly, but requires no other effort on their part to obtain a measure of caloric intake.

Also note also that DCI can be estimated using an algorithm that takes sensor data and attempts to directly estimate the calories consumed by the wearer, using that number of calories as the verifiable standard and the set of raw and derived channels as the training data. This is just an instance of the algorithmic process described above.

Another specific instantiation where the present invention can be utilized relates to detecting when a person is fatigued. Such detection can either be performed in at least two ways. A first way involves accurately measuring parameters such as their caloric intake, hydration levels, sleep, stress, and energy expenditure levels using a sensor device and using the two function ($f_1$ and $f_2$) approach described with respect to TEF and caloric intake estimation to provide an estimate of fatigue. A second way involves directly attempting to model fatigue using the direct derivational approach described in connection with FIGS. 29 and 30. This example illustrates that complex algorithms that predict the wearer's physiologic state can themselves be used as inputs to other more complex algorithms. One potential application for such an embodiment of the present invention would be for first-responders (e.g. firefighters, police, soldiers) where the wearer is subject to extreme conditions and performance matters significantly. In a pilot study, the assignee of the present invention analyzed data from firefighters undergoing training exercises and determined that reasonable measures of heat stress were possible using combinations of calibrated sensor values. For example, if heat flux is too low for too long a period of time but skin temperature continues to rise, the wearer is likely to have a problem. It will be appreciated that algorithms can use both calibrated sensor values and complex derived algorithms.

According to an alternate embodiment of the present invention, rather than having the software that implements $f_1$ and $f_2$ and determines U and/or Y therefrom be resident on and executed by the sensor device itself, such software may be resident on and run by a computing device separate from the sensor device. In this embodiment, the computing device receives, by wire or wirelessly, the signals collected by the sensor device from which the set of raw and derived channels X are derived and determines U and/or Y from those signals as described above. This alternate embodiment may be an embodiment wherein the state parameter Y that is determined by the computing device is calories consumed and wherein the indicator is some effect on the body of food, such as TEF. The computing device may display the determined caloric consumption data to the user. In addition, the sensor device may also generate caloric expenditure data as described elsewhere herein which is communicated to the computing device. The computing device may then generate and display information based on the caloric consumption data and the caloric expenditure data, such as energy balance data, goal related data, and rate of weight loss or gain data.

The terms and expressions which have been employed herein are used as terms of description and not as limitation, and there is no intention in the use of such terms and expressions of excluding equivalents of the features shown and described or portions thereof, it being recognized that various modifications are possible within the scope of the invention claimed. Although particular embodiments of the present invention have been illustrated in the foregoing detailed description, it is to be further understood that the present invention is not to be limited to just the embodiments disclosed, but that they are capable of numerous rearrangements, modifications and substitutions.

What is claimed is:

1. A system to provide feedback for an individual's weight-loss goal, said system comprising:
   a. a wearable sensor device for detecting data; and
   b. a processing unit in electronic communication with said sensor device, said processing unit configured to accomplish the following steps, thus providing said feedback:
      (i) derive physiological and contextual data of the individual from data detected by said sensor device;
      (ii) prompt said individual to establish a weight-loss goal;
      (iii) generate a first suggestion to engage in an activity to assist said individual to achieve said weight-loss goal;
      (iv) determine weight-loss;
      (v) generate a second suggestion to engage in an activity to assist said individual to achieve said weight-loss goal if said weight-loss goal is not progressing toward the goal;
   wherein said second suggestion is based upon a determination of whether or not the individual complied with said first suggestion; and
   wherein said determination of whether or not the individual complied with said first suggestion is based on said derived physiological and contextual data of the individual.

2. The system of claim 1, wherein said processing unit is further configured to derive an energy balance from said detected data.

3. The system of claim 2, wherein the energy balance is derived from daily caloric intake and energy expenditure.

4. The system of claim 3, wherein said feedback comprises the effect of daily caloric intake and energy expenditure upon each other.

5. The system of claim 2, wherein said processing unit is configured to utilize said energy balance to track and predict changes in human physiological parameters.

6. The system of claim 1, wherein said processing unit is further configured to identify a pattern of behavior from said detected data, to determine whether said pattern affects said user's progress, and to adapt said identified pattern of behavior.

7. The system of claim 6, wherein said pattern is recorded for future review.

8. The system of claim 7, wherein said processing unit is further configured to analyze said recorded patterns to detect one of: (i) current and (ii) future patterns of negative, positive and neutral human physiological status parameters.

9. The system of claim 8, wherein said analysis of recorded patterns are based on one of (i) data from the individual's personal history and (ii) aggregate data of other individuals.

10. The system of claim 1, further comprising a database comprising data.

11. The system of claim 10, wherein said database includes patterns of physiological data.

12. The system of claim 10, wherein said database includes patterns of contextual data.

13. The system of claim 10, wherein said database includes patterns of activity data derived from said detected data.

14. The system of claim 10, wherein said processing unit is further configured to analyze said data in database to establish data patterns.

15. The system of claim 14, wherein said processing unit is further configured to instruct said system to store said data patterns.

16. The system of claim 15, wherein said processing unit is further configured to compare stored data patterns to detected data to identify and categorize said detected data into additional data patterns.

17. The system of claim 15, wherein said processing unit is further configured to (i) compare stored data patterns to detected data to identify such detected data as being similar to at least one of said stored data patterns and (ii) predict future data.

18. The system of claim 17, wherein said processing unit is configured to generate output based upon said prediction of said future data.

19. The system of claim 18, wherein said output is an alarm.

20. The system of claim 18, wherein said output is a report.

21. The system of claim 18, wherein said output is utilized as input by another device.

22. The system of claim 1, wherein said processing unit is further configured to utilize said feedback for the purpose of establishing an initial assessment for a health modification plan.

23. The system of claim 22, wherein said processing unit is further configured to utilize said feedback for assessing interim status of progress toward said health modification plan.

24. The system of claim 1, wherein said first suggestion comprises a plan.

25. The system of claim 1, further comprising an algorithm stored in a memory of the processing unit, the algorithm configured to calculate weight loss or weight gain using inputs from at least one of the sensor and the individual.

26. The system of claim 1, wherein said processing unit is further configured to derive energy expenditure data from said detected data.

27. The system of claim 26, wherein said processing unit is further configured to utilize said energy expenditure data to track and predict changes in the individual's human physiological parameters.

28. The system of claim 1, wherein the system is configured for use in the management of at least one of sleep, pregnancy,. diabetes, cardiovascular disease, wellness, and stress.

29. The system of claim 1, wherein said sensor device comprises at least one of a weight scale and a glucose monitor.

* * * * *

UNITED STATES PATENT AND TRADEMARK OFFICE
CERTIFICATE OF CORRECTION

| | | |
|---|---|---|
| PATENT NO. | : 8,398,546 B2 | Page 1 of 1 |
| APPLICATION NO. | : 10/940214 | |
| DATED | : March 19, 2013 | |
| INVENTOR(S) | : Pacione et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 486 days.

Signed and Sealed this

Second Day of December, 2014

Michelle K. Lee
*Deputy Director of the United States Patent and Trademark Office*